(12) United States Patent
Calcei et al.

(10) Patent No.: US 10,975,159 B2
(45) Date of Patent: Apr. 13, 2021

(54) COMPOUNDS BINDING HUMAN CD160 AND USES THEREOF

(71) Applicant: ELSALYS BIOTECH, Lyons (FR)

(72) Inventors: Alexandre Calcei, Saint Genis Laval (FR); Hélène Haegel, Illkirch-Grafenstaden (FR); Thierry Menguy, Strasbourg (FR); Caroline Rozan, Villeurbanne (FR)

(73) Assignee: ELSALYS BIOTECH, Lyons (FR)

( * ) Notice: Subject to any disclaimer, the term of this patent is extended or adjusted under 35 U.S.C. 154(b) by 0 days.

(21) Appl. No.: 16/476,171

(22) PCT Filed: Jan. 8, 2018

(86) PCT No.: PCT/EP2018/050354
§ 371 (c)(1),
(2) Date: Jul. 5, 2019

(87) PCT Pub. No.: WO2018/127586
PCT Pub. Date: Jul. 12, 2018

(65) Prior Publication Data
US 2020/0109211 A1    Apr. 9, 2020

(30) Foreign Application Priority Data

Jan. 6, 2017   (FR) ...................... 17/50152

(51) Int. Cl.
*C07K 16/28* (2006.01)
*C07K 16/46* (2006.01)

(52) U.S. Cl.
CPC ........ *C07K 16/2896* (2013.01); *C07K 16/464* (2013.01); *C07K 16/468* (2013.01); *C07K 2317/31* (2013.01); *C07K 2317/35* (2013.01)

(58) Field of Classification Search
None
See application file for complete search history.

(56) References Cited

U.S. PATENT DOCUMENTS

| 2004/0018191 | A1* | 1/2004 | Wang | A61P 1/04 |
| | | | | 424/143.1 |
| 2005/0042664 | A1* | 2/2005 | Wu | C07K 16/465 |
| | | | | 435/6.16 |
| 2006/0057149 | A1* | 3/2006 | Johnson | G01N 33/56983 |
| | | | | 424/159.1 |
| 2014/0046039 | A1* | 2/2014 | Ahmed | A61P 31/16 |
| | | | | 530/389.4 |
| 2014/0348851 | A1* | 11/2014 | Ahmed | A61P 31/16 |
| | | | | 424/147.1 |
| 2017/0015742 | A1* | 1/2017 | Gu | A61P 3/00 |

FOREIGN PATENT DOCUMENTS

| CA | 2977142 A1 * | 8/2016 | ........ G01N 33/56983 |
| EP | 1626059 A1 | 2/2006 | |
| EP | 1776387 B1 | 7/2010 | |
| WO | 98/21240 A1 | 5/1998 | |
| WO | 2008/155363 A2 | 12/2008 | |
| WO | 2010/084158 A1 | 7/2010 | |
| WO | 2011/147984 A1 | 12/2011 | |
| WO | WO-2014177652 A1 * | 11/2014 | ............. A61K 39/00 |
| WO | WO-2017114694 A1 * | 7/2017 | ......... C07K 16/2809 |

OTHER PUBLICATIONS

Cai et al, "CD160 inhibits activation of human CD4+ T cells through interaction with herpesvirus entry mediator", 2008, Nature Immunology vol. 9, pp. 176-185 (Year: 2008).*
"Antibodies—Structure and Sequence" [online, 2001 archive accessed from] [https://web.archive.org/web/20010214233200/http://www.bioinf.org.uk/abs/] (Year: 2001).*
CD160 [*Homo sapiens*]. [online reference] [accessed from: https://www.ncbi.nlm.nih.gov/protein/CAG46665.1?report=genpept] (Year: 2008).*
Labrijn et al. "Species-Specific Determinants in the IgG CH3 Domain Enable Fab-Arm Exchange by Affecting the Noncovalent CH3-CH3 Interaction Strength." J Immunol 2011; 187:3238-3246 (Year: 2011).*
Ravn et al. "Structural and Pharmacological Characterization of Novel Potent and Selective Monoclonal Antibody Antagonists of Glucose-dependent Insulinotropic Polypeptide Receptor". The Journal of Biological Chemistry vol. 288, No. 27, pp. 19760-19772, Jul. 5, 2013 (Year: 2013).*
Ravn et al. "Chain C, Gipg013 Fab, Antagonizing Antibody to the Gip Receptor, Heavy Chain" [online] [accessed from https://www.ncbi.nlm.nih.gov/protein/4HJ0_C] (Year: 2013).*
Zhang et al. "High levels of CD160 expression up-regulated counts of chronic lymphocytic leukemia cells and were associated with other clinical parameters in Chinese patients with chronic lymphocytic leukemia". Leukemia & Lymphoma, 56:2, 529-532 (Year: 2015).*
"Prevent—Definition and Synonyms" MacMillan Dictionary. [online][2015 archived version downloaded using the Wayback Machine from https://web.archive.Org/web/20150322020300/https://www.macmillandictionary.com/us/dictionary/american/prevent]. (Year: 2015).*
Safdari et al. "Antibody humanization methods—a review and update". Biotechnology and Genetic Engineering Reviews, 2013. vol. 29, No. 2, 175-186. (Year: 2013).*

(Continued)

*Primary Examiner* — Joanne Hama
*Assistant Examiner* — Scott T. Humbarger
(74) *Attorney, Agent, or Firm* — Oliff PLC

(57) ABSTRACT

Novel compounds which bind specifically to human CD160, including a light chain variable domain (VL), a chosen sequence defined by SEQ ID No: 14 or SEQ ID No: 13 and a heavy chain variable domain (VH), a sequence chosen from SEQ ID No: 11, SEQ ID No: 25, SEQ ID No: 26, SEQ ID No: 27, SEQ ID No: 28, SEQ ID No: 29 or SEQ ID No: 30, fragments thereof or derivatives thereof.

20 Claims, 15 Drawing Sheets
Specification includes a Sequence Listing.

(56) References Cited

OTHER PUBLICATIONS

Apr. 17, 2018 International Search Report issued in International Patent Application No. PCT/EP2018/050354.

Apr. 17, 2018 Written Opinion issued in International Patent Application No. PCT/EP2018/050354.

De Jong et al. "A Novel Platform for the Potentiation of Therapeutic Antibodies Based on Antigen-Dependent Formation of IgG Hexamers at the Cell Surface." PLoS Biology: e 1002344, DOI: 10.1371/journal, Jan. 6, 2016, vol. 14, No. 1, pp. 1-24.

Diebolder et al. "Complement Is Activated by IgG Hexamers Assembled at the Cell Surface." Science, Mar. 14, 2014, vol. 343, No. 6176, pp. 1260-1263, doi: 10.1126/science.1248943.

El-Far et al. "CD160 isoforms and regulation of CD4 and CD8 T-cell responses." Journal of Translational Medicine, 2014, vol. 12, No. 217.

Gadkar et al. "Design and Pharmacokinetic Characterization of Novel Antibody Formats for Ocular Therapeutics." Investigative Ophthalmology and Visual Science, Aug. 2015, vol. 56, No. 9, pp. 5390-5400.

Krzystolik et al. "Prevention of Experimental Choroidal Neovascularization With Intravitreal Anti-Vascular Endothelial Growth Factor Antibody Fragment." Archives of Ophthalmology, Mar. 2002, vol. 120, 338-346.

Labrijn et al. "Controlled Fab-arm exchange for the generation of stable bispecific IgG1." Nature Protocols, 2014, vol. 9, No. 10, 2450-2463.

Wang et al. "Molecular Basis of Assembly and Activation of Complement Component C1 in Complex with Immunoglobulin G1 and Antigen." Molecular Cell, Jul. 7, 2016, vol. 63, pp. 135-145.

Giustiniani et al. "Identification and characterization of a transmembrane isoform of CD160 (CD160-TM), a unique activating receptor selectively expressed upon human NK cell activation." Journal of Immunology, Jan. 2009, vol. 182, No. 1, pp. 63-71.

\* cited by examiner

SEQUENCE LISTING

<160> NUMBER OF SEQ ID NOS: 64

<210> SEQ ID NO 1
<211> LENGTH: 121
<212> TYPE: PRT
<213> ORGANISM: Mus musculus

<400> SEQUENCE: 1

Gln Val His Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Trp Met Gln Trp Ile Lys Gln Arg Pro Gly Gln Gly Leu Glu Trp Ile
        35                  40                  45

Gly Ser Ile Tyr Pro Gly Asp Asp Ala Arg Tyr Thr Gln Lys Phe
    50                  55                  60

Arg Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser
        115                 120

<210> SEQ ID NO 2
<211> LENGTH: 107
<212> TYPE: PRT
<213> ORGANISM: Mus musculus

<400> SEQUENCE: 2

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Ser Asn His
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

```
Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Leu Lys
            100                 105

<210> SEQ ID NO 3
<211> LENGTH: 10
<212> TYPE: PRT
<213> ORGANISM: Mus musculus

<400> SEQUENCE: 3

Gly Tyr Thr Phe Thr Asp Tyr Trp Met Gln
1               5                   10

<210> SEQ ID NO 4
<211> LENGTH: 16
<212> TYPE: PRT
<213> ORGANISM: Mus musculus

<400> SEQUENCE: 4

Ser Ile Tyr Pro Gly Asp Asp Asp Ala Arg Tyr Thr Gln Lys Phe Arg
1               5                   10                  15

<210> SEQ ID NO 5
<211> LENGTH: 12
<212> TYPE: PRT
<213> ORGANISM: Mus musculus

<400> SEQUENCE: 5

Arg Gly Ile Ala Ala Val Val Gly Gly Phe Asp Tyr
1               5                   10

<210> SEQ ID NO 6
<211> LENGTH: 11
<212> TYPE: PRT
<213> ORGANISM: Mus musculus

<400> SEQUENCE: 6

Arg Ala Ser Gln Ser Ile Ser Asn His Leu His
1               5                   10

<210> SEQ ID NO 7
<211> LENGTH: 7
<212> TYPE: PRT
<213> ORGANISM: murine retrovirus Cas NS-1

<400> SEQUENCE: 7

Tyr Ala Ser Gln Ser Ile Ser
1               5

<210> SEQ ID NO 8
<211> LENGTH: 9
<212> TYPE: PRT
<213> ORGANISM: Mus musculus

<400> SEQUENCE: 8

Gln Gln Ser Asn Ser Trp Pro Leu Thr
1               5

<210> SEQ ID NO 9
<211> LENGTH: 447
```

<212> TYPE: PRT
<213> ORGANISM: Homo sapiens

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
50                  55                  60

Arg Gly Arg Ala Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Phe Asp Tyr Trp Gly
                100                 105                 110

Gln Gly Thr Thr Leu Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly
    435                 440                 445

<210> SEQ ID NO 10
<211> LENGTH: 447
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Tyr Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Gly Leu Pro Ser Ser Ile Glu Lys Thr
```

```
                    325                 330                 335
Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
                420                 425                 430

Leu His Asn Gln Tyr Thr Gln Lys Ser Leu Ser Leu Ser Leu Gly
                435                 440                 445

<210> SEQ ID NO 11
<211> LENGTH: 121
<212> TYPE: PRT
<213> ORGANISM: Artificial Sequence
<220> FEATURE:
<223> OTHER INFORMATION: humanized sequence

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met Gln Trp Ile Arg Gln Ala Pro Gly Gln Gly Leu Glu Trp Ile
        35                  40                  45

Gly Ser Ile Tyr Pro Gly Asp Asp Ala Arg Tyr Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: humanized sequence

<400> SEQUENCE: 12

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Ser Asn His
            20                  25                  30

Leu His Trp Tyr Gln Gln Lys Pro Gly Lys Ala Pro Lys Leu Leu Ile
        35                  40                  45

Lys Tyr Ala Ser Gln Ser Ile Ser Gly Val Pro Ser Arg Phe Ser Gly
    50                  55                  60
```

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Ser Asn Ser Trp Pro Leu
            85                  90                  95

Thr Phe Gly Gly Gly Thr Lys Val Glu Ile Lys
            100                 105

<210> SEQ ID NO 13
<211> LENGTH: 443
<212> TYPE: PRT
<213> ORGANISM: Homo sapiens

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Tyr Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Phe Asp Tyr Trp Gly
            100                 105                 110

Gln Gly Thr Thr Leu Thr Val Ser Ser Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ala Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

```
Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 14
<211> LENGTH: 107
<212> TYPE: PRT
<213> ORGANISM: Artificial Sequence
<220> FEATURE:
<223> OTHER INFORMATION: humanized sequence

<400> SEQUENCE: 14

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn His
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Leu
                85                  90                  95

Thr Phe Gly Gly Gly Thr Lys Val Glu Ile Lys
            100                 105
```

<210> SEQ ID NO 15
<211> LENGTH: 326
<212> TYPE: PRT
<213> ORGANISM: Homo sapiens

<400> SEQUENCE: 15

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

```
Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 16
<211> LENGTH: 329
<212> TYPE: PRT
<213> ORGANISM: Homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 17
<211> LENGTH: 98
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 18
<211> LENGTH: 19
<212> TYPE: PRT
<213> ORGANISM: Artificial Sequence
<220> FEATURE:
<223> OTHER INFORMATION: peptide signal

<400> SEQUENCE: 18

Met Glu Trp Ser Trp Val Phe Leu Phe Phe Leu Ser Val Thr Thr Gly
1               5                   10                  15

Val His Ser

<210> SEQ ID NO 19
<211> LENGTH: 20
<212> TYPE: PRT
<213> ORGANISM: Artificial Sequence
<220> FEATURE:
<223> OTHER INFORMATION: peptide signal

<400> SEQUENCE: 19

Met Asp Trp Pro Val His Leu Leu Val Leu Leu Phe Trp Ile Pro
1               5                   10                  15

Gly Ala Met Ala
            20

<210> SEQ ID NO 20
<211> LENGTH: 20
<212> TYPE: PRT
<213> ORGANISM: Artificial Sequence
<220> FEATURE:
<223> OTHER INFORMATION: peptide signal

<400> SEQUENCE: 20

Met Ser Val Pro Thr Gln Val Leu Gly Leu Leu Leu Leu Trp Leu Thr
1               5                   10                  15

Asp Ala Arg Cys
            20

<210> SEQ ID NO 21
<211> LENGTH: 20
<212> TYPE: PRT
<213> ORGANISM: Artificial Sequence
<220> FEATURE:
<223> OTHER INFORMATION: peptide signal

<400> SEQUENCE: 21

Met Asp Trp Pro Val His Leu Leu Val Leu Leu Phe Trp Ile Pro
1               5                   10                  15

Gly Val Arg Ala
            20

<210> SEQ ID NO 22
<211> LENGTH: 107
<212> TYPE: PRT
<213> ORGANISM: Homo sapiens

<400> SEQUENCE: 22

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 23
<211> LENGTH: 107
<212> TYPE: PRT
<213> ORGANISM: Homo sapiens

<400> SEQUENCE: 23

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Val Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 24
<211> LENGTH: 107
<212> TYPE: PRT
<213> ORGANISM: Homo sapiens

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 25
<211> LENGTH: 121
<212> TYPE: PRT
<213> ORGANISM: Homo sapiens

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Tyr Thr Gln Lys Phe
    50                  55                  60

Arg Gly Arg Ala Thr Leu Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser
            115                 120

<210> SEQ ID NO 26
<211> LENGTH: 121
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Glu Ser
                20                  25                  30

Trp Met Gln Trp Ile Arg Gln Ala Pro Gly Gln Gly Leu Glu Trp Ile
            35                  40                  45

Gly Ala Ile Tyr Pro Gly Asp Asp Glu Ala Arg Val Thr Gln Lys Phe
        50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser
            115                 120

<210> SEQ ID NO 27
<211> LENGTH: 121
<212> TYPE: PRT
<213> ORGANISM: Homo sapiens

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met Gln Trp Ile Arg Gln Ala Pro Gly Gln Gly Leu Glu Trp Ile
            35                  40                  45

Gly Ala Ile Tyr Pro Gly Asp Asp Ala Gln Phe Thr Gln Lys Phe
        50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser
            115                 120

<210> SEQ ID NO 28
<211> LENGTH: 121
<212> TYPE: PRT
<213> ORGANISM: Homo sapiens
```

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asp Tyr
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Gln Tyr Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
                100                 105                 110

Gln Gly Thr Thr Leu Thr Val Ser Ser
            115                 120
```

<210> SEQ ID NO 29
<211> LENGTH: 121
<212> TYPE: PRT
<213> ORGANISM: Homo sapiens

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
                100                 105                 110

Gln Gly Thr Thr Leu Thr Val Ser Ser
            115                 120
```

<210> SEQ ID NO 30
<211> LENGTH: 121
<212> TYPE: PRT
<213> ORGANISM: Homo sapiens

<400> SEQUENCE: 30

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60
```

```
Arg Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser
            115                 120

<210> SEQ ID NO 31
<211> LENGTH: 326
<212> TYPE: PRT
<213> ORGANISM: Homo sapiens

<400> SEQUENCE: 31

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320
```

Leu Ser Leu Ser Leu Gly
            325

<210> SEQ ID NO 32
<211> LENGTH: 326
<212> TYPE: PRT
<213> ORGANISM: Homo sapiens

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu Ala Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
290                 295                 300

Cys Ser Val Met His Glu Ala Leu His Asn Gln Tyr Thr Gln Lys Ser
305                 310                 315                 320

Leu Ser Leu Ser Leu Gly
            325

<210> SEQ ID NO 33
<211> LENGTH: 326
<212> TYPE: PRT

<213> ORGANISM: Homo sapiens

<400> SEQUENCE: 33

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ala Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Gln Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 34
<211> LENGTH: 329
<212> TYPE: PRT
<213> ORGANISM: HoJo virus

<400> SEQUENCE: 34

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

-continued

```
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Gln Ser Thr Tyr Arg Val Val Ser Val Leu Thr Val Leu
            180                 185                 190
Ala Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn Gln Tyr Thr
305                 310                 315                 320
Gln Lys Ser Leu Ser Leu Ser Pro Gly
                325

<210> SEQ ID NO 35
<211> LENGTH: 329
<212> TYPE: PRT
<213> ORGANISM: Homo sapiens

<400> SEQUENCE: 35

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
```

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ala Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 36
<211> LENGTH: 229
<212> TYPE: PRT
<213> ORGANISM: Homo sapiens

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met Gln Trp Ile Arg Gln Ala Pro Gly Gln Gly Leu Glu Trp Ile
        35                  40                  45

Gly Ser Ile Tyr Pro Gly Asp Asp Ala Arg Tyr Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr
225

<210> SEQ ID NO 37
<211> LENGTH: 219
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val
    210                 215

<210> SEQ ID NO 38
<211> LENGTH: 235
<212> TYPE: PRT

-continued

<213> ORGANISM: Homo sapiens

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
                20                  25                  30

Trp Met Gln Trp Ile Arg Gln Ala Pro Gly Gln Gly Leu Glu Trp Ile
            35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Phe Asp Tyr Trp Gly
            100                 105                 110

Gln Gly Thr Thr Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala
225                 230                 235

<210> SEQ ID NO 39
<211> LENGTH: 15
<212> TYPE: PRT
<213> ORGANISM: Homo sapiens

<400> SEQUENCE: 39

Gly Gly Gly Gly Ser Gly Gly Gly Gly Ser Gly Gly Gly Gly Ser
1               5                   10                  15

<210> SEQ ID NO 40
<211> LENGTH: 467
<212> TYPE: PRT
<213> ORGANISM: Homo sapiens

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met Gln Trp Ile Arg Gln Ala Pro Gly Gln Gly Leu Glu Trp Ile
            35                  40                  45

Gly Ser Ile Tyr Pro Gly Asp Asp Ala Arg Tyr Thr Gln Lys Phe
    50                  55                  60

```
Arg Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Gly Gly Gly Gly Ser Gly Gly Gly Gly Ser Gly Gly Gly Gly
225                 230                 235                 240

Ser Gln Val Gln Leu Val Gln Ser Gly Ala Glu Val Lys Lys Pro Gly
                245                 250                 255

Ala Ser Val Lys Val Ser Cys Lys Ala Ser Gly Tyr Thr Phe Thr Asp
            260                 265                 270

Tyr Trp Met Gln Trp Ile Arg Gln Ala Pro Gly Gln Gly Leu Glu Trp
        275                 280                 285

Ile Gly Ser Ile Tyr Pro Gly Asp Asp Ala Arg Tyr Thr Gln Lys
290                 295                 300

Phe Arg Gly Arg Ala Thr Leu Thr Ala Asp Lys Ser Thr Ser Thr Ala
305                 310                 315                 320

Tyr Met Glu Leu Ser Ser Leu Arg Ser Glu Asp Thr Ala Val Tyr Tyr
                325                 330                 335

Cys Ala Arg Arg Gly Ile Ala Ala Val Val Gly Gly Phe Asp Tyr Trp
            340                 345                 350

Gly Gln Gly Thr Thr Leu Thr Val Ser Ser Ala Ser Thr Lys Gly Pro
        355                 360                 365

Ser Val Phe Pro Leu Ala Pro Ser Ser Lys Ser Thr Ser Gly Gly Thr
370                 375                 380

Ala Ala Leu Gly Cys Leu Val Lys Asp Tyr Phe Pro Glu Pro Val Thr
385                 390                 395                 400

Val Ser Trp Asn Ser Gly Ala Leu Thr Ser Gly Val His Thr Phe Pro
                405                 410                 415

Ala Val Leu Gln Ser Ser Gly Leu Tyr Ser Leu Ser Ser Val Val Thr
            420                 425                 430

Val Pro Ser Ser Ser Leu Gly Thr Gln Thr Tyr Ile Cys Asn Val Asn
        435                 440                 445

His Lys Pro Ser Asn Thr Lys Val Asp Lys Arg Val Glu Pro Lys Ser
450                 455                 460

Cys Asp Lys
465
```

```
<210> SEQ ID NO 41
<211> LENGTH: 467
<212> TYPE: PRT
<213> ORGANISM: Homo sapiens

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Phe Asp Tyr Trp Gly
            100                 105                 110

Gln Gly Thr Thr Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Gly Gly Gly Gly Ser Gly Gly Gly Gly Ser Gly Gly Gly Gly
225                 230                 235                 240

Ser Gln Val Gln Leu Val Gln Ser Gly Ala Glu Val Lys Lys Pro Gly
                245                 250                 255

Ala Ser Val Lys Val Ser Cys Lys Ala Ser Gly Tyr Thr Phe Ser Asp
            260                 265                 270

Phe Trp Met Gln Trp Ile Arg Gln Ala Pro Gly Gln Gly Leu Glu Trp
        275                 280                 285

Ile Gly Ala Ile Tyr Pro Gly Asp Asp Ala Arg Val Thr Gln Lys
    290                 295                 300

Phe Arg Gly Arg Ala Thr Leu Thr Ala Asp Lys Ser Thr Ser Thr Ala
305                 310                 315                 320

Tyr Met Glu Leu Ser Ser Leu Arg Ser Glu Asp Thr Ala Val Tyr Tyr
                325                 330                 335

Cys Ala Arg Arg Gly Ile Ala Ala Val Val Gly Phe Asp Tyr Trp
            340                 345                 350

Gly Gln Gly Thr Thr Leu Thr Val Ser Ser Ala Ser Thr Lys Gly Pro
            355                 360                 365

Ser Val Phe Pro Leu Ala Pro Ser Ser Lys Ser Thr Ser Gly Gly Thr
370                 375                 380
```

```
Ala Ala Leu Gly Cys Leu Val Lys Asp Tyr Phe Pro Glu Pro Val Thr
385                 390                 395                 400

Val Ser Trp Asn Ser Gly Ala Leu Thr Ser Gly Val His Thr Phe Pro
            405                 410                 415

Ala Val Leu Gln Ser Ser Gly Leu Tyr Ser Leu Ser Val Val Thr
        420                 425                 430

Val Pro Ser Ser Ser Leu Gly Thr Gln Thr Tyr Ile Cys Asn Val Asn
        435                 440                 445

His Lys Pro Ser Asn Thr Lys Val Asp Lys Arg Val Glu Pro Lys Ser
    450                 455                 460

Cys Asp Lys
465

<210> SEQ ID NO 42
<211> LENGTH: 704
<212> TYPE: PRT
<213> ORGANISM: Homo sapiens

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Gly Gly Gly Gly Ser Gly Gly Gly Ser Ile Glu Gly Arg Gly
225                 230                 235                 240

Gly Gly Gly Ser Gly Gly Gly Gly Ser Gly Gly Gly Gly Ser Gln Val
                245                 250                 255

Gln Leu Val Gln Ser Gly Ala Glu Val Lys Lys Pro Gly Ala Ser Val
            260                 265                 270

Lys Val Ser Cys Lys Ala Ser Gly Tyr Thr Phe Ser Asp Phe Trp Met
```

```
            275                 280                 285
Gln Trp Ile Arg Gln Ala Pro Gly Gln Gly Leu Glu Trp Ile Gly Ala
        290                 295                 300

Ile Tyr Pro Gly Asp Asp Ala Arg Val Thr Gln Lys Phe Arg Gly
305                 310                 315                 320

Arg Ala Thr Leu Thr Ala Asp Lys Ser Thr Ser Thr Ala Tyr Met Glu
                325                 330                 335

Leu Ser Ser Leu Arg Ser Glu Asp Thr Ala Val Tyr Tyr Cys Ala Arg
            340                 345                 350

Arg Gly Ile Ala Ala Val Val Gly Gly Phe Asp Tyr Trp Gly Gln Gly
        355                 360                 365

Thr Thr Leu Thr Val Ser Ser Ala Ser Thr Lys Gly Pro Ser Val Phe
    370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Gln Thr Tyr Ile Cys Asn Val Asn His Lys Pro
    450                 455                 460

Ser Asn Thr Lys Val Asp Lys Arg Val Glu Pro Lys Ser Cys Asp Lys
465                 470                 475                 480

Thr His Thr Cys Pro Pro Cys Pro Ala Pro Glu Leu Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu Ala Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Ser Arg Glu Glu Met Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Leu Leu Tyr Ser Lys Leu Thr Val Asp Lys
            660                 665                 670

Ser Arg Trp Gln Gln Gly Asn Val Phe Ser Cys Ser Val Met His Glu
        675                 680                 685

Ala Leu His Asn Gln Tyr Thr Gln Lys Ser Leu Ser Leu Ser Pro Gly
    690                 695                 700
```

<210> SEQ ID NO 43
<211> LENGTH: 329
<212> TYPE: PRT
<213> ORGANISM: Homo sapiens

<400> SEQUENCE: 43

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 44
<211> LENGTH: 329
<212> TYPE: PRT
<213> ORGANISM: Homo sapiens

<400> SEQUENCE: 44

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Ser Leu Ser Leu Ser Pro Gly
                325

<210> SEQ ID NO 45
<211> LENGTH: 450
<212> TYPE: PRT
<213> ORGANISM: Homo sapiens

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
```

```
            35                  40                  45
Gly Ala Ile Tyr Pro Gly Asp Asp Ala Arg Val Thr Gln Lys Phe
 50                  55                  60

Arg Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Ile Ala Ala Val Val Gly Gly Phe Asp Tyr Trp Gly
                100                 105                 110

Gln Gly Thr Thr Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 46
<211> LENGTH: 450
<212> TYPE: PRT
<213> ORGANISM: Homo sapiens

<400> SEQUENCE: 46

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Ser Asp Tyr
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Tyr Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Phe Asp Tyr Trp Gly
        100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
```

```
                    370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 47
<211> LENGTH: 450
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Trp Met Gln Trp Ile Arg Gln Ala Pro Gly Gln Gly Leu Glu Trp Ile
            35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Gly Gly Phe Asp Tyr Trp Gly
            100                 105                 110

Gln Gly Thr Thr Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 48
<211> LENGTH: 450
<212> TYPE: PRT
<213> ORGANISM: Homo sapiens

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met Gln Trp Ile Arg Gln Ala Pro Gly Gln Gly Leu Glu Trp Ile
            35                  40                  45

Gly Ser Ile Tyr Pro Gly Asp Asp Ala Arg Tyr Thr Gln Lys Phe
50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

```
Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 49
<211> LENGTH: 450
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
```

```
            115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 50
<211> LENGTH: 450
<212> TYPE: PRT
<213> ORGANISM: Homo sapiens

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30
```

```
Trp Met Gln Trp Ile Arg Gln Ala Pro Gly Gln Gly Leu Glu Trp Ile
        35                  40                  45
Gly Ala Ile Tyr Pro Gly Asp Asp Ala Arg Tyr Thr Gln Lys Phe
 50                  55                  60
Arg Gly Arg Ala Thr Leu Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Arg Gly Ile Ala Ala Val Gly Gly Phe Asp Tyr Trp Gly
                100                 105                 110
Gln Gly Thr Thr Leu Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly
```

<210> SEQ ID NO 51
<211> LENGTH: 450
<212> TYPE: PRT
<213> ORGANISM: Homo sapiens

<400> SEQUENCE: 51

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 52
<211> LENGTH: 497
<212> TYPE: PRT
<213> ORGANISM: Homo sapiens

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn His
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ala Ser Val Lys Val Ser Cys
130                 135                 140

Lys Ala Ser Gly Tyr Thr Phe Ser Asp Phe Trp Met Gln Trp Ile Arg
145                 150                 155                 160

Gln Ala Pro Gly Gln Gly Leu Glu Trp Ile Gly Ala Ile Tyr Pro Gly
                165                 170                 175

Asp Asp Asp Ala Arg Val Thr Gln Lys Phe Arg Gly Arg Ala Thr Leu
            180                 185                 190

Thr Ala Asp Lys Ser Thr Ser Thr Ala Tyr Met Glu Leu Ser Ser Leu
            195                 200                 205

Arg Ser Glu Asp Thr Ala Val Tyr Tyr Cys Ala Arg Arg Gly Ile Ala
210                 215                 220

Ala Val Val Gly Gly Phe Asp Tyr Trp Gly Gln Gly Thr Thr Leu Thr
225                 230                 235                 240

Val Ser Ser Gly Gly Gly Gly Ser Asp Ile Lys Leu Gln Gln Ser Gly
                245                 250                 255

Ala Glu Leu Ala Arg Pro Gly Ala Ser Val Lys Met Ser Cys Lys Thr
            260                 265                 270

Ser Gly Tyr Thr Phe Thr Arg Tyr Thr Met His Trp Val Lys Gln Arg
        275                 280                 285
```

```
Pro Gly Gln Gly Leu Glu Trp Ile Gly Tyr Ile Asn Pro Ser Arg Gly
    290                 295                 300

Tyr Thr Asn Tyr Asn Gln Lys Phe Lys Asp Lys Ala Thr Leu Thr Thr
305                 310                 315                 320

Asp Lys Ser Ser Thr Ala Tyr Met Gln Leu Ser Ser Leu Thr Ser
                325                 330                 335

Glu Asp Ser Ala Val Tyr Tyr Cys Ala Arg Tyr Tyr Asp Asp His Tyr
                340                 345                 350

Cys Leu Asp Tyr Trp Gly Gln Gly Thr Thr Leu Thr Val Ser Ser Val
            355                 360                 365

Glu Gly Gly Ser Gly Gly Ser Gly Gly Ser Gly Gly Val
370                 375                 380

Asp Asp Ile Gln Leu Thr Gln Ser Pro Ala Ile Met Ser Ala Ser Pro
385                 390                 395                 400

Gly Glu Lys Val Thr Met Thr Cys Arg Ala Ser Ser Ser Val Ser Tyr
                405                 410                 415

Met Asn Trp Tyr Gln Gln Lys Ser Gly Thr Ser Pro Lys Arg Trp Ile
                420                 425                 430

Tyr Asp Thr Ser Lys Val Ala Ser Gly Val Pro Tyr Arg Phe Ser Gly
            435                 440                 445

Ser Gly Ser Gly Thr Ser Tyr Ser Leu Thr Ile Ser Ser Met Glu Ala
450                 455                 460

Glu Asp Ala Ala Thr Tyr Tyr Cys Gln Gln Trp Ser Ser Asn Pro Leu
465                 470                 475                 480

Thr Phe Gly Ala Gly Thr Lys Leu Glu Leu Lys His His His His
                485                 490                 495

His

<210> SEQ ID NO 53
<211> LENGTH: 450
<212> TYPE: PRT
<213> ORGANISM: Mus musculus

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
                20                  25                  30

Trp Met Gln Trp Ile Arg Gln Ala Pro Gly Gln Gly Leu Glu Trp Ile
            35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Gly Gly Phe Asp Tyr Trp Gly
            100                 105                 110

Gln Gly Thr Thr Leu Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160
```

```
Thr Trp Asn Ser Gly Ser Leu Ser Ser Gly Val His Thr Phe Pro Ala
            165                 170                 175

Val Leu Gln Ser Asp Leu Tyr Thr Leu Ser Ser Val Thr Val Thr
        180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
        210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
                260                 265                 270

Asp Asp Pro Asp Val Gln Ile Ser Trp Phe Val Asn Asn Val Glu Val
            275                 280                 285

His Thr Ala Gln Thr Gln Thr His Arg Glu Asp Tyr Asn Ser Thr Leu
290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Glu Glu Met Thr Lys Lys Gln Val Thr
            355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
        435                 440                 445

Pro Gly
    450

<210> SEQ ID NO 54
<211> LENGTH: 213
<212> TYPE: PRT
<213> ORGANISM: Mus musculus

<400> SEQUENCE: 54

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn His
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Phe Cys Gln Gln Ser Asn Ser Trp Pro Leu
                    85                  90                  95

Thr Phe Gly Gly Gly Thr Lys Val Glu Ile Lys Ala Asp Ala Ala Pro
                100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
            130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
                195                 200                 205

Asn Arg Asn Glu Cys
210

<210> SEQ ID NO 55
<211> LENGTH: 450
<212> TYPE: PRT
<213> ORGANISM: Mus musculus

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Trp Met Gln Trp Ile Arg Gln Ala Pro Gly Gln Gly Leu Glu Trp Ile
            35                  40                  45

Gly Ala Ile Tyr Pro Gly Asp Asp Ala Arg Tyr Thr Gln Lys Phe
        50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Phe Asp Tyr Trp Gly
                100                 105                 110

Gln Gly Thr Thr Leu Thr Val Ser Ser Ala Lys Thr Thr Ala Pro Ser
            115                 120                 125

Val Tyr Pro Leu Ala Pro Val Cys Gly Asp Thr Thr Gly Ser Ser Val
        130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
                180                 185                 190

Ser Ser Thr Trp Pro Ser Gln Ser Ile Thr Cys Asn Val Ala His Pro
            195                 200                 205

Ala Ser Ser Thr Lys Val Asp Lys Lys Ile Glu Pro Arg Gly Pro Thr
        210                 215                 220
```

```
Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
                260                 265                 270

Asp Asp Pro Asp Val Gln Ile Ser Trp Phe Val Asn Asn Val Glu Val
            275                 280                 285

His Thr Ala Gln Thr Gln Thr His Arg Glu Asp Tyr Asn Ser Thr Leu
        290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
                340                 345                 350

Tyr Val Leu Pro Pro Pro Glu Glu Glu Met Thr Lys Lys Gln Val Thr
            355                 360                 365

Leu Thr Cys Met Val Thr Asp Phe Met Pro Glu Asp Ile Tyr Val Glu
370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
        435                 440                 445

Pro Gly
    450

<210> SEQ ID NO 56
<211> LENGTH: 213
<212> TYPE: PRT
<213> ORGANISM: Mus musculus

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn His
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Leu
                85                  90                  95

Thr Phe Gly Gly Gly Thr Lys Val Glu Ile Lys Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140
```

```
Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

```
<210> SEQ ID NO 57
<211> LENGTH: 214
<212> TYPE: PRT
<213> ORGANISM: Homo sapiens

<400> SEQUENCE: 57
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn His
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 58
<211> LENGTH: 447
<212> TYPE: PRT
<213> ORGANISM: Homo sapiens

<400> SEQUENCE: 58
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

-continued

Trp Met Gln Trp Ile Arg Gln Ala Pro Gly Gln Gly Leu Glu Trp Ile
            35                  40                  45
Gly Ser Ile Tyr Pro Gly Asp Asp Ala Arg Tyr Thr Gln Lys Phe
 50                  55                  60
Arg Gly Arg Ala Thr Leu Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
            85                  90                  95
Ala Arg Arg Gly Ile Ala Ala Val Val Gly Gly Phe Asp Tyr Trp Gly
                100                 105                 110
Gln Gly Thr Thr Leu Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
                195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly
        435                 440                 445

```
<210> SEQ ID NO 59
<211> LENGTH: 450
<212> TYPE: PRT
<213> ORGANISM: Homo sapiens

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met Gln Trp Ile Arg Gln Ala Pro Gly Gln Gly Leu Glu Trp Ile
            35                  40                  45

Gly Ser Ile Tyr Pro Gly Asp Asp Ala Arg Tyr Thr Gln Lys Phe
        50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
                100                 105                 110

Gln Gly Thr Thr Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 60
<211> LENGTH: 447
<212> TYPE: PRT
<213> ORGANISM: Homo sapiens

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
```

```
                290                 295                 300
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly
                435                 440                 445

<210> SEQ ID NO 61
<211> LENGTH: 443
<212> TYPE: PRT
<213> ORGANISM: Homo sapiens

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Trp Met Gln Trp Ile Arg Gln Ala Pro Gly Gln Gly Leu Glu Trp Ile
            35                  40                  45

Gly Ala Ile Tyr Pro Gly Asp Asp Ala Arg Tyr Thr Gln Lys Phe
50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Phe Asp Tyr Trp Gly
                100                 105                 110

Gln Gly Thr Thr Leu Thr Val Ser Ser Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220
```

```
Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 62
<211> LENGTH: 447
<212> TYPE: PRT
<213> ORGANISM: Homo sapiens

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met Gln Trp Ile Arg Gln Ala Pro Gly Gln Gly Leu Glu Trp Ile
            35                  40                  45

Gly Ser Ile Tyr Pro Gly Asp Asp Ala Arg Tyr Thr Gln Lys Phe
        50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Gly Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160
```

-continued

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu Ala Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Glu Gly Asn Val Phe Ser Cys Ser Val Met His Glu Ala
            420                 425                 430

Leu His Asn Gln Tyr Thr Gln Lys Ser Leu Ser Leu Ser Leu Gly
            435                 440                 445

<210> SEQ ID NO 63
<211> LENGTH: 447
<212> TYPE: PRT
<213> ORGANISM: Homo sapiens

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Phe
            20                  25                  30

Trp Met Gln Trp Ile Arg Gln Ala Pro Gly Gln Gly Leu Glu Trp Ile
        35                  40                  45

Gly Ala Ile Tyr Pro Gly Asp Asp Ala Arg Val Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys

```
                    85                  90                  95
Ala Arg Arg Gly Ile Ala Ala Val Val Gly Gly Phe Asp Tyr Trp Gly
                100                 105                 110

Gln Gly Thr Thr Leu Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
            420                 425                 430

Leu His Asn Gln Tyr Thr Gln Lys Ser Leu Ser Leu Ser Leu Gly
        435                 440                 445

<210> SEQ ID NO 64
<211> LENGTH: 450
<212> TYPE: PRT
<213> ORGANISM: Homo sapiens

<400> SEQUENCE: 64

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Asp Tyr
            20                  25                  30

Trp Met Gln Trp Ile Arg Gln Ala Pro Gly Gln Gly Leu Glu Trp Ile
        35                  40                  45

Gly Ser Ile Tyr Pro Gly Asp Asp Ala Arg Tyr Thr Gln Lys Phe
    50                  55                  60

Arg Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Ala Ala Val Val Gly Gly Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser

-continued

```
            435                 440                 445
Pro Gly
    450
```

COMPOUNDS BINDING HUMAN CD160 AND USES THEREOF

The present invention relates to a compound which binds specifically to human CD160, having as light chain variable domain (VL) a sequence defined by SEQ ID No: 14 or SEQ ID No: 13, and as heavy chain variable domain (VH) a sequence chosen from SEQ ID No: 11, SEQ ID No: 25, SEQ ID No: 26, SEQ ID No: 27, SEQ ID No: 28, SEQ ID No: 29 and SEQ ID No: 30, fragments thereof or derivatives thereof.

Currently, monoclonal antibodies are used as therapies for treating a variety of pathological conditions, including cancers, autoimmune diseases, chronic inflammatory diseases, transplant rejection, infectious diseases, cardiovascular diseases and certain ocular pathological conditions. There are no fewer than about twenty monoclonal antibodies or some of the fragments thereof on the market, and more than four hundred are in clinical development.

The choice of an antibody as a potential candidate in therapy is therefore of major strategic interest. In particular, the antibody selected must have a good affinity and good specificity for its target, optimal efficacy with regard to its possible toxicity, while at the same time being as non-immunogenic as possible.

Among the existing antibodies which bind specifically to the CD160 receptor is the CL1-R2 antibody. It is the murine monoclonal antibody directed against the human CD160 receptor described in patent EP1776387B1. This CL1-R2 antibody has SEQ ID No: 1 as heavy chain variable domain (VH), and SEQ ID No: 2 as light chain variable domain (VL). It has anti-angiogenic properties and also immunomodulatory properties. However, its administration in human beings is limited, because of its excessive immunogenicity due to a "HAMA response," referring to the development of human anti-murine (mouse) antibodies (HAMA), which (i) would induce, in the end, neutralization (or acceleration of its elimination) of the antibody and thus of its therapeutic effects and (ii) could also induce a potential risk of toxicity (adverse immune reactions such as anaphylaxis or serum diseases).

There is a need to provide compounds, in particular antibodies, that are effective in the treatment of pathological conditions involving a neovascularization, in addition to the current anti-VEGF treatments that are available involving inhibitors of Vascular Endothelial Growth Factor (VEGF).

Indeed, angiogenesis which is the formation of new blood vessels from the preexisting vasculature, occurs physiologically. However, it also plays a role in various pathologies as corneal-retinal neovascular diseases with mainly ischaemic retinopathies (IR) or choroidal ones such as exudative or "wet" age-related macular degeneration (wAMD). Together, they constitute the first cause of moderate and severe vision loss in developed countries.

Increasing knowledge of angiogenesis and its etiology in wAMD and IR has led to the development of drugs that target the VEGF pathway. Intravitreal (IVT) injections of anti-VEGF therapeutic agents have emerged over the past decade as the first-line treatments in wAMD, retinal vein occlusion (RVO) and macular edema (DME).

Even though anti-VEGF therapy appears safe in the general population, several limitations related to efficacy and safety have clearly emerged: frequent IVT injections are often required to reach full efficacy; the prolonged use of anti-VEGF leads to a reduction of long-term efficacy, linked to tachyphylaxis or tolerance phenomenon. More than 30% of wAMD patients still poorly respond and thus are resistant to anti-VEGFs. Furthermore, local and systemic adverse effects such as increased risk of elevation of blood pressure, stroke, and myocardial infarctions after repeated administrations of anti-VEGFs have been reported in patients with wAMD.

These limitations underline the need to improve the sustain delivery approaches for anti-VEGFs without increasing the rate of tolerability or safety issues as well as reducing the number of injections. The increase of the rate of patient response is critical to address the large population of poor or no responders. There is therefore a pressing need to develop VEGF-independent complementary and synergistic therapies that inhibit pathological neovascularization while having little or no effect on normal mature tissue vasculature.

These compounds will have to have good biological activity and specific affinity for their targets, while at the same time being well-tolerated and in particular non-immunogenic in human beings.

There is also a need for new agents which can be combined with the current treatments, in particular for stimulating effector immune cells such as NK cells and/or by lifting the anergy of cytotoxic T cells.

The present invention makes it possible to solve these problems. A subject of the present invention is a compound which binds specifically to human CD160 and has as light chain variable domain (VL) a chosen sequence defined by SEQ ID No: 14 or SEQ ID No: 13 and as heavy chain variable domain (VH) a sequence chosen from SEQ ID No: 11, SEQ ID No: 25, SEQ ID No: 26, SEQ ID No: 27, SEQ ID No: 28, SEQ ID No: 29 and SEQ ID No: 30, and the fragments or derivatives of said compound. The compounds of the invention are specifically suitable for administration in human beings in whom they are well-tolerated and non-immunogenic.

The compounds of the invention can take the form of an antibody and more particularly of a monoclonal antibody, of fragments or of derivatives, and are capable of binding to human CD160, with very good affinity.

It has been discovered that the compounds according to the invention exhibit a much better affinity on recombinant CD160 protein and on CD160 positive cells than the parental CL1-R2 antibody or its recombinant chimeric version with same variable regions and human constant regions. This is very advantageous, since the chimeric version which could be compatible with an administration in human beings, still exhibits a certain amount of potential immunogenicity. In addition, such antibodies and the fragments and derivatives thereof have excellent activity.

This is evidenced in the following examples, and particular in Example 1, where the affinity measurements clearly show, unexpectedly, that the H7, in the IgG1 and IgG4 formats, has a much better affinity for human CD160 than the murine CL1-R2 and its respective chimeric human IgG1 and IgG4 forms. The gain in $K_D$ (see Example 1, Table 1, column 8, $K_D$ gain) compared to the parental CL1-R2 anti-CD160 $K_D$ is about 3.75 and 3.34 for H7 in the human IgG1 and IgG4 format respectively. For one and the same concentration of 50 nM of antibody, a better response for the H7 IgG1 than for H7 IgG4 and CL1-R2 and a worse response for the two anti-CD160s in the chimeric formats were also obtained (see Example 1, Table 1, column 9).

Furthermore, as described in Example 8, all the compounds according to the invention have a very different elimination profile in the bloodstream compared to CL1-R2 and to a representative human IgG1, the bevacizumab, with a faster clearance in the serum as measured by systemic pharmacokinetic parameters in rabbit.

The term "human CD160" is intended to mean the human CD160 receptor. It is a 27 kDa receptor which recognizes conventional HLA molecules (HLA A and C) and non-conventional HLA molecules (HLA G) and HVEM (Herpes virus entry mediator), anchored to the cell membrane by a Glycosylphatidylinositol (GPI) motif and belonging to the immunoglobulin superfamily (presence of an immunoglobulin like domain). This protein is further named CD160 GPI. This protein is physiologically expressed by immune cells: NK $CD56^{dim}$ $CD16^{bright}$, T CD8 subset, T gamma-delta and T CD4 cells subset. CD160 is also upregulated in pathological conditions on B cells in hematological cancer as B-CLL or on activated endothelial cells in neovascular ocular pathologies. The cDNA of human CD160 corresponds to the sequence SEQ ID No: 1 described in WO 98/21240. The mRNA of human CD160 is available in Genbank under accession number AF060981. The protein sequence of human CD160 corresponds to the sequence SEQ ID No: 2 described in WO 98/21240, and is available under accession number AAC72302 in Genbank.

It should be noted that CD160 protein exists also on another isoform with a transmembrane (TM) domain hereafter designated as CD160 TM. The protein sequence of the CD160 GPI isoform protein is 100% homolog with the 76.5% first N terminal part of the CD160 TM isoform protein sequence. The cDNA of human CD160 TM isoform is described in WO 2008/155363. The mRNA of human CD160 is available in Genbank under accession number EU016100.1. The protein sequence of human CD160 TM is available under accession number ABV89736.1 in Genbank.

BY55 commercial anti CD160 IgM and CL1-R2 are specific of the CD160 GPI form and are not able to recognize the CD160 TM isoform as respectively described in (Giustiniani et al, 2009) and (El-Far et al, 2014). In prior art, there is no anti-CD160 mAb described to recognize both isoforms of CD160.

It is another advantageous feature of the compounds according to the invention that they are able to recognize both isoforms of CD160 (the TM and the GPI) while the parental CL1-R2 antibody is not and this is to broaden indications when these two isoforms are present on the same cells (like for example very in the T and NK lymphomas)

In the context of the present invention, the term "variable region" or "variable domain" of a compound is intended to mean a region or domain which relates to the amino-terminal domains of the heavy or light chain of an antibody. The heavy chain variable domain can be referred to as "VH". The light chain variable domain can be referred to as "VL". These domains are generally the most variable parts of an antibody and contain the antigen-binding sites. This compound can take the form of an antibody, in particular a monoclonal antibody.

A light or heavy chain variable region (VL or VH) consists of a "framework region" interrupted by three hypervariable regions called "complementarity-determining regions" or "CDRs".

All of the 6 CDRs enable the binding of the antibody to its target antigen. For example, the CL1-R2 antibody has, as CDRs, the sequences SEQ ID Nos: 3 to 8 in accordance with the AbM CDR terminology (broader and adapted to antibody affinity maturation technologies). These CDRs are present in the compounds H7 of the present invention.

The compounds according to the invention have excellent affinity for their target, human CD160, which is greater than that of CL1-R2 or than a chimeric form of this CL1-R2 (cf. Example 1).

Preferably, the compound of the invention has the sequence SEQ ID No: 11 as heavy chain variable domain (VH), and the sequence SEQ ID No: 14 as light chain variable domain (VL). Such an antibody corresponds in particular to the "H7" antibody mentioned in Example 1.

Variants of the H7 antibody have been obtained as described in example 2.

In another implementation of the invention, the compound has the sequence SEQ ID No: 25 as heavy chain variable domain (VH), and the sequence SEQ ID No: 14 as light chain variable domain (VL). Such a compound corresponds in particular to the "F04" antibody.

In another implementation of the invention, the compound has the sequence SEQ ID No: 26 as heavy chain variable domain (VH), and the sequence SEQ ID No: 14 as light chain variable domain (VL). Such a compound corresponds in particular to the "D09" antibody.

In another implementation of the invention, the compound has the sequence SEQ ID No: 27 as heavy chain variable domain (VH), and the sequence SEQ ID No: 14 as light chain variable domain (VL). Such a compound corresponds in particular to the "A12" antibody.

In another implementation of the invention, the compound has the sequence SEQ ID No: 28 as heavy chain variable domain (VH), and the sequence SEQ ID No: 14 as light chain variable domain (VL). Such a compound corresponds in particular to the "G05" antibody.

In another implementation of the invention, the compound has the sequence SEQ ID No: 29 as heavy chain variable domain (VH), and the sequence SEQ ID No: 14 as light chain variable domain (VL). Such a compound corresponds in particular to the "D12" antibody.

In another implementation of the invention, the compound has the sequence SEQ ID No: 30 as heavy chain variable domain (VH), and the sequence SEQ ID No: 14 as light chain variable domain (VL). Such a compound corresponds in particular to the "A09" antibody.

In one particular implementation of the invention, the compound is a monoclonal antibody targeting human CD160, which preferably has, as constant region, a constant region of an immunoglobulin (IgG), preferably of IgG1 or of IgG4.

The term "constant domain" or "constant region" as defined herein is intended to mean a constant region derived from an antibody which is encoded by one of the heavy or light chain immunoglobulin constant region genes.

The term "constant light chain" or "light chain constant region", as used in the context of the present invention, is intended to mean the region of an antibody encoded by the kappa (Ckappa) or lambda (Clambda) light chains. The constant light chain typically comprises a unique domain and, as defined herein, refers to positions 108-214 of Ckappa, or Clambda, where the numbering is according to the EU index (Kabat et al., 1991).

The term "constant heavy chain" or "heavy chain constant region" is intended to mean herein the region of an antibody encoded by the mu, delta, gamma, alpha or epsilon genes in order to define the isotype as the antibody as IgM, IgD, IgG, IgA or IgE, respectively. For full-length IgG antibodies, the constant heavy chain, as defined herein, refers to the N-terminal end of the CH1 domain to the C-terminal end of the CH3 domain, thus comprising positions 118-447, where the numbering is according to the EU index.

Preferably, the constant region of the compound targeting human CD160 according to the invention is a constant region of IgG. It can be chosen from the constant regions of IgG1, IgG2, IgG3 and IgG4.

Preferably, the constant region of the compound targeting human CD160 according to the invention is a constant region of IgG1 (SEQ ID No: 16), or IgG1 E345K (SEQ ID No: 43) or E430G (SEQ ID No: 44) for indications in oncology, or of IgG4 S228P/R409K (SEQ ID No: 15) or IgG4-(S228P/R409K)+L235E (SEQ ID No: 31) or IgG1 N297Q or else the variants IgG4-(S228P/R409K)+H310A/H435Q (SEQ ID No: 32), IgG4-(S228P/R409K)+I253A (SEQ ID No: 33), IgG1-(N297Q)+H310A/H435Q (SEQ ID No: 34) and IgG1-(N297Q)+I253A (SEQ ID No: 35) and the aglycosylated mutants thereof for ophthalmology.

The IgG4 subclass and its variants has very low affinity for the effectors involved in the complement cascade and Fc gamma receptors (or FcR including FcgRIIa, FcgRIIIa and FcgRI), which makes it advantageous in the case where the CDC (complement-dependent cytotoxicity) effect and/or the ADCC (antibody-dependent cell-mediated cytotoxicity) effect and/or the ADCP the (antibody dependent cell phagocytosis) is/are not desired and where it is desired to limit the possible risks of toxicity at the antibody obtained.

Conversely, the IgG1 subclass and its variants are responsible for strong ADCC and/or CDC activity and/or ADCP, which makes them advantageous for increasing the cytolysis of target cells, but with a greater risk of toxicity.

In one implementation of the invention, the compound is a monoclonal antibody targeting human CD160, having as light chain constant domain a sequence chosen from SEQ ID No: 22 (Km3 polymorphism corresponds to Ala153/Val191), SEQ ID No: 23 (Km1 polymorphism corresponds to Val153/Leu191) and SEQ ID No: 24 (Km1,2 polymorphism corresponds to Ala153/Leu191), and as heavy chain constant region a sequence chosen from SEQ ID No: 15, SEQ ID No: 16, SEQ ID No: 31, SEQ ID No: 32, SEQ ID No: 33, SEQ ID No: 34 and SEQ ID No: 35, and the aglycosylated mutants thereof.

More preferentially, the compound according to the invention targeting human CD160 has as heavy chain constant domain a sequence chosen from SEQ ID No: 15, SEQ ID No: 16, SEQ ID No: 31, SEQ ID No: 32, SEQ ID No: 33, SEQ ID No: 34, SEQ ID No: 35, and the aglycosylated mutants thereof, and as light chain constant domain the sequence SEQ ID No: 22.

A compound according to the invention can be monospecific or monofunctional for CD160, while being monovalent (a single antigen-binding site, in the case in point human CD160), or while being multivalent (at least 2 sites for binding to human CD160).

A compound according to the invention can also be a multispecific compound, for example: a bispecific antibody (bsab) or a similar molecule. The multispecific compounds are compounds which have binding specificities for at least two different epitopes, which are typically non-overlapping. These epitopes can be on identical or different targets. If the epitopes are on different targets, these targets can be on the same cell or on different cells or different cell types. In certain embodiments, one of these binding specificities is CD160, in particular the extracellular domain of human CD160, and the other is for another antigen.

A multispecific compound according to the invention can take the form of bispecific antibodies in the IgG format (i.e. bsab, orthogonal Fabs, strand exchange engineered domain SEED or Seed-body), of IgGs with Fabs or ScFvs fragments added (i.g.: DVD Igs, Dual domain double head antibodies, Di-diabodies, Affibodies, Biomunex, Fynomab), of bsabs based on antibody fragments (e.g. bispecific antibody fragments, Fv dimers, BITEs, ImmTACS, DART, BIKEs), of trispecific antibodies, of bsabs based on fusion proteins (e.g. scFV-fusions BsAb), of aggregated antibodies, etc.

The epitopes targeted by the multispecific compounds (i.e. which are capable of binding specifically to CD160 and to at least one antigen other than CD160) or targeted by the antibody different from the compound according to the invention and present in a composition according to the invention can be present in the following antigens which are targets of which the activation or neutralization may have key roles in the inhibition of angiogenesis or of inflammation associated with this angiogenesis process, such as the following molecules: VEGF (VEGF-A, VEGF-B, VEGF-C or VEGF-D) and also PlGF (placental growth factor), VEGF-R2, angiopoietin 2; angiopoietin like 4, CD200, CD200R, PDGFs (PDGF-AA, PDGF-B, PDGF-BB, PDGF-CC or PDGF-DD), PDGF-Rs, FGFs such as FGF2 or FGF beta, beta-amyloid, sphingosine-1-phosphate (S1P), C'5, IL6, MER TK, CD115, TNF alpha, IL8, HGF, TGF beta, IGF1, IL1, IL2, EGF, KGF, G-CSF, GM-CSF, alpha-v,beta-3 and alpha-v,beta-5 integrins, transmembrane and soluble CD146; metalloproteases (such as MMP 1, 2 and 9 and MT1-MMP); TIMP-2; angiogenin; endothelial cell growth factor (PD-ECGF); platelet activation factor; prostaglandin E; pleiotropin or the class II MHCs, HP59 or CM101; or targets of which the activation or neutralization may have key roles in the re-activation of T lymphocytes, the immunosuppression of which correlates with a poor prognosis and a progression of cancer, such as the following molecules: CD3, CD25, CD28, CD40, PD1, CTLA4, 4-1BB, LAG-3 or ICOS, or molecules of which the targeting would make it possible to get close to the key players of the immune system of CD160-positive cells, such as the following molecules: CD16, CD3, CD47, or else molecules of which the targeting would reinforce the specificity of the bsabs antibody for B lymphomas, such as the following molecules: CD20, CD19, CD5, CD200 for CLLs, CD180 for marginal zone lymphomas (MZL) and CD148 for mantle cell lymphomas, or else antigens which make it possible to increase the stability and the pharmacokinetics of scFv, Fab or any other derivative, such as human serum albumin (HSA), CD180, CD200, CD40, CD20, CD37, CD38, CD148, CD180 and any other antigen specific for B lymphomas.

The terms "fragments" and "derivatives" of a compound targeting human CD160 according to the invention are intended to mean respectively fragments and derivatives which have retained the binding affinity and the specificity of said compound for human CD160. Such fragments and derivatives are functional equivalents of said compound. They bind substantially to the same epitope as said compound, and/or can compete with said compound for binding to human CD160, and they retain the binding specificity to human CD160, which is sufficient for the fragments or derivatives not to bind to HLA receptors other than human CD160.

The "fragments" and "derivatives" according to the invention have an affinity similar to the compound of the invention for CD160.

The term "fragment" of a compound targeting human CD160 according to the invention is intended to mean preferably a format such as a Fab, a Fab' (reduction of a F(ab')2, for example with beta-mercaptoethanol), a F(ab')2 or a heavy-chain or light-chain fragment. The fragments targeting human CD160 according to the invention comprise at least one heavy chain variable domain (VH) and/or one light chain variable domain (VL) as defined above.

In one particular implementation of the invention, the compound is a fragment comprising a light chain (VL)

defined by SEQ ID No: 57 and a heavy chain comprising a sequence chosen from SEQ ID No: 36, SEQ ID No: 37 and SEQ ID No: 38.

The term "derivative" of a compound targeting human CD160 according to the invention is intended to mean a format of this compound comprising at least one heavy chain variable domain (VH) and/or one light chain variable domain (VL), fused to at least one sequence that is different from the natural sequence (for example a linker such as SEQ ID No: 39 or a sequence of another protein, in particular a receptor or a fragment thereof). Said derivative has a binding affinity to human CD160 that is comparable to that of the whole compound according to the invention, and also a binding specificity to human CD160 that is comparable to that of said compound. In the context of the invention, the term "comparable" means that the binding affinity or binding specificity can vary within a limit of 25%. The derivatives can be obtained according to the general knowledge of those skilled in the art, by enzymatic reaction, synthesis and/or genetic engineering.

In one particular implementation of the invention, the compound is a fragment comprising a light chain (VL) defined by SEQ ID No: 57 and a heavy chain comprising a sequence chosen from SEQ ID No: 40 or SEQ ID No: 41.

A derivative according to the invention can be monovalent (a single site for binding to an antigen, in the case in point human CD160) or multivalent (at least 2 sites for binding to an antigen or to several antigens, including at least human CD160). Preferred multivalent derivatives include bivalent, trivalent and tetravalent derivatives.

In one embodiment of the invention, the derivative according to the invention is a multispecific or multifunctional compound, for example a bispecific antibody (bsab) or a similar molecule, the epitopes of which can be on identical or different targets. In one embodiment, the bispecific antibodies can bind to two different epitopes of CD160. In another embodiment, the bispecific antibodies can bind to an epitope of CD160 and an epitope of an antigen other than CD160. The epitopes of interest have been described above in the present description.

The "single-stranded Fv" or "scFv" antibody derivatives comprise the VH and VL domains of the antibody, these domains being present in a single polypeptide chain.

Another derivative according to the invention is a monospecific multivalent scFv, which can be obtained by binding at least two monovalent derivatives to one another. The binding may be covalent or non-covalent. The presence of several CD160-binding sites increases the binding capacity to this antigen.

Another derivative according to the invention is a multispecific multivalent scFv.

Among the other derivatives, mention may be made of "diabodies" which denote small antibody derivatives with two antigen-binding sites, said fragments comprising a heavy chain variable domain (VH) linked to a light chain variable domain (VL) in the same polypeptide chain (VH and VL). The multivalent scFvs are preferably chosen from diabodies (which are bivalent and are composed of 2 scFvs), triabodies (which are trivalent and are composed of 3 scFvs) and tetrameric scFvs.

Another multivalent derivative according to the invention is a dimer, each monomer comprising an scFv bonded to a heavy chain fragment, for example to a CH3 fragment; this corresponds to a minibody. The 2 scFvs present in the minibody can be identical (the minibody is then monospecific, since it binds only to human CD160) or different (the minibody is then bispecific, since it binds, on the one hand, to human CD160, but also to another antigen).

Another multivalent derivative according to the invention is also a dimer, each monomer comprising an scFv bonded to heavy chain fragments, for example to the CH2 and CH3 fragments. Once again, the 2 scFvs present may be identical or different. In the latter case, they are referred to as bispecific antibodies.

Another multivalent derivative according to the invention is an antibody fragment consisting of a single monomeric heavy chain variable domain. This corresponds to a single-domain antibody (VHH or sdAb, called Nanobody by Ablynx).

As an example of tetravalent monospecific anti-CD160 derivatives, mention may also be made of the anti-CD160 molecule in which, upstream of each variable region of the heavy chain, the VH and CH1 regions are duplicated as described in SEQ ID No: 42 in example 3. It is then possible to co-express, in mammalian cells, the genes encoding SEQ ID No: 42 and the anti-CD160 light chain defined by SEQ ID No: 57 in order to obtain a functional version of functional monospecific tetravalent anti-CD160.

Another derivative according to the invention is obtained by recombinantly generating an IgM using one of the chimeric murine light chain/heavy chain binding human CD160 pairs, according to the invention.

In another embodiment, a subject of the invention is a composition comprising at least one compound according to the invention. In one particular implementation, the composition comprises at least one compound according to the invention and at least one antibody other than the compound according to the invention.

In one implementation of the invention, the compound or the composition as described above is used as a medicament.

The compound targeting human CD160 according to the invention, a fragment thereof and/or a derivative thereof can be present in a pharmaceutical composition or a medicament. This pharmaceutical composition preferably comprises a pharmaceutically acceptable carrier. The term "pharmaceutically acceptable" refers to a non-toxic material which is compatible with a biological system such as a cell, a cell culture, a tissue or an organism, and which does not interfere with the efficacy of the biological activity of the active ingredients of the composition. The characteristics of the carrier will depend on the method of administration.

The pharmaceutical composition or medicament can be in any form that can be administered to a patient, and includes in particular solutions, suspensions, lyophilized powders, capsules and tablets.

The pharmaceutical composition or medicament can be in a form that is compatible with an injection, i.e. a local injection, i.e. an intravitreal injection, an administration through the mucosa, an inhalation, an oral administration and more generally any formulation suitable for the intended purpose.

A subject of the present invention is also a product comprising a compound as described in the present application and an antibody which binds specifically to at least one other antigen which may be identical to or different from CD160 (in particular to one of the epitopes of the antigens described above), for simultaneous, separate or sequential use in the treatment and/or prevention of a pathological condition which causes a neovascularization, in particular chosen from neovascular ocular pathological conditions, primary diabetic retinopathy or age-related macular degeneration (ARMD), diabetes, diabetic blindness, rheumatoid arthritis, pre-eclampsia, eclampsia or cancers.

The term "preventing a pathological condition" is intended to mean the prevention of the occurrence of this disease in a subject, in particular a human being, in whom the disease has not yet appeared.

The term "treating a pathological condition" is intended to mean the inhibition of this disease, i.e. the arrest of its development, its regression, or the disappearance of the symptoms and consequences of the disease, or else the disappearance of the causes of the disease.

More preferentially, the compound according to the invention or the composition according to the invention is used as an anti-angiogenic, immunomodulator and/or cytotoxic agent.

A subject of the invention is more particularly a compound according to the invention, for use thereof as an anti-angiogenic.

In the context of the present invention, an "anti-angiogenic agent" or "angiogenesis inhibitor" denotes a compound which inhibits angiogenesis, vasculogenesis, or else unwanted vascular permeability, either directly or indirectly.

Preferably, the compound according to the invention can be used for preventing and/or treating neovascular pathological conditions, preferably neovascular ocular pathological conditions, diabetes, diabetic blindness, primary diabetic retinopathy or age-related macular degeneration, rheumatoid arthritis, pre-eclampsia, eclampsia or cancers.

The term "neovascular ocular pathological conditions" is intended to mean all the neovascular ocular diseases or disorders. Several ocular disorders are associated with pathological angiogenesis. For example, the development of ARMD is associated with a process called choroidal neovascularization (CNV). Diabetic macular edema (DME) is another ocular disorder with an angiogenic component. DME is the most widespread cause of moderate sight loss in patients suffering from diabetes and is a common complication of diabetic retinopathy, a disease affecting the blood cells of the retina.

Another ocular disorder associated with abnormal angiogenesis is central retinal vein occlusion (CRVO). CRVO is caused by the obstruction of the central retinal vein which results in an accumulation of blood and fluid in the retina. The retina can also become ischaemic, leading to the growth of inappropriate new blood vessels that can cause additional sight loss and more serious complications.

Mention may also be made, but non-exhaustively, of other neovascular ocular pathological conditions, in particular chosen from Norrie disease; all forms of choroidal neovascularizations, polypoidal retinochoroidal vasculopathies, retrofoveolar choroidal neovessels associated with myopia and Sorsby's dystrophia; uveal melanomas; and rubeosis iridis and neovascular glaucoma, retinal angiomatous proliferation (RAP), neovascularizations occurring following corneal transplant complications and/or corneal infections and/or corneal attacks by the environment, chosen from pathogenic infections and chemical burns; or all forms of retinopathies, including diabetic and oedematous ischaemias, premature diabetic retinopathy, proliferative and non-proliferative forms of retinopathies, cystoid macular edema, all forms of age-related macular degeneration (ARMD), in particular the wet form, all vitelliform macular degenerations, including Best's disease; ocular angiomas such as Von Hippel-Lindau disease; Eales disease; Coast disease.

The term "diabetes" is intended to mean any type of diabetes, in particular sugar diabetes (in relation to insulin) and diabetes insipidus (in relation to antidiuretic hormone). Among the forms of sugar diabetes, mention may be made of type 1 diabetes (insulin dependent), type 2 diabetes (decrease in insulin sensitivity), gestational diabetes or neonatal diabetes. Among the forms of diabetes insipidus, mention may be made of central diabetes, due to a low synthesis of antidiuretic hormone by the pituitary gland, or peripheral diabetes, due to a low sensitivity of the kidney to antidiuretic hormone.

The term "cancers" is intended to mean any abnormal proliferation of cells. The cancers are in particular chosen from breast cancers, colorectal cancer, bladder cancer, lung cancer and prostate cancer.

An anti-angiogenic compound of the invention could be used in particular in the treatment of cancers where the neovascularization component is an important vector of the propagation of the disease. Mention is in particular made of breast cancer, colorectal cancer, non-small-cell lung cancer, non-Hodgkin's lymphoma, urogenital tumours, such as kidney cancer, prostate cancer, bladder cancer or renal carcinoma, colon cancer, Hodgkin's lymphoma, liver cancer, cervical cancer, melanoma, ovarian cancer, mesothelioma and glioblastoma.

In one particular implementation, the compound of the invention can be used as a cytotoxic agent.

A "cytotoxic antibody" or "cytotoxic agent" or "anti-tumour agent" denotes a therapeutic monoclonal antibody (mAb), or a fragment or a derivative thereof, which induces antibody-dependent effector cell-mediated cytotoxicity (ADCC), or else complement-dependent cytotoxicity, or else antibody-dependent cell-mediated phagocytosis (ADCP) and the direct induction of apoptosis in tumour cells.

Another derivative according to the invention is a compound with improved cytotoxic activity. A compound with improved cytotoxic activity can be obtained by grafting the variable chains of anti-CD160s onto IgG formats with optimized glycosylations of Fc regions (for example a defucosylation) or by modifying by engineering the amino acid sequence of the Fc of the antibody of interest, for example by introducing the DLE triple mutant (S293D/A330L/I332E). Such a compound can also be obtained by generating a format of the compound according to the Hexabody format, or else BITE or alternatively BiKE format (with one valency directed against CD160 and a second valency directed against CD16) or TriKE format. Examples of these improvements are mentioned in Example 03 of this invention. It is also possible to create compounds of the invention in which one or more residues of an antibody are replaced with cysteine residues and the free thiol groups can be used so as to create therapeutic agents such as immunotoxins, radioimmunoconjugates or else ADCs (Antibody-Drug Conjugates).

In another bivalent bispecific compound of the invention, it is also possible to use CD160 as a replacement for CD16 as valency in an antibody which involves NK cells, on the one hand, and a tumour antigen on the other non-CD160 valency. This is because CD160 is also an activator receptor expressed on natural NK cells (see Examples 15 and 16 of this invention). The interaction of this compound with the CD160 of NK cells would then result in activating the NK cells and also bringing these effector cells close to their tumour target.

Another derivative according to the invention is a compound with an improved systemic half-life in order to improve its cytotoxic activity.

The compound or the composition according to the invention can be used for the treatment of haematological cancers or solid tumours. Examples of cytotoxic compounds according to the invention are presented in Examples 3 and 4.

It is known that CD160 is an antigen specific for certain tumour cells, in particular in the majority of B-cell chronic lymphoid leukaemias (B-CLL and also hairy cell leukaemias (HCL)), and with a more heterogeneous expression as a function of patients in cases of marginal zone lymphomas and in mantle cell lymphomas. However, CD160 is an antigen which is not at all expressed on normal circulating B cells. Anti-CD160 antibodies can therefore be used to specifically kill or inhibit the tumour growth of these B lymphomas.

The compound of the invention can therefore be used in the treatment of haematological cancers, in particular chronic lymphoid leukaemia (CLL), hairy cell leukaemia, acute myeloid leukaemia (AML), multiple myeloma (MM), or in the treatment of solid tumours, in particular melanoma, renal carcinoma, lung cancer and in particular epidermoid lung cancer, neuroblastoma, ovarian carcinoma, breast cancer, gastric cancer.

The compound of the invention can also be used in the treatment of haematological cancers in combination with at least one other antibody, such as anti-CD20 antibodies, in particular rituximab, ofatumumab, obinutuzumab, ocaratuzumab, or veltuzumab, anti-CD37 antibodies, anti-CD38 antibodies or anti-CD40 antibodies.

The anti-CD160 compound of the invention can be used for modulating the immunomodulatory activity of CD160 on the NK and T cells of immunity in the treatment of cancers that respond favourably to immune checkpoint inhibitors, in particular melanoma, non-small-cell lung cancer, urogenital tumours such as bladder cancers or renal carcinoma, colon cancer, Hodgkin's lymphoma, or breast cancer.

The term "immunomodulatory CD160 activity" denotes one or more immunoregulatory activities associated with CD160.

The terms "modulate" and "immunomodulator" and their related terms refer to a reduction or to an increase in the activity of CD160 associated with an upregulation of T-lymphocyte or NK-cell responses due to its interaction with an anti-CD160 antibody, where the increase is relative to the activity of CD160 in the absence of the same antibody. A reduction or an increase in activity is preferably by at least approximately 10%, 20%, 30%, 40%, 50%, 60%, 70%, 80%, 90% or more. When the CD160 activity is reduced, the terms "modulator" and "modulate" are interchangeable with the terms "inhibitor" and "inhibit". When the CD160 activity is increased, the terms "modulator" and "modulate" are interchangeable with the terms "activator" and "activate".

The activity of CD160 can be determined quantitatively using measurements of NK activity (by assaying a marker such as CD69) or of secretion of cytokines such as IFN gamma as described respectively in Examples 14 and 15. The activity of CD160 can also be determined using assessment of T-cell activity by measurement of proliferation, of cytokine secretion or of activation marker as CD69 as described in example 19.

The combination of immunomodulators will be key for improving the clinical responses to immune checkpoint inhibitors.

Thus, in one particular embodiment, the compounds of the invention are combined with one of these immunomodulators, preferentially with an anti-PD-1, an anti-CTLA-4 or an anti-PD-L1, in a composition, where said composition is used as an immunomodulator.

In another particular embodiment of the invention, the anti-CD160 compound is used as an immunomodulator for the treatment of bacterial infections for stimulating the defense against pathogenic bacteria which infect the intestines (in particular *Escherichia coli, Clostridium difficile*) or the lungs (in particular *Streptococcus pneumoniae*) by activating intra-epithelial innate lymphoid cells expressing CD160.

A subject of the invention is also a nucleic acid encoding a compound according to the invention, or a fragment thereof or a derivative thereof. The term "nucleic acid" is intended to mean a DNA, cDNA or RNA sequence.

Another subject of the invention is an expression vector comprising said nucleic acid, or an expression cassette comprising said nucleic acid. According to the invention, the appropriate expression vectors can comprise at least one expression control element functionally linked to the nucleic acid. The expression control elements are inserted into the vector and make it possible to regulate the expression of the nucleic acid.

Another subject of the invention is a recombinant cell comprising an expression vector as described above, or one or more nucleic acid(s) as described above. According to the invention, examples of cells that can be used are eukaryotic cells, such as animal, plant, insect and yeast cells; and prokaryotic cells, such as *E. coli*. The means by which the vector carrying the gene can be introduced into the cells comprise in particular microinjection, electroporation, transduction or transfection using DEAE-dextran, lipofection, calcium phosphate or other procedures known to those skilled in the art. In one preferred embodiment, the eukaryotic expression vectors which function in eukaryotic cells are used.

Such vectors and nucleic acids can be used in gene or cell therapy, in order to cause the protein of interest to be produced, in the case in point the compound according to the invention, by the host organism.

A subject of the present invention is also a method for treating a subject, preferably a human being, in which a therapeutically effective amount of a compound according to the invention is administered to said subject. The compound according to the invention is thus administered in a therapeutically effective amount. A therapeutically effective amount corresponds to an amount that is sufficient to prevent and/or treat the targeted neovascular pathological condition. This amount can vary with age, sex of the subject and stage of the disease and will be determined by those skilled in the art. A therapeutically effective amount can vary between 0.01 mg/kg and 50 mg/kg, preferably between 0.1 mg/kg and 20 mg/kg, and more preferably between 0.1 mg/kg and 2 mg/kg, in one or more daily administrations, for one or more days.

The method of administration can be by injection or by gradual infusion. The injection can be intravenous, intraperitoneal, intramuscular, subcutaneous, transdermal, subconjunctival, intraocular or intravitreal. For a subconjunctival or intravitreal injection, the therapeutically effective amount of the compound according to the invention can be between 0.1 mg and 10 mg.

The preparations for parenteral administration can include sterile aqueous or non-aqueous solutions, suspensions or emulsions. Examples of non-aqueous solvents are propylene glycol, polyethylene glycol, vegetable oils, such as olive oil, or injectable organic esters such as ethyl oleate. Aqueous carriers comprise water, alcohol/water solutions, emulsions or suspensions. The preparations for parenteral administration can also include sugars and/or salts.

The compound according to the invention can be labelled. Examples of labels include toxins, enzymes, radioisotopes, fluorescent compounds, colloid materials, chemiluminescent compounds, and bioluminescent compounds. The methods for bonding a label to an antibody are well known to those skilled in the art.

Another labelling technique consists in coupling the antibody to low-molecular-weight haptens, it being possible for these haptens to be specifically modified by means of a second reaction. Examples of haptens are biotin, which react with avidin, or dinitrophenol, pyridoxal or fluorescein, which can react with anti-hapten specific antibodies.

The invention is now illustrated by the following examples and the attached figures.

In panel A is reported the impact/incidence of ELB01103 over time (between Day 0 & Day 14 and Day 0 & Day 28) on % of clinically relevant lesions (grade 3+4)/Total Number of spots. The efficacy data at Day 14 and Day 28 are respectively represented as plain black bar and as diagonal black bar. The mean efficacy level of anti VEGF as reported in literature in this model is indicated by a black arrow.

In panel B is reported the impact of ELB01103 on evolution of the leakage severity over time. The evolution of the leakage severity is seen by change over time (Day 14 to Day 28) of grade score of individual clinically relevant ChNV lesion.

In panel C, the impact of dose escalating (0.3 to 3 mg) of ELB01103 on mean change of ChNV area of clinically relevant lesions from Day 14 to Day 28 is described.

In panel D, the impact of a dose of ELB01103 (1 mg) on mean change of retinal thickness of several types of lesions between Day 14 and Day 28 is described. In grey is reported the impact on all lesions (grade 1+2+3+4), in diagonal grey bars is reported the impact on clinically relevant lesions (grade 3+4) and in black is reported the impact when only grade 4 lesions are considered.

Figure 7:
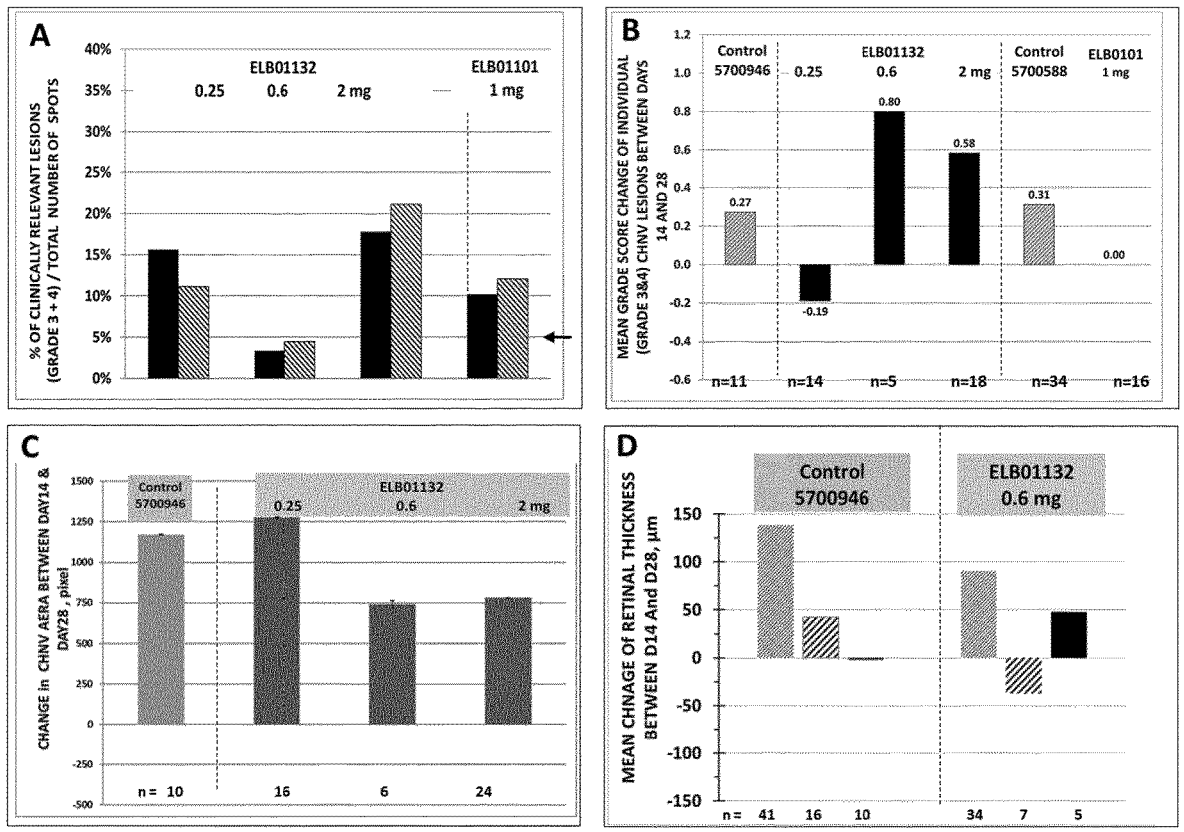

FIG. 7: Summary of dose efficacy data of H7 D12 in the Fab linker Fab format (ELB01132) in the monkey laser induced ChNV model.

In panel A is reported the impact/incidence of ELB01132 over time (between Day 0 & Day 14 and Day 0 & Day 28) on % of clinically relevant lesions (grade 3+4)/Total Number of spots. The efficacy data at Day 14 and Day 28 are respectively represented as plain black bar and as diagonal black bar. The mean efficacy level of anti VEGF as reported in literature in this model is indicated by a black arrow.

In panel B is reported the impact of ELB01132 on evolution of the leakage severity over time. The evolution of the leakage severity is seen by change over time (Day 14 to Day 28) of grade score of individual clinically relevant ChNV lesion.

In panel C, the impact of dose escalating (0.25 to 2 mg) of ELB01132 on mean change of ChNV area of clinically relevant lesions from Day 14 to Day 28 is described.

In panel D, the impact of a dose of ELB01132 (0.6 mg) on mean change of retinal thickness of several types of lesions between Day 14 and Day 28 is described. In grey is reported the impact on all lesions (grade 1+2+3+4), in diagonal grey bars is reported the impact on clinically relevant lesions (grade 3+4) and in black is reported the impact when only grade 4 lesions are considered.

Figure 8:
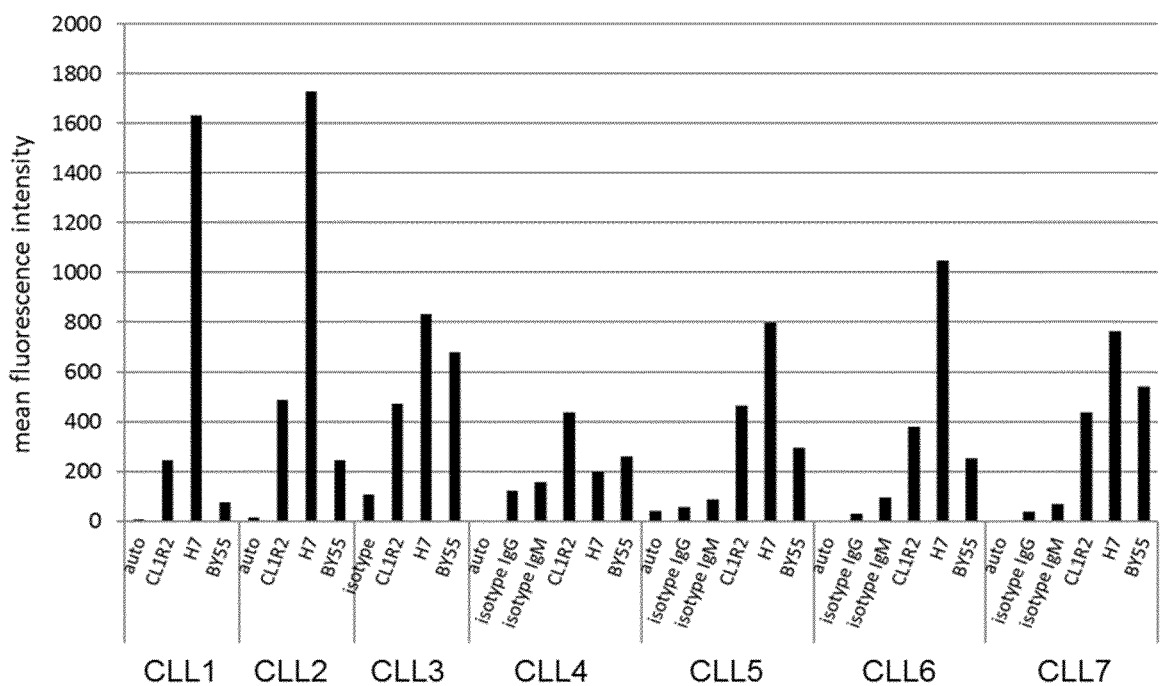

FIG. 8: The anti-CD160 H7 antibody in the IgG1 format recognizes the CD160-positive tumour cells of CLL patients.

Figure 9:
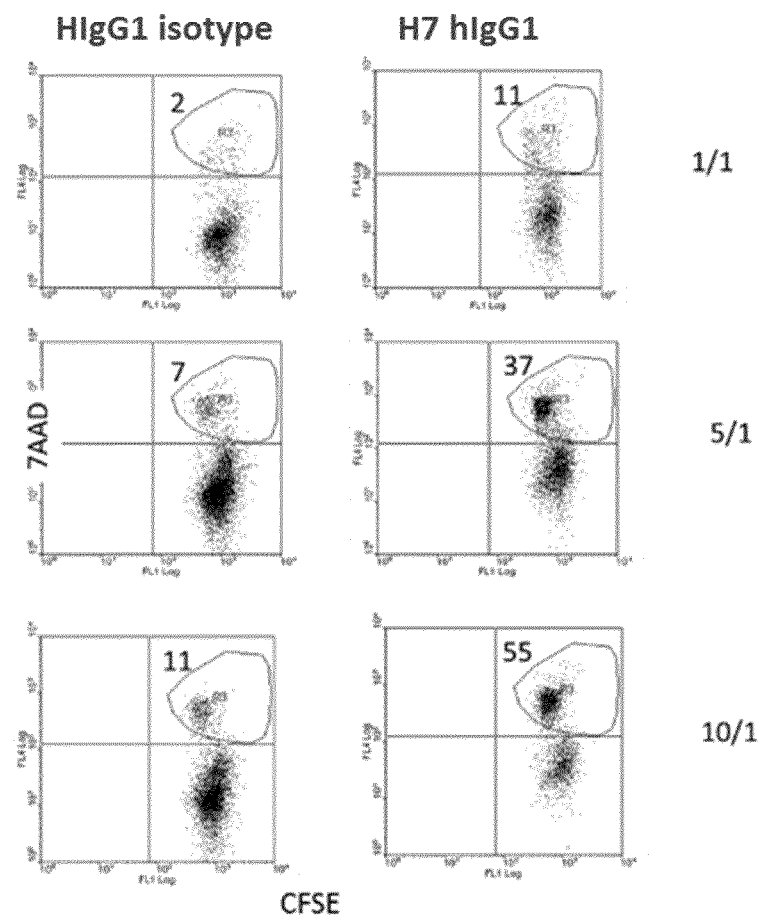

The PBMCs isolated from 7 CLL patients were labelled with the antibodies CL1-R2 (murine anti-CD160 IgG1), anti-CD160 H7 according to the invention in IgG1 format, or BY55 (murine anti-CD160 IgM), in a CD19/CD5/CD3/CD56 panel. The CD5+CD19+ tumour cells were analysed in order to measure the fluorescence intensity of the CD160 labelling. CD160 expression is detectable on all the CLL samples with variable intensities. The H7 IgG1 antibody binds efficiently to the tumour cells in 6/7 of the CLL samples examined.

auto=autofluorescence of the cells; isotype=IgG1 or IgM, murine, irrelevant, negative control FIG. 9: The anti-CD160 H7 antibody in the IgG1 format kills the cells expressing CD160 via an ADCC mechanism.

NK cells purified from the blood of a healthy donor were used as effectors in a test measuring the ADCC activity of the anti-CD160 H7 IgG1 antibody. The E300-CD160 target cells (transfected pre-B human cell line expressing CD160) were labelled with CFSE, and incubated with the effector NK cells in the presence of the H7 IgG1 antibody or of a human IgG1 isotype control, at the effector/target ratios indicated (1/1, 1/5 and 1/10). The percentages of target cells killed were measured by labelling with 7AAD and flow cytometry analysis. The percentages of doubly labelled 7AAD+CFSE+ dead cells are indicated in the top right quadrant on the dot-plots presented.

Figure 10:
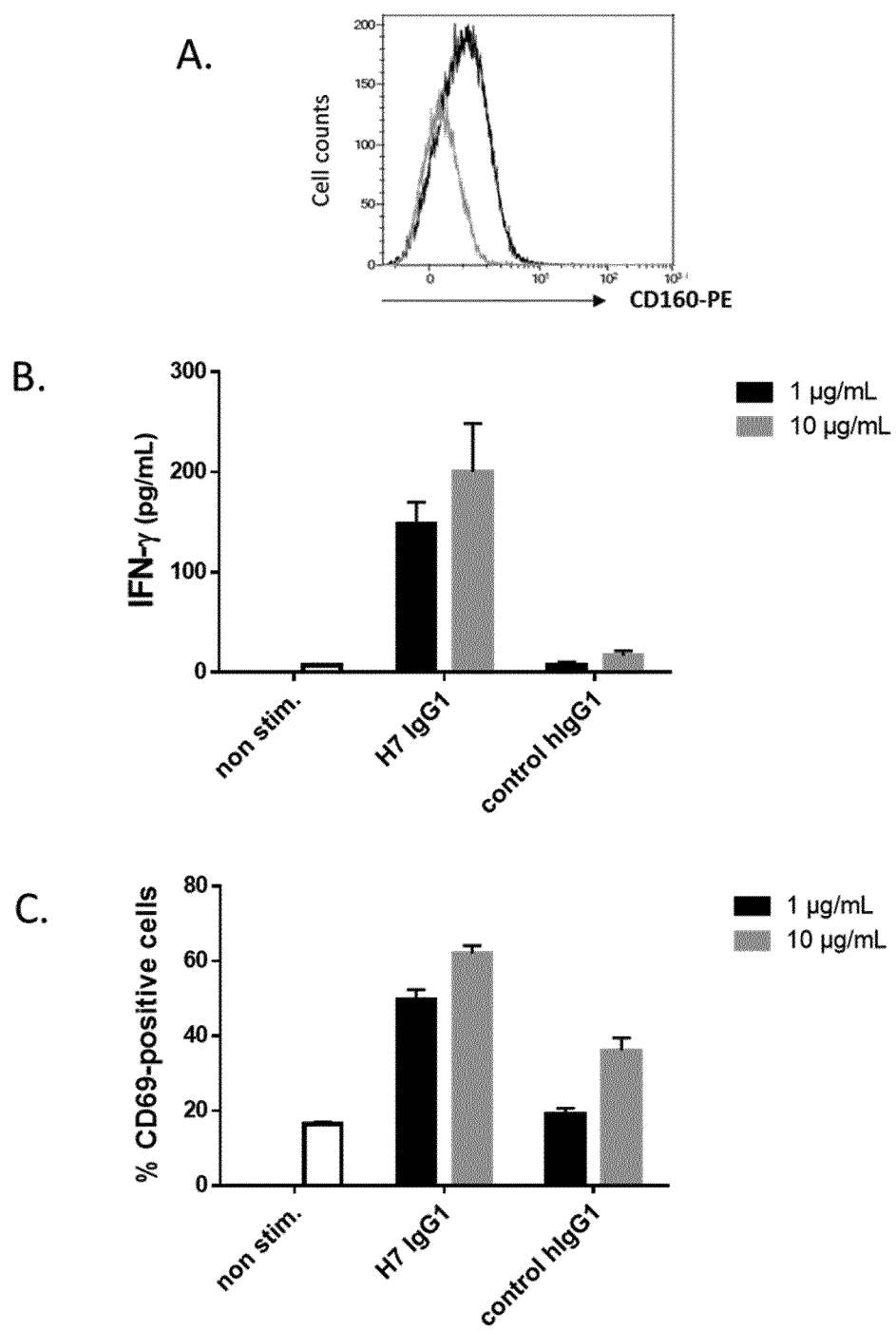

FIG. 10: The anti-CD160 H7 antibody in the IgG1 format activates NK cells.

A) The H7 IgG1 antibody binds to human NK cells. NK cells were purified from the blood of a healthy donor using a Miltenyi kit (ref. 130-092-657) and an autoMACS™ (Miltenyi ref. 130-092-545). After saturation of the cell surface Fc receptors with human IgG Fc fragment (Rockland ref. 009-0103) for 15 min, $5 \times 10^5$ NK were incubated for 20 min at 4° C. with 0.25 µg of H7 IgG1 antibody or of a human IgG1 (isotype control), coupled to phycoerythrin using an antibody conjugation kit (Lynx ref. PE LNK021RPE) and a CD56-APC antibody. The histograms show the fluorescence profiles obtained with H7 $IgG_1$ (black) or the $hIgG_1$ control (grey), analysed on the CD56-positive population.

B) H7 $IgG_1$ induces the production of interferon-gamma (IFN-γ) by NK cells. NK cells purified from the blood of a healthy donor were cultured for 24 h in wells of 96-well plates ($1 \times 10^{+6}$ cells per well) alone or in the presence of the H7 $IgG_1$ antibody, or of a human IgG1 isotype control, concentrated to 1 or 10 µg/ml. The IFN-γ was assayed by ELISA in the culture supernatants. The results presented are means of triplicates+/−sem.

C) H7 $IgG_1$ induces the expression of the activation marker CD69 on NK cells. In the same experiment, the NK cells were collected after 24 h of culture and labelled with an anti-CD69 antibody conjugated to the fluorochrome APC. The percentages of CD69-positive cells were analysed by flow cytometry. The means(+/−sem) were calculated from triplicates.

Figure 11:
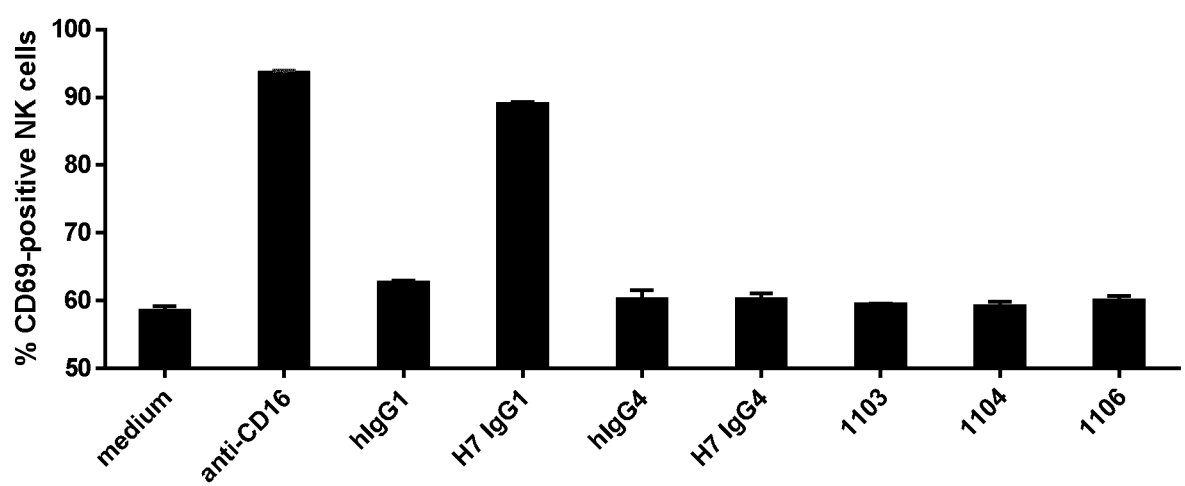

FIG. 11: The anti-CD160 H7 antibody in the IgG1 format, but not IgG4, activates NK cells.

NK cells purified from the blood of a healthy donor were cultured alone or in the presence of the following antibodies concentrated to 5 µg/ml: H7 IgG1, H7 IgG4, their respective human IgG1 or IgG4 isotype controls, or the antibodies ELB01103, ELB01104 and ELB01106, which are variants derived from the H7 antibody in the IgG4 format. The anti-CD16 antibody (Ebioscience cat #16-0166) is used as positive control. The NK cells ($5 \times 10^{+5}$ per well) were collected after 24 h of culture and labelled with an anti-CD69 antibody conjugated to the fluorochrome APC. The percentages of CD69-positive cells were analysed by flow cytometry (means of triplicates+/−SD). The anti-CD160 H7 in the IgG1 format induces the expression of the activation marker CD69 on NK cells, whereas the same antibody in the IgG4 format has no effect. The H7 variants IgG4 (ELB01103, ELB01104 and ELB01106) also do not show any activating effect on NK cells.

Figure 12:
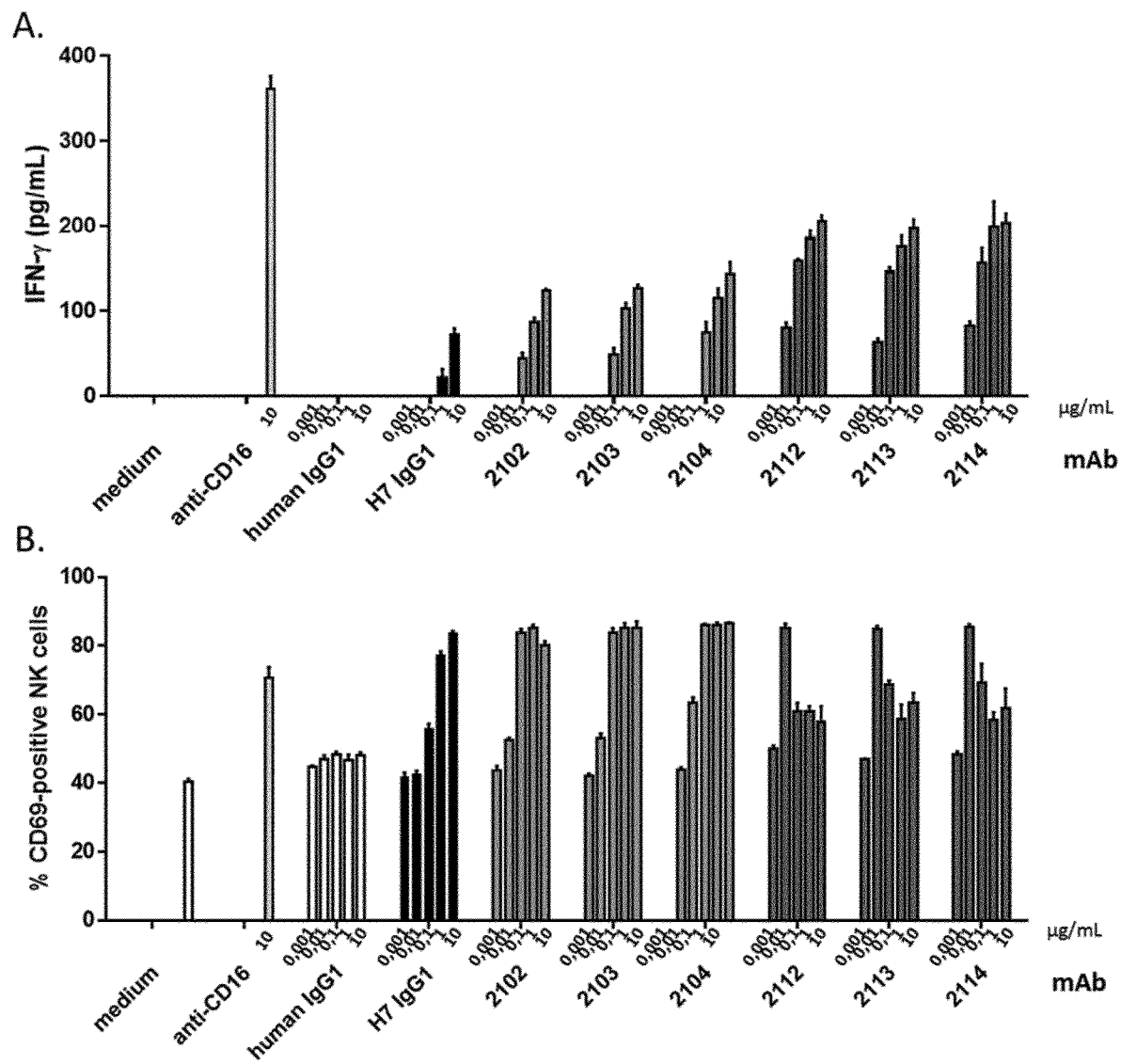

FIG. 12: The variants derived from the anti-CD160 H7 antibody in the IgG1 and E345K/IgG1 formats have an increased capacity to activate NK cells.

NK cells purified from the blood of a healthy donor were cultured for 24 h in wells of 96-well plates ($1 \times 10^{+6}$ cells per well), alone or in the presence of the anti-CD160 H7 IgG1 antibody, or of the variants ELB02102, ELB02103, ELB02104 (all three in the IgG1 format), ELB02112, ELB02113 or ELB02114 (all three in the E345K/IgG1 format) produced by ElsaLys, at doses of 0.001 to 10 µg/ml. A human IgG1 at 10 µg/ml was used as negative isotype control, and an anti-CD16 (Ebioscience cat #16-0166) was used as positive control.

A) The IFN-γ was assayed by ELISA in the culture supernatants. The results presented are means of triplicates+/−sem.

B) The NK cells were collected and labelled with an anti-CD69 antibody conjugated to the fluorochrome APC. The percentages of CD69-positive cells were analysed by flow cytometry. The means(+/−sem) were calculated from triplicates.

All of these results show that the three H7 variants in the IgG1 format (ELB02102, ELB02103, ELB02104) are much more potent than the original H7 IgG1 antibody in terms of activating NK cells, with an improvement of 2 to 3 logs of the EC50 values.

The three H7 variants in the E345K/IgG1 format show a further increased capacity for inducing IFN-γ production, with an additional improvement of 2 logs in the EC50 values (4 logs compared with the original H7 IgG1 antibody).

Figure 13A:
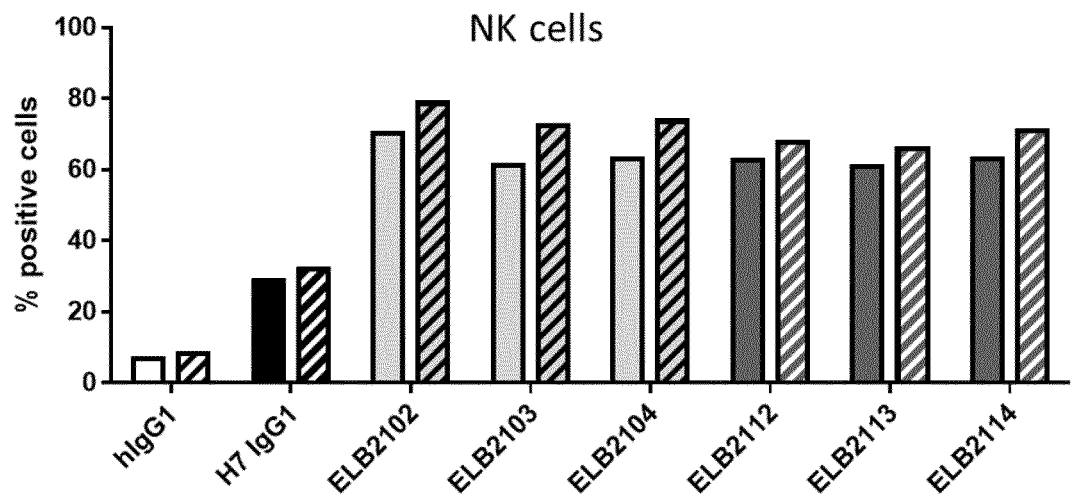
Figure 13B:
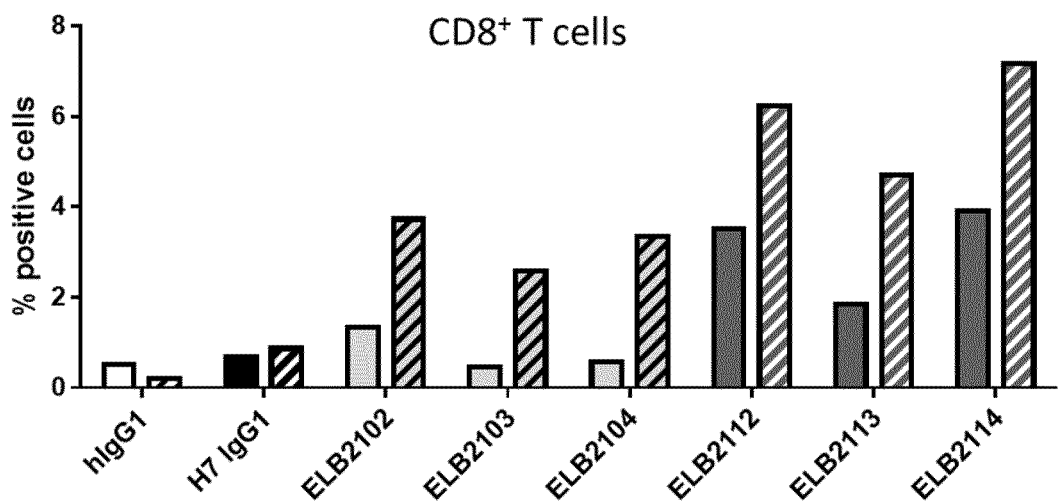

FIG. 13: The variants derived from the anti-CD160 H7 antibody in the IgG1 and E345K/IgG1 formats efficiently label NK (FIG. 13A) and CD8+T (FIG. 13B) cells.

The PBMCs (peripheral blood mononuclear cells) from two healthy donors were analyzed by flow cytometry after immunolabelling with anti-CD45, CD3, CD4, CD8 and CD19 antibodies and with the anti-CD160 antibodies indicated (0.25 µg for $5 \times 10^{+5}$ PBMCs). An irrelevant human IgG1 (hIgG1) was used as negative control. Non-hatched bars: donor 1; hatched bars: donor 2.

Figure 14:
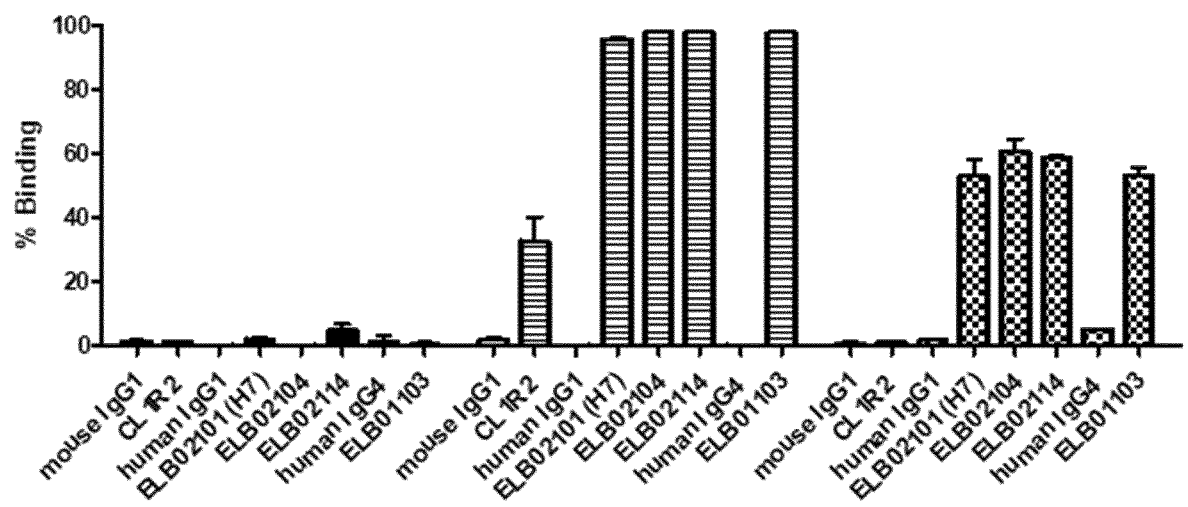

FIG. 14: Binding to CHO-CD160 TM (transmembrane), CHO-CD160 GPI (glycosylphosphatidylinositol) and CHO of CL1R2, ELB02101 (H7 IgG1) candidates and variants ELB02104, ELB02114 and ELB01103.

Humanized ELB02101 (H7 IgG1) and the variants ELB02104, ELB02114 and ELB01103 bind unexpectedly to human CD160-TM expressed recombinantly by the CHO-S cells while parental CL1R2 mAb doesn't bind. Black bars: CHO, hatched bars: CHO-CD160-GPI (glycosylphosphatidylinositol), checkerboard bars: CHO-CD160TM (transmembrane)

Figure 15:
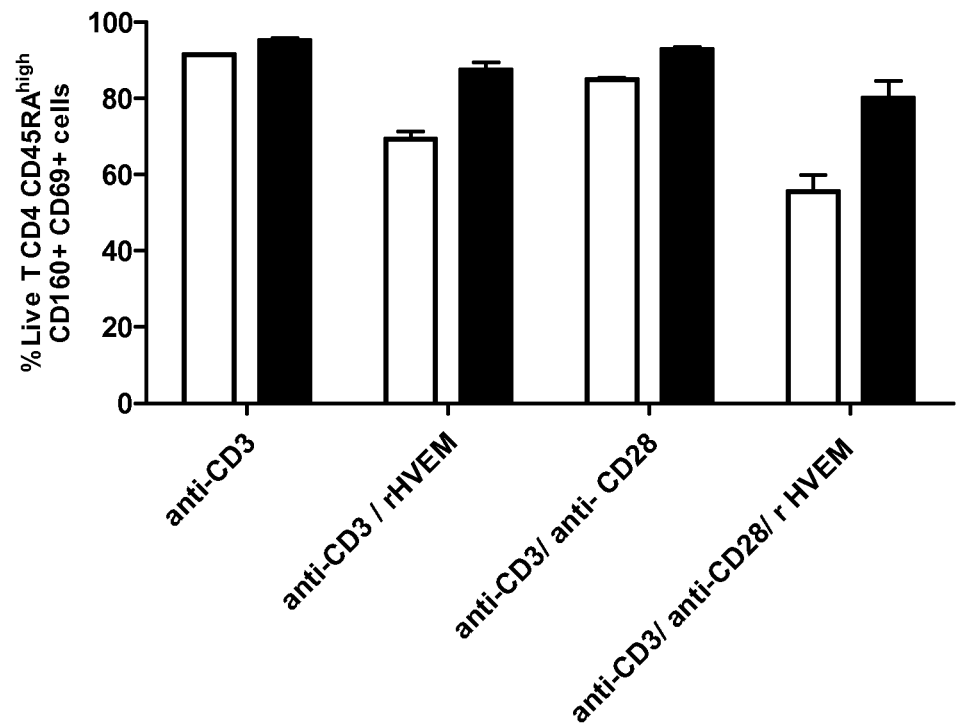

FIG. 15: T CD4 re-activation through the blocking of HVEM-CD160 interaction by the H7 A09 variant in IgG1 format (ELB02104).

T CD4 lymphocytes cells purified from the blood of a healthy donor were cultured for 16 h in 96-well plates ($1 \times 10^{+6}$ cells per well), in the presence of the anti-CD160 mAb: ELB02104 or with the appropriate control isotype at 10 µg/ml and with anti-CD3 (clone UTCH1) mAb+/−anti-CD28 (clone CD28.2) mAb+/−HVEM protein (10334-H08H, Sino biological) coated on the plate. T CD4 lymphocytes were collected and labelled with a viability marker: Zombie NIR, an anti-CD45RA antibody conjugated to the fluorochrome BB515 targeting Naïve/Memory cells, with an anti-CD160 (clone BY55) antibody conjugated to the fluorochrome Alexa fluor 647 targeting CD160 expressing cells and with an anti-CD69 antibody conjugated to the fluorochrome PE targeting activated cells. The percentage of Zombie NIR−/CD45RA$^{high}$+/CD160+/CD69+ positive cells were analyzed by flow cytometry. The means(+/−sem) were calculated from duplicates. ELB02104 blocks HVEM-CD160 interaction and removes the inhibition of TCD4 cells induced by HVEM protein as shown by the upregulation of CD69, an activation marker expressed by T CD4

CD45RA$^{High}$ CD160+ cells. White bars: human IgG1 control isotype, black bars: ELB02104

EXAMPLE 1

Study of the Binding of the Antibodies According to the Invention

The determination and the comparison of the affinities described in Table 1 of the murine anti-hCD160 CL1-R2 or in its derived forms (chimeric IgG1 and chimeric IgG4) or of the compounds of the invention (H7 IgG1, H7 IgG4) were carried out using the principle of biolayer interferometry on an Octet K2 instrument (Pall ForteBio) equipped with fibre optic biosensors of various types depending on the experiments. The capacity of the antibodies according to the invention to bind to their target was studied by measuring the human CD160 protein/antibody interaction.

For this, the monomeric anti-human CD160 antibodies of high purity (purified on protein A and then by gel filtration) were prepared by techniques well known to those skilled in the art. The protein region corresponding to the soluble form of the recombinant human CD160 protein bearing a C-terminal tag of 6 histidine residues (from R&D SYSTEMS) is used in its commercial formulation.

The affinities of the various anti-CD160 candidates to be tested, i.e. the compounds of the invention, were compared to that of the chimeric antibodies and of CL1-R2.

All the experiments were carried out at 30° C. in the running buffer recommended by Fortebio (PBS with 0.1% (p/v) of bovine serum albumin (BSA) and 0.02% (v/v) Tween-20). This buffer was also used for diluting the various ligands and analytes. The samples deposited in a 96-well microplate (cat #738-0026, Dutscher) were shaken at 1000 revolutions per minute.

The CD160 protein comprising a 6-histidine-residue tag which is biotinylated is used as ligand on streptavidin biosensor and the compounds, according to the invention, anti-hCD160 (IgG1 and IgG4 formats) and anti-CD160 and chimeric compounds are used as analytes.

This hCD160-his protein was biotinylated using the EZ-Link sulfo-NHS-LC-biotin method (Thermo Fisher Scientific) according to the supplier's recommendations and validated for its homogeneity, the absence of aggregates and its capacity to be recognized by anti-CD160s just as well as the non-biotinylated protein. Immobilization tests with various protein concentrations showed that a concentration of 10 nM was optimal. The biotinylated CD160 protein was therefore immobilized at a concentration of 0.3 µg/ml (i.e. 10 nM) on streptavidin biosensors for 10 min. A typical immobilization results in a signal of 2+/−0.3 nm.

The kinetic constants ($K_D$, $k_{on}$ and $k_{off}$ also called $K_{dis}$) were determined for each of the purified antibodies (molecular weight 150 kDa) by addition of 6 concentrations of antibodies (of 3.125, 6.25, 12.5, 25, 50 and 100 nM). Between the measurements, the surfaces of the biosensor were regenerated by exposing them to 3 cycles of 5 sec in 10 mM glycine, pH 2, followed by 5 sec in running buffer. The association and dissociation phases were measured for 300 seconds. All the measurements were corrected for the basic drift by subtracting a reference well with a ligand subjected only to the running buffer.

The dissociation constants and the association ($k_{on}$) and dissociation ($k_{dis}$) rate constants for each antibody were calculated by applying a 1:1 interaction model, with overall mathematical modelling of curves (fit) (Rmax bound by the sensor) on the ForteBio 9.0 data analysis software. The curves that could not be reliably modelled using the software (most of the time with an R2 full <0.925), generally caused by binding according to a heterogeneous mode, were excluded from the analyses.

For each anti-CD160, the dissociation constants (KD), and the association ($k_{on}$) and dissociation ($k_{dis}$) rate constants, and also the binding response were compared for anti-CD160 antibody concentrations of 50 nM and are reported in Table 1.

TABLE 1

Measurement by Biolayer interferometry (BLI) of the affinity of the recombinant human CD160/anti-hCD160 interaction for the murine CL1-R2 antibody, the chimerized antibodies issued from CL1-R2 (in the human IgG1 (chIgG1) or IgG4 (chIgG4) formats) and the H7 antibody of the invention (in the human IgG1 (H7 IgG1) or IgG4 (H7 IgG4) format).

| Anti-hCD160 (batch) | $K_D$ (nM) | $K_D$ Error (*1E$^{-11}$) | $k_{on}$ (1E$^{+5}$/Ms) | $k_{on}$ Error (*1E$^{+03}$) | $k_{dis}$ (1E$^{-03}$/s) | $k_{dis}$ Error (*1E$^{-05}$) | $K_D$ gain (/$K_D$ parental CL1-R2) | Binding response, at 50 nM of anti-CD160 (arbitrary units nm) |
|---|---|---|---|---|---|---|---|---|
| H7 IgG1 | 4.00 | 2.83E−11 | 5.87 | 3.06 | 2.35 | 1.12 | 3.75 | 1.01 |
| chIgG1 | 14.3 | 16.5E−11 | 2.08 | 1.94 | 2.97 | 2.06 | 1.07 | 0.41 |
| H7 IgG4 | 4.49 | 5.39E−11 | 3.50 | 2.65 | 1.57 | 1.47 | 3.34 | 0.60 |
| chIgG4 | 14.8 | 1.52E−10 | 2.18 | 1.83 | 3.23 | 1.92 | 1.04 | 0.41 |
| CL1-R2 | 15.4 | 1.74E−10 | 1.83 | 1.69 | 2.83 | 1.83 | 1 | 0.60 |

The affinity measurements clearly show here, unexpectedly, that the H7, in the IgG1 and IgG4 formats, has a much better affinity for human CD160 than the murine CL1-R2 and its respective chimeric human IgG1 and IgG4 forms. The gain in $K_D$ (cf. $K_D$ gain, Table 1, column 8) compared to the parental CL1-R2 anti-CD160 $K_D$ is about 3.75 and 3.34 for H7 in the human IgG1 and IgG4 format respectively. For one and the same concentration of 50 nM of antibody, a better response for the H7 IgG1 than for H7 IgG4 and CL1-R2 and a worse response for the two anti-CD160s in the chimeric formats were also obtained (Table 1, column 9).

It was also verified that the H7 bind well to their target, by flow cytometry study on recombinant E300-hCD160 cells overexpressing human CD160 and by ELISA on CD160 protein and on peptide of a protein sequence necessary and sufficient for there to be binding of the anti-hCD160 antibody, identified by peptide scanning of the human CD160 sequence.

The H7 candidate is the candidate chosen for the remainder of the experiments, in particular for being affinity matured and for being derived into various formats of IgG or of IgG fragments suitable for the various clinical indications targeted.

EXAMPLE 2

The Variants of the H7 Antibody

Binding Profile, by ELISA, FACS and SPR, of a Panel of H7 Variants in the Form of Phages and Soluble Fabs Produced in Periplasmic Extracts of Bacteria.

In order to obtain variants derived from the humanized anti-CD160 candidate H7, a site-directed mutagenesis of the residues of the specific complementarity-determining regions (CDRs) of the heavy and light chain variable domains (VH and VL respectively) of the H7 antibody were combined with a selection on protein and on CHO cells overexpressing hCD160 by phage display of the variants in the Fab format.

Thus, phage clones were generated and also made it possible to produce periplasmic extracts of bacteria, containing unpurified soluble Fabs. The individual clones were selected for their binding capacity to the human CD160 protein, by ELISA, and to cells expressing human CD160 by FACS, this being i) either in the form of gene III-Fab fusion proteins expressed at the surface of the filamentous phage or ii) in the form of periplasmic extracts containing fragments of unpurified soluble Fabs. The results of the experiments termed phage ELISA and phage FACS are reported in Table 2. The individual clones (in the form of periplasmic extracts containing fragments of soluble Fabs) were also classified according to their kinetic dissociation constant ($k_{dis}$).

The summary of the data obtained for the 6 H7 variants and in the form of periplasmic extracts containing fragments of unpurified soluble Fabs (PE ELISA and PE FACS) is given in Table 2.

From a practical point of view, the binding of the phage to human CD160 was detected using an anti-M13 HRP conjugated antibody. The binding of the phage to the cells expressing CD160 was detected using a mouse anti-M13-biotin antibody followed by Streptavidin-PE.

In the phage ELISA, most of the phages were able to bind the human CD160 protein with high optical density (OD) values at 450 nm (OD 450: 1.0-6.0) and with a degree of binding success of 83% (OD at 450 nm≥10 mean of the background noise). It is important to note that, for the H7 WT Fab phage, the OD 450 values obtained were as low as 0.06-0.07.

Similar results were obtained from the phage FACS assay, with a degree of success of 91% (clones with more than 5% of binding to cells expressing CD160, 3 times the virgin MFI values and no binding to the CHO-S WT cells was considered positive). As in the phage ELISA, the binding values obtained for the Fab H7 WT phage FACS were much lower compared with the other clones.

The binding of the clones selected (from the rounds of selection on CD160 protein and on CHO-CD160 cells) as soluble Fab was also looked at by ELISA and FACS using periplasmic extracts (P.E). The binding of the soluble Fabs to the human CD160 protein, using ELISA, was detected using an anti-c-myc antibody followed by an anti-mouse HRP conjugated antibody. The binding of the soluble Fabs to the CHO cells overexpressing human CD160 was detected using an anti-c-myc antibody followed by a goat anti-mouse APC conjugated antibody. The results of the ELISA and FACS experiments using Fabs expressed at the surface of the phages or in periplasmic extracts confirmed the binding capacity of each of the affinity-matured H7 clones to human CD160.

TABLE 2

Class of affinity-matured heavy chain H7 variants in the form of phages and soluble Fabs produced in periplasmic extracts of bacteria, clone identification, binding profile by ELISA, FACS and SPR.

| Anti-CD160 phage cloning | H7 VH family No. | VH | Phage ELISA O.D$_{450\,nm}$ on biotinylated CD160 | P.E ELISA O.D$_{450\,nm}$ on biotinylated CD160 | Phage FACS (% binding) | P.E FACS (% binding) |
|---|---|---|---|---|---|---|
| FJ1516MP02F04 | 1 | SEQ ID No: 25 | 3.323 | 0.436 | 96.53 | 9.86 |
| FJ1516MP02D09 | 2 | SEQ ID No: 26 | 3.63 | 0.174 | 76.36 | 1.08 |
| FJ1516MP02A12 | 3 | SEQ ID No: 27 | 6 | 0.148 | 92.06 | 1.23 |
| FJ1516MP02G05 | 4 | SEQ ID No: 28 | 3.458 | 0.141 | 86.86 | 1.06 |
| FJ1516MP02D12 | 5 | SEQ ID No: 29 | 6 | 0.312 | 95.09 | 1.89 |
| FJ1516MP02A09 | 6 | SEQ ID No: 30 | 6 | 0.124 | 94.19 | 0.54 |
| FJ1516MP02E07* | WT | | 3.209 | 0.145 | 70.44 | 0.21 |
| FJ1516MP02G12** | WT | | 1.007 | 0.131 | 11.75 | 0.26 |

*WT H7 obtained in the screening
**Fab H7 WT control produced

The amino acid sequences of the various clones originating from different rounds of selection (FJ1516MP02 and FJ1516MP03) were extracted using the CLC Main Workbench software. The mutant Vκ and VH sequences were aligned separately with respect to the reference H7 VH and Vκ sequences. All the clones selected contain a Vκ sequence corresponding to the Vκ sequence of the H7 WT. For the heavy chain, starting from 156 valid sequences, six also corresponded to the VH sequence of H7 WT. All the other VH sequences contained 2 to 6 mutations (as designed in the library) relative to WT and were grouped together in 6 different classes (VH variant sequences 1 to 6) (see column 2, VH family in Table 2 above).

For the remainder of the characterization experiments, a panel containing a clone representative of each different VH variant was selected for the production of phage and of soluble Fab in P.E. The list of representatives selected is given in column 1 of Table 2 and their corresponding VH family in column 2. The clone representative of class 5 is D12, the clone representative of class 1 is F04 and the clone representative of class 6 is A09. The VH amino acid sequences of the clones representing the various classes 1 to 6 of the variants of the anti-CD160 H7 are mentioned in Table 2.

The alignment of the protein sequences of the VH regions of these 6 classes of H7 variants showed common constants between the various classes of variants in terms of the positions of the mutated residues and in terms of the nature of the mutations introduced.

SPR Measurement of Interaction with Human CD160 of the 6 Variant Fabs of H7 Using Soluble Fabs Produced in Bacterial Periplasmic Extracts The binding capacity of the H7 variants was also tested by surface plasmon resonance (SPR). For this, a Biacore 3000 (GE Healthcare) was used. 50 µg/ml of human CD160 (R & D Systems) in an acetate buffer, pH 4.5, were immobilized on a CM5 chip (GE Healthcare) at 1250-2000 resonance units (RUs). The integrity of the immobilized human CD160 was confirmed using the anti-huCD160 H7 IgG1 antibody. For the kinetic measurements, concentrations in cascade of human ECD160 with two-fold dilutions (0.15 µM-10 µM) were injected, twice, in PBS, with a Biacore P20 buffer at 25° C. and a flow rate of 30 µl/min.

The regeneration conditions were tested and 10 pi of 10 mM NaOH/1M NaCl were injected for the regeneration between the sample injections. To analyse the binding of the clones to human CD160, the periplasmic extracts containing the soluble Fabs were diluted to 1:5 in BIACORE P20 buffer (10 mM Hepes, 150 mM NaCl, 3 mM EDTA, 0.005% Tween-20) with a flow rate of 30 µl/min for 120 seconds for the association; the dissociation was measured for 300 seconds.

TABLE 3

Absolute response of the binding of the periplasmic extracts containing soluble Fabs representative of the various classes of affinity-matured H7 variants

| Anti-CD160 phage clone | H7 VH family No. | Binding response, RU arbitrary unit (at t = 120 s post-mab injection) | Biacore R.U ratio (variant/ H7 WT) | Biacore R.U ratio (variant/ FaWT 2E07) |
|---|---|---|---|---|
| FJ1516MP02F04 | 1 | 50.6401 | 8.3 | 3.9 |
| FJ1516MP02D09 | 2 | 19.2957 | 3.2 | 1.5 |
| FJ1516MP02A12 | 3 | 20.1003 | 3.3 | 1.5 |
| FJ1516MP02G05 | 4 | 16.0439 | 2.6 | 1.2 |
| FJ1516MP02D12 | 5 | 43.7766 | 7.2 | 3.3 |
| FJ1516MP02A09 | 6 | 16.7186 | 2.7 | 1.3 |
| FJ1516MP02E07* | WT | 13.1271 | 2.2 | 1 |
| FJ1516MP02G12** | WT | 6.08838 | 1 | 0.5 |

*WT H7 obtained by selection in the screening
**Fab H7 WT control produced

The maximum absolute response of the binding of each of these variants (expressed as measurement of arbitrary response units at time=120 seconds post-injection of the antibody) was evaluated on a surface coated with CD160 protein. These data are in Table 3.

It was then possible to calculate the ratio of binding of each variant to that of the H7 Fab produced as a control or an H7 Fab isolated on a phage during the screening (cf. Table 3, columns 4 and 5).

The data grouped together in Table 3 demonstrate that the soluble Fabs are capable of binding human CD160 in agreement with what was previously observed by ELISA and FACS.

The clones F04, D12 and A09 (variant VH of classes 1, 5 and 6 respectively) showed the highest binding values (RU) and also RU ratios (cf. column 4, variant RU/WT RU Table 3) that were also high, of 8.3; 7.2 and 2.7 times, respectively.

EXAMPLE 3

Design and Generation of Various Monospecific Antibody Formats for the Variants for the Oncology and Ophthalmology Indications The clones FJ1516MP02F04 or F04 and FJ1516MP02D12 or D12 were formatted in IgG in order to study whether the mutations present could make it possible to bind to CD160 with affinities higher than that of the H7 antibody. The FJ1516MP02A09 or A09 variant is the only representative which also has an association/dissociation profile very different from the others and, in this respect, will also be studied further in the IgG format.

3.1) Protein Sequences of the Anti-CD160 Constructs to be Tested in Ophthalmology Using H7 and its Variants Thus, for ophthalmology, the F04 and D12 variants were generated in formats (IgG4 or IgG1 N297Q for example) chosen to not interact, or to interact minimally, with Fc receptors (FcR), and/or others for reducing the systemic half-life of the therapeutic anti-CD160 antibody or fragment, without reducing too much its intravitreal half-life by producing in this case either mutations that reduce the systemic half-life of the antibody, or either by proposing formats of antibody fragments without Fc region.

Reduction of the Systemic Half-Life and of the Engagement of FcRs and of FcRns by Formatting the H7 Candidate and its Variants in an IgG4 or IgG1 N297Q+/−FcRn Null Mutations Thus, for ophthalmology, a first possibility to reduce the systemic half-life of the therapeutic anti-CD160 antibody, is to format the F04 and D12 variants by cloning the variable regions on an IgG4 S228P-R409K or IgG1 N297Q structure chosen to not interact, or to interact minimally, with Fc receptors (FcR). On this backbone it also possible to insert the mutations S228P/R409K/H310A/H435Q or I253A in the Fc region of the Mab to reduce its interaction with human neo natal Fc receptor (FcRn and "FcRn null mutations" described in (Olafsen, 2012). This could be achieved by different combinations of heavy and light chain sequences as described in Table 4.

TABLE 4

Name of the compounds and VH and VL sequences

| ELB code | Anti-CD160 name/code | Heavy chain | Light chain |
|---|---|---|---|
| ELB01101 | H7 IgG4 S228P/R409K | SEQ ID No: 58 | SEQ ID No: 57 |
| ELB01103 | D12 IgG4 S228P/R409K | SEQ ID No: 60 | SEQ ID No: 57 |
| ELB01106 | F04 IgG4 S228P/R409K | SEQ ID No: 61 | SEQ ID No: 57 |
| ELB01111 | H7 IgG1 N297Q | SEQ ID No: 59 | SEQ ID No: 57 |
| ELB01102 | H7 IgG4 S228P/R409K/ H310A/H435Q | SEQ ID No: 62 | SEQ ID No: 57 |
| ELB01104 | D12 IgG4 S228P/R409K/ H310A/H435Q | SEQ ID No: 63 | SEQ ID No: 57 |
| — | F04 IgG4 S228P/R409K/ H310A/H435Q | SEQ ID No: 10 | SEQ ID No: 57 |
| — | D12 IgG4 S228P/R409K/ I253A | SEQ ID No: 9 | SEQ ID No: 57 |
| — | F04 IgG4 S228P/R409K/ I253A | SEQ ID No: 12 | SEQ ID No: 57 |

SEQ ID No: 57 results from the fusion of the variable region defined by SEQ ID No: 14 to the constant region defined by SEQ ID No: 22.

Reduction of the Systemic Half-Life and of the Engagement of FcRs and of FcRns by Formatting the H7 Candidate and its Variants in Antibody Fragments.

Another way to reduce the systemic half-life and also the engagement of FcRs and of FcRns of a therapeutic antibody injected in IVT is the formatting of the H7 antibody and its variants in antibody fragments (Fab, Fab'2 for example). Thus, the H7 and its variants are formatted in Fab format (with the following Fab constant chain synthesized by genetic engineering and produced in bacteria or in CHO cells) by combining the light chain of H7 (SEQ ID No: 57) with one of the following heavy chains in order to produce the corresponding format (see Table 4).

Fab CH1 IgG1 ELB01121 (SEQ ID No: 36)
Fab CH1 IgG1 D12 ELB01122 (SEQ ID No: 37)

The Fab'2 format is produced for the D12 variant (SEQ ID No: 38) (recombinantly or by enzymatic cleavage (Ides fabricator, GeNovis)) with two disulfide bridges instead of one or with or without leucine zipper.

A Fab linker Fab was generated in which the two sequences of the heavy chains are linked between the C terminal of the first Fab with the N-terminal of the second Fab by means of a linker protein sequence (SEQ ID No: 39), which gives a heavy chain of the Fab-linker-Fab molecule ELB01131 defined by SEQ ID No: 40 and ELB01132 defined by SEQ ID No: 41.

A tetravalent format with 4 anti-CD160 D12 Fabs was created using as heavy chain of the tetravalent the IgG1 N297Q H310A-H435Q D12 (SEQ ID No: 42; ELB012001).

All of the sequences of these heavy chains are the sequences of a mature heavy chain and the sequence of a signal peptide, such as one of those described in SEQ ID No: 18 or 19, must be added in the N-terminal position.

3.2) Protein Sequences of the Anti-CD160 Constructs to be Tested in Oncology Using H7 and its Variants.

The different formats that were compared for oncology are H7 and its three variants D12, F04 and A09 in the IgG1 format, and also in the Hexabody format of Genmab and in the Bite format for D12.

The Hexabody format (Diebolder et al., 2014; de Jong et al., 2016) was generated so as to optimize the cytotoxicity of the anti-CD160 in order to activate complement and to improve the capacity of the antibody to induce lysis, by CDC and ADCC, of CD160-positive tumour cells. Wang et al. (Wang et al., 2016) identified mutations E345K (SEQ ID No: 43) or E430G (SEQ ID No: 44) which allow the production of a monomeric Hexabody with improved effector functions (CDC and ADCC) while at the same time retaining equivalent pharmacokinetics and pharmaceutical developability. The IgG1 thus mutated hexamerizes following binding of the antibody to the antigen expressed by the target cell and this hexamerization improves the effector functions (CDC and ADCC) of the antibody. The molecular construction of the D12 and F04 variants in the IgG2a/murine kappa format, as preclinical tools, was also carried out.

TABLE 5

Name and ElsaLys codes (ELB) of the compounds and VH and VL sequences

| ELB code | Anti-CD160 name/code | Heavy chain | Light chain |
| --- | --- | --- | --- |
| ELB02101 | Human H7 IgG1 | SEQ ID No: 64 | SEQ ID No: 57 |
| ELB02102 | D12 in the IgG1 format | SEQ ID No: 45 | SEQ ID No: 57 |
| ELB02103 | F04 in the IgG1 format | SEQ ID No: 46 | SEQ ID No: 57 |
| ELB02104 | A09 in the IgG1 format | SEQ ID No: 47 | SEQ ID No: 57 |
| ELB02111 | H7 in the IgG1 E345K format | SEQ ID No: 48 | SEQ ID No: 57 |
| ELB02112 | D12 in the IgG1 E345K format | SEQ ID No: 49 | SEQ ID No: 57 |
| ELB02113 | F04 in the IgG1 E345K format | SEQ ID No: 50 | SEQ ID No: 57 |
| ELB02114 | A09 in the IgG1 E345K format | SEQ ID No: 51 | SEQ ID No: 57 |
| ELB02102-02 | D12 in the murine IgG2a format | SEQ ID No: 53 | - SEQ ID No: 54 |
| ELB02103-02 | F04 in the murine IgG2a format | SEQ ID No: 55 | SEQ ID No: 56 |

Moreover, the protein sequence of the D12 variant in the BITE format, ELB02122, is defined by SEQ ID No: 52.

EXAMPLE 4

Biophysical Characterization of the H7 Variants in the IgG4, IgG1 and IgG1 E345K Formats 4.1) Evaluation of the Impact of the Mutations of the H7 Variants on the Thermostability of the Anti-CD160s.

Thermostability is a common method used for studying the stability of a protein. Thermostability results i) from the intrinsic stability of a protein (propensity to form aggregates) linked to its three-dimensional structure that results from its primary sequence, and ii) from the sample storage and formulation conditions (pH, salts, and components of the sample). According to the method based on the differential capacity of Sypro Orange (Thermofischer Scientific, S-6650, batch 1608495) to bind to the hydrophobic regions of the protein in native or denatured form, the thermostability of the variants of the anti-hCD160 H7 candidate in various IgG formats was evaluated.

The samples are tested in quadruplicate in a 96-well PCR plate, in a final volume of 30 µl at a final concentration of 0.1 mg/ml in 1× PBS, 5× Sypro Orange. The stock solution of Sypro Orange (5000× stock in 100% DMSO) is prepared at a final concentration of 10× in 1× PBS. The plate is then subjected to a temperature gradient of 22° C. to 99° C. (over the course of approximately 1 h 30) in an Applied Biosystems® 7500 Real-Time PCR system device. The data analysis (raw data and first derivative giving the Tm for each antibody domain) was carried out using the software: Protein Thermal Shift (Thermofischer Scientific). The results are presented in the following table:

TABLE 6

Tm results for H7 and the H7 variants in the IgG4, IgG1 and IgG1 E345K formats

| Code | Protein | Mean Tm1, ° C. | Standard deviation Tm1 | Mean Tm2, ° C. | Standard deviation Tm2 |
| --- | --- | --- | --- | --- | --- |
| ELB01101 | H7 IgG4 WT | 65.49 | 0.10 | | |
| ELB02101 | H7 IgG1 WT | 68.98 | 0.12 | | |
| ELB01103 | D12 IgG4 | 65.02 | 0.07 | 72.62 | 0.07 |

TABLE 6-continued

Tm results for H7 and the H7 variants in
the IgG4, IgG1 and IgG1 E345K formats

| Code | Protein | Mean Tm1, °C. | Standard deviation Tm1 | Mean Tm2, °C. | Standard deviation Tm2 |
|---|---|---|---|---|---|
| ELB01106 | F04 IgG4 H310A-H435Q | 60.66 | 0.07 | 69.85 | 0.07 |
| ELB01102 | H7 IgG4 H310A-H435Q | 60.77 | 0.04 | 69.13 | 0.04 |
| ELB01104 | D12 IgG4 H310A-H435Q | 60.55 | 0.09 | 71.61 | 0.09 |
| ELB02104 | A09 IgG1 | 69.38 | 0.21 | 74.75 | 0.07 |
| ELB02103 | F04 IgG1 | 69.63 | 0.07 | | |
| ELB02102 | D12 IgG1 | 69.60 | 0.07 | | |
| ELB02113 | F04 IgG1 E345K | 69.52 | 0.12 | | |
| ELB02114 | A09 IgG1 E345K | 69.05 | 0.04 | 74.28 | 0.00 |
| ELB02112 | D12 IgG1 E345K | 69.67 | 0.06 | | |
| ELB01111 | H7 IgG1 N297Q | 59.58 | 0.16 | 70.50 | 0.11 |
| ELB01112 | H7 IgG1 N297Q H310A-H435Q | 53.96 | 0.00 | 70.17 | 0.04 |

The analysis of the results of Table 6 shows that the mean Tm of H7 in the IgG1 format (H7 IgG1 WT) is 3.5° C. higher compared with H7 in the IgG4 format (H7 IgG4 WT). Regarding the H7 variants, the antibodies have a Tm very close to that of H7.

4.2) BLI Measurement for Comparison of the Affinity for the Recombinant Human CD160, of H7 and of the Different Variants Thereof, this Being in Different IgG Formats The affinities herein were measured as described in Example 2 with a design where the biotinylated CD160 protein is captured at 10 nM on a streptavidin biosensor and where the analytes are the anti-CD160s. The anti-CD160 concentrations tested were 3.13, 6.25, 12.5, 25, 50 and 100 nM and the glycine concentration, pH 2, was 10 mM for each regeneration.

The sensorgrams and the affinities measured for the CD160 protein, of the anti-CD160 H7 antibodies and of the variants thereof, are presented in the following tables:

TABLE 7

Measurement of the affinities for the CD160 protein, of the anti-CD160 H7 antibody and of the D12 variant thereof in the IgG4 S228P-R409Q format

| Reference IgG, No. | KD (M) | kon(1/Ms) | kdis(1/s) | RMax | Full X^2 | Full R^2 |
|---|---|---|---|---|---|---|
| ELB01101 H7 IgG4 | 2.61E−09 | 4.69E+05 | 1.23E−03 | 0.4394 | 0.1146 | 0.9907 |
| ELB01103 | 1.52E−09 | 4.94E+05 | 7 52E−04 | 0.8059 | 0.2698 | 0.9947 |

TABLE 8

Measurement of the affinities for the CD160 protein, of the anti-CD160 H7 antibody and of the variants thereof in the IgG4 S228P-R409Q-H310A-H435Q format

| Reference IgG, No. | KD (M) | kon(1/Ms) | kdis(1/s) | RMax | Full X^2 | Full R^2 |
|---|---|---|---|---|---|---|
| ELB01102 H7 IgG4 H310A-H435Q | 2.91E−09 | 5.07E+05 | 1.48E−03 | 0.4832 | 0.1092 | 0.9924 |
| ELB01104 | 1.49E−09 | 4.99E+05 | 7.44E−04 | 0.7845 | 0.3143 | 0.9935 |
| ELB01106 | 1.63E−09 | 4.53E+05 | 7.36E−04 | 0.7779 | 0.1797 | 0.996 |

TABLE 9

Measurement of the affinities for the CD160 protein, of the anti-CD160 H7 antibody and of the variants thereof in the IgG1 format

| Reference IgG, No. | KD (M) | kon(1/Ms) | kdis(1/s) | RMax | Full X^2 | Full R^2 |
|---|---|---|---|---|---|---|
| ELB02101 H7 IgG1 | 2.94E−09 | 3.70E+05 | 1.09E−03 | 0.533 | 0.1222 | 0.9923 |
| ELB02102 | 1.55E−09 | 4.22E+05 | 6.54E−04 | 0.9513 | 0.2779 | 0.9958 |
| ELB02103 | 1.43E−09 | 3.71E+05 | 5.31E−04 | 0.8735 | 0.237 | 0.9955 |
| ELB02104 | 1.47E−09 | 4.42E+05 | 6.51E−04 | 0.8788 | 0.3971 | 0.9933 |

TABLE 10

Measurement of the affinities for the CD160 protein, of the anti-CD160 H7 antibody and of the variants thereof in the IgG1 E345K format

| Reference IgG, No. | KD (M) | kon(1/Ms) | kdis(1/s) | RMax | Full X^2 | Full R^2 |
|---|---|---|---|---|---|---|
| ELB02101 H7 IgG1 | 2.94E−09 | 3.70E+05 | 1.09E−03 | 0.533 | 0.1222 | 0.9923 |
| ELB02112 | 1.52E−09 | 4.47E+05 | 6.79E−04 | 1.2637 | 0.8515 | 0.993 |

TABLE 10-continued

Measurement of the affinities for the CD160 protein, of the anti-CD160
H7 antibody and of the variants thereof in the IgG1 E345K format

| Reference IgG, No. | KD (M) | kon(1/Ms) | kdis(1/s) | RMax | Full X^2 | Full R^2 |
|---|---|---|---|---|---|---|
| ELB02113 | 1.55E−09 | 4.27E+05 | 6.62E−04 | 1.1864 | 0.6878 | 0.9934 |
| ELB02114 | 1.93E−09 | 4.27E+05 | 8.25E−04 | 1.1987 | 0.6949 | 0.9931 |

Regardless of the variant, and regardless of the nature of the isotype (IgG4, IgG4 H310A-H435Q, IgG1 and IgG1 E345K), the variants always have at least a 2-fold improvement in affinity for the recombinant CD160 compared with the corresponding H7, a biolayer that is twice as thick reflecting a better $k_{on}$ and a dissociation constant which is two times lower than the corresponding parental H7.

The H7 variants, regardless of the variant and regardless of the nature of the isotype (IgG4, IgG4 H310A-H435Q, IgG1 and IgG1 E345K) have better kinetic characteristics than H7.4.3-Biacore (SPR) measurement for comparison of the affinity for the recombinant human CD160, of H7 and of the different variants thereof, this being in different IgG formats In order to compare the affinity for the recombinant human CD160, of H7 and of the different variants thereof, Biacore (SPR) measurements were also carried out as described in a design close to that described in Example 2.

EXAMPLE 5

Figure 1:
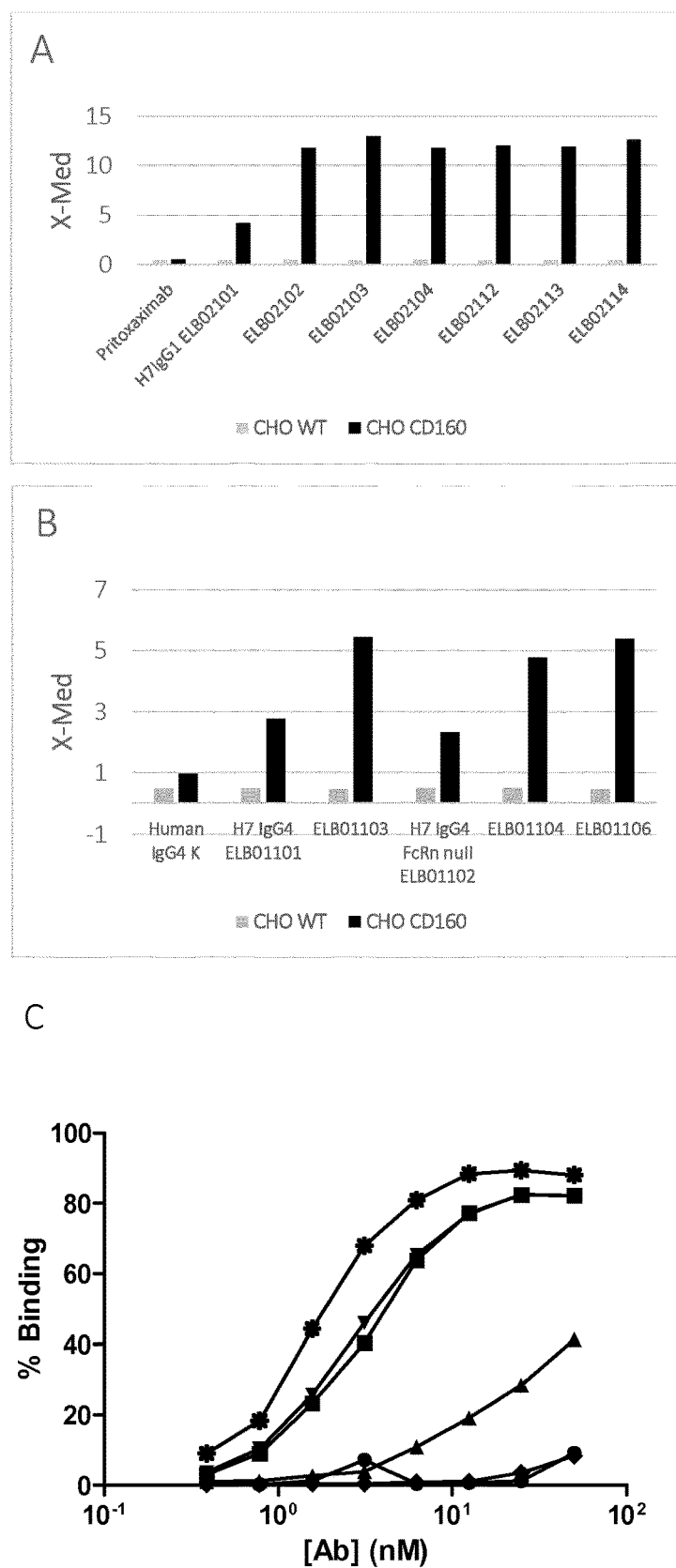
FIG. 1:
A) Binding to CHO-hCD160 compared with CHO WT of the H7 candidates and of variants thereof in the IgG1 format and IgG1 E345K B) Binding to CHO-hCD160 compared with CHO WT of the H7 candidates and of variants thereof in the IgG4 format and IgG4 H310A-H435Q C) Binding to YT2C2 (NK cell line) of the H7 candidate IgG4 (ELB01101) and of H7 D12 variant in the IgG4 format (ELB01103) with additional FcRn null mutations (ELB01104), on Fab format (ELB01122) and on Fab-linker-Fab format (ELB01132)) Black circle: human IgG4, black triangle: ELB01101 (H7 IgG4), black inverted triangle: ELB01103, black square: ELB01104, black diamond: ELB01122, black star: ELB01132.

Binding of the Anti-hCD160 H7 and of the H7 Variants Thereof in the IgG4 and IgG1 Format and in the IgG1 E345K Format on CHO CD160 Cells and on Non-Transfected CHO Cells and on NK Cell Line YT2C2 CD160 Cells The binding capacity of the anti-CD160 H7 antibodies and of the variants (D12 and A09) thereof in the IgG4 and IgG1 format and in the IgG1 E345K format was evaluated during the labelling of surface CD160 expressed in a recombinant line CHO-S-hCD160 (clone 2G10) in comparison with non-transfected CHO-S cells, by measuring the median fluorescence index (MFI) (see FIG. 1). For this, $5 \times 10^{+5}$ 2G10 (CHO-S-CD160) and non-transfected CHO-S cells were labelled with 2 µg of each of these antibodies and also with the appropriate control isotypes. In FIG. 1, all the

TABLE 11

Affinities of the recombinant human CD160/anti-hCD160 interaction of the H7 antibody and the variants
thereof in different formats measured by Biacore (SPR) and by Biolayer interferometry (BLI)

| Anti-CD160 code | Measurement method | kon (1/Ms) | kdis (1/s) | Rmax (RU) | KD (nM) | Gain in KD/respective IgG | Chi2 (SPR) or Full X^2 (BLI) | Full R^2 BLI |
|---|---|---|---|---|---|---|---|---|
| ELB02101 H7 IgG1 WT | SPR | 2.09E+05 | 2.51E−03 | 630 | 12 | | 12.60 | |
| | BLI | 3.70E+05 | 1.09E−03 | 0.533 | 2.94 | | 0.12 | 0.99 |
| ELB02101 H7 IgG1 D12 | SPR | 2.51E+05 | 1.13E−03 | 1200 | 4.5 | 2.7 | 57.70 | |
| | BLI | 4.22E+05 | 6.54E−04 | 0.9513 | 1.55 | 1.9 | 0.28 | 1.00 |
| ELB02101 H7 IgG1 F04 | SPR | 2.00E+05 | 7.26E−04 | 1280 | 3.6 | 3.3 | 23.30 | |
| | BLI | 3.71E+05 | 5.31E−04 | 0.8735 | 1.43 | 2.1 | 0.24 | 1.00 |
| ELB02101 H7 IgG1 A09 | SPR | 2.23E+05 | 8.77E−04 | 1250 | 3.9 | 3.0 | 36.30 | |
| | BLI | 4.42E+05 | 6.51E−04 | 0.8788 | 1.47 | 2.0 | 0.40 | 0.99 |
| ELB01101 H7 IgG4 WT | SPR | 2.18E+05 | 2.85E−03 | 533 | 13.1 | | 15.40 | |
| | BLI | 4.69E+05 | 1.23E−03 | 0.0021 | 2.61 | | 0.11 | 0.99 |
| ELB01103 H7 IgG4 D12 | SPR | 2.92E+05 | 1.22E−03 | 990 | 4.2 | 3.1 | 54.40 | |
| | BLI | 4.94E+05 | 7.52E−04 | 0.0026 | 1.52 | 1.7 | 0.27 | 0.99 |
| ELB01102 H7 IgG4 WT S228P/R409K/ H310A/H435Q | SPR | 2.05E+05 | 2.97E−03 | 636 | 14.5 | | 11.50 | |
| | BLI | 5.07E+05 | 1.48E−03 | 0.0019 | 2.91 | | 0.11 | 0.99 |
| ELB01104 H7 IgG4 D12 S228P/R409K/ H310A/H435Q | SPR | 2.44E+05 | 1.23E−03 | 1020 | 5 | 2.9 | 34.40 | |
| | BLI | 4.99E+05 | 7.44E−04 | 0.0028 | 1.49 | 2.0 | 0.31 | 0.99 |
| ELB01106 H7 IgG4 F04 S228P/R409K/ H310A/H435Q | SPR | 1.76E+05 | 7.21E−04 | 1010 | 4.1 | 3.5 | 8.55 | |
| | BLI | 4.53E+05 | 7.36E−04 | 0.0024 | 1.63 | 1.8 | 0.18 | 1.00 |

In Table 11, it is seen that the results obtained for anti-CD160/CD160 interaction measurement with a second technique (SPR) demonstrate, just like the measurements of affinity of these same antibodies by BLI, that the gain obtained for the H7 variants, regardless of the nature of the isotype (IgG4, IgG4 H310A-H435Q, IgG1 and IgG1 E345K), is always at least a 2-fold improvement in affinity for the recombinant CD160 compared with the corresponding H7, an Rmax that is two times higher, reflecting a better $k_{on}$, and a dissociation constant that is two times lower than the corresponding parental H7.

anti-CD160 tested (regardless of the isotype or the IgG format or the variant) specifically recognize human CD160 expressed recombinantly by the CHO-S cells.

In FIG. 1A, IgG1 variants bind more efficiently to the CHO-hCD160 transfectants than the H7 IgG1 (which results in a median fluorescence increased by a factor of 3 compared with H7 IgG1). This is true for the IgG1 or IgG E345K format. The presence of the E345K mutation in the Fc of the variants does not improve their binding to these cells.

In FIG. 1B, the IgG4 variants bind more efficiently to the CHO-hCD160 transfectants than H7 (which results in a median fluorescence increased by a factor of 2 compared with H7 IgG4 ELB01101 or with H7 IgG4 H310A-H435Q ELB01102), this being even in the presence of the H310A-H435Q mutations. Indeed, the presence of the H310A-H435Q mutations in the Fcs of the anti-CD160s does not impede their binding to their target, as can be seen when the binding is compared between ELB01101 and ELB01102.

The binding capacity of the anti-CD160 H7 antibody and of the H7 D12 variant in the IgG4, Fab and Fab-linker Fab format was evaluated during the labelling of surface CD160 expressed naturally on a clone of NK cell line (YT2C2), by measuring the percentage of cell labelled=percentage of binding (see FIG. 1C). For this, $2 \times 10^{+5}$ YT2C2 cells were labelled with increasing concentration of antibodies (from 50 nM to 0.39 nM) and also with the appropriate control isotype. These results were analyzed using the GraphPad Prism software for generating non-linear regression curves (Log(agonist) vs response, 3-parameter equations) and calculating the median effective concentrations ($EC_{50}$). In FIG. 1C, IgG4 variants ELB01103 and ELB01104 bind more efficiently to the YT2C2 cells than the H7 IgG4 ELB01101 (which results in a $EC_{50}$ increased by a factor of 10 compared with H7 IgG4). This is also true for the Fab-linker-Fab format ELB01132. By contrast Fab format ELB01122 bind less efficiently to the YT2C2 cells than the H7 IgG4 ELB01101 (which results in a $EC_{50}$ decreased by a factor of 2 compared with H7 IgG4). This is certainly due to the monovalency of the Fab format.

EXAMPLE 6

Effect of the Anti-CD160 Antibodies According to the Invention on the Inhibition of HUVEC Tube Formation and Characterization of the Induction of CD160 Expression on HUVECs Ten antibodies were evaluated for their effects on vascular tube formation induced by VEGF or FGF in a Cell Player GFP-AngioKit assay (Essen Biosciences). This set of samples comprises the Avastin anti-VEGF antibody and the Lucentis antibody fragment. Frozen human umbilical vein endothelial cells (HUVECs) pre-labelled with a fluorescent protein (Green Fluorescent Protein or GFP) using a lentiviral expression system were thawed and co-cultured with human dermal fibroblasts on six 96-well assay plates for 2 days. The antibodies and the reference agents (VEGF, FGF-2, control medium) were added to various wells at various concentrations and the assay plate was then placed in an IncuCyte live cell imaging system. Fluorescent and phase-contrast (10×) images were taken every 12 h for 10 days and analysed for the length of the tube and the number of branching points. The culture media (with antibody if required) and the assay supernatants were replaced every 2-3 days.

EXAMPLE 7

Evaluation of the Efficacy of the Subconjunctival Injection of the Anti-CD160 H7 Candidates in the IgG4 Format (ELB01101) in Comparison with Aflibercept (Eylea®) in a Corneal Neovascularization Model in the Rat A corneal neovascularization model was developed in the rat. This model in particular allows easy observation of the monitoring of the appearance of neovessels in the cornea, which enables an evaluation of molecules having anti-angiogenic properties, including the antibodies according to the invention.

The antibody batches were generated, produced, purified and qualified according to the process for preparing batches for intravitreal and subconjunctival injections.

Groups of 6-week-old male Lewis rats were used.

Induction of Corneal Neovascularization in the Rat $D_0$: Surgical intervention under an operating microscope is performed on one eye of each of the rats, after anaesthesia. For this, the cornea is entirely de-epithelialized by application of ethanol at 70° C., followed by an incision of the limbus, which leads to the appearance of corneal neovessels from D4.

Only the right eye is used. The animals are anaesthetized with an injection in the right femoral muscle of ketamine (Imalgene 500), 100 µl per rat and xylazine (Rompun 2%), 100 µl per rat. A drop of tetracaine is instilled in the right eye. The manipulations are carried out under an operating microscope. The neovascularization is induced by destroying the epithelium of the cornea by applying a "microsponge" soaked in 70% alcohol to the surface of the cornea. In parallel, a thickness of approximately 1.5 mm of conjunctiva is removed around the limbus with microscissors. An antibiotic ointment (Fucidine) is applied to the eye. The pupils are then kept closed for 4 days after suturing (5-0 silk thread). After 4 days, the pupils are opened by removing the threads; the change in the neovessels of the cornea is examined under an operating microscope on D4, D8 and D12 after anaesthesia.

Treatments 10 rats per group (except 3 for the IgG4 control isotype) are used in the following way:

$D_0$: The operation is performed on one eye of the animals, as described above;

$D_8$: Photos are taken and the animals are divided into 8 groups of 10 rats each, in order to be treated on the eye in which the operation was performed:

The animals are injected with the products subconjuctivally using a syringe fitted with a 29½ G needle (Myjector) on D4 and D8.

Group 1: subconjunctival injection of 50 µl of PBS (negative control),
Group 2: subconjunctival injection of 250 µg of Aflibercept® (Eylea) in 50 µl,
Group 3: subconjunctival injection of 500 µl of IgG4 control isotype in 50 µl,
Group 4: subconjunctival injection of 500 µg of H7 IgG4 antibody in 50 µl according to the invention On D8 and D12: Photos of the eyes on which the operation was performed are taken after observation under an operating microscope in order to evaluate the effect of the treatment on the neovascularization of the cornea. Samples of the sera and the vitreous humours are taken on D+12 post-mortem.

The rat eye photos (.JPEG) were analysed using software (Calopix, TRIBVN). The analysis was carried out blind, without knowledge of the group or of the timing of the photograph. The evaluation of the vascularization is determined using quantification software. The vascularization was estimated as being the surface area of the blood vessels relative to the total surface area of the eye analysed (that is to say the de-epithelialized area). The photos are reported and the % neovascularizations relative to the total surface area are reported in the graph of FIG. 2.

Results:

Photographs of the eye on which the operation was performed are taken on D0 and on 2 different days: D7 and D12. The photos taken show the change in the corneal neovascularization, in particular the development of the vascular density and of the length of the vessels up to D12 in the isotype control.

Figure 2:
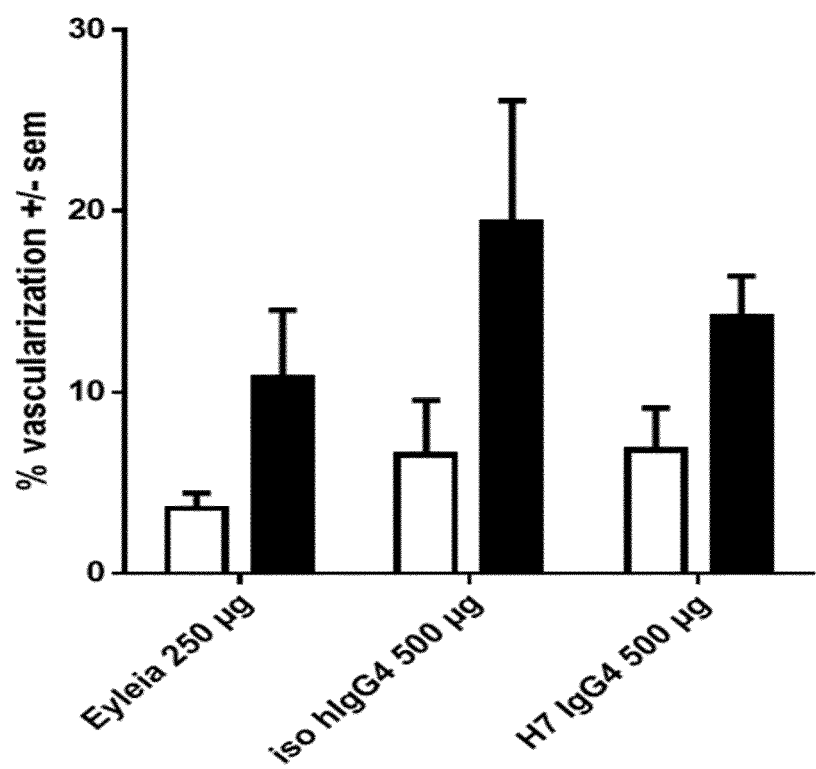
FIG. 2: Evaluation of the efficacy of an anti-CD160 antibody in the IgG4 format (ELB01101) over time in comparison with Aflibercept (Eylea®) in a model of corneal neovascularization in the rat. Mean and Error standard are reported on this bargraph. White bar % vascularisation at Day 8 and black bar % vascularisation at Day 12.

The results presented in FIG. 2 show a decrease in the vascular density in the animals treated with the H7 monoclonal antibody according to the invention, compared with the animals injected with a negative control, in this case the IgG4 control isotype.

It is also seen that the dose of H7 IgG4 (ELB01101), despite a weak cross-reactivity for rat CD160 (data not shown), reduces the corneal neovascularization in this rat model in a manner comparable to a dose of 250 μg of a high-affinity soluble receptor for VEGF, the fusion protein (Aflibercept®), an anti-angiogenic used for the treatment of age-related macular degeneration (ARMD). This was also obtained with the H7 antibody in the IgG1 N297Q format.

The H7 antibody, in the IgG4 and IgG1 N297Q formats, according to the invention thus has anti-angiogenic activity.

EXAMPLE 8

Comparison of the Systemic and Ocular Pharmacokinetic (PK) Profiles of Various Formats of Anti-hCD160 ELB's Candidates in Rabbits After Intravitreal and Intravenous Administrations with the Ones of Parental CL1-R2, of Bevacizumab and of Ranibizumab The objective of this study was to compare the systemic and ocular pharmacokinetic (PK) profiles of various formats of anti-hCD160 ELB's candidates (including the ELB011 candidates) with those of the parental murine IgG1 anti CD160 CL1-R2 and of bevacizumab. To screen for an optimized anti CD160 candidate that will have a good time of residence in the eye and the lowest systemic half-life, a PK study using 54 pigmented rabbits (HY79b strain) was performed. The same dose (0.5 mg) of item to be tested was administrated via intravitreal (IVT) or intravenous (IV) injections in rabbits, and seric antibody concentrations were determined by LC-MS/MS for ELB011 leads (and for ELB02104 and ELB02114 anti CD160 mAbs from the ELB021 program) or by using commercial ELISAs for CL1-R2 and for IgG and Fab comparators, here respectively the bevacizumab (Avastin) and the ranibizumab (Lucentis) in their marketed formulations. This allowed to modelize pharmacokinetic parameters after IV bolus of each candidate and thus to calculate output kinetic parameters for each drug.

Method for Intravitreal Injection (Tested Groups and PK Blood Samples)

The study of the pharmacokinetics (PK) of the various anti-CD160s and of their controls after a single administration of 500 μg by intravitreal (IVT) injection is carried out in New Zealand white rabbits The study was carried out with rabbits in good health (bacterial and viral status of the animal known, one sex) (KBL Charles River) (2750-3000 g of body weight, age at the beginning of treatment: 14-18 weeks). These animals were placed in a cage in the conventional care unit for one week before randomization and for 4 consecutive weeks during the study (the animals will be housed at 1 to 2 animals/cage). The experimental protocol was subjected to the ethics committee of the provider before beginning.

The experimental design of the experiment is described in Table 12. This experiment contains 8 groups of 3 rabbits/group including 6 different formats of anti-CD160 (see Table 12 below) at a concentration of 5 mg/ml with an endotoxin level of 0.5 EU/ml and 2 controls, bevacizumab (Avastin) and ranibizumab (Lucentis).

The administrations of drugs (50 μl/eye/administration) were performed by a bilateral injection of 250 μg of each drug in a final volume of 50 μl under general anaesthetic.

The rabbits were followed by a weekly monitoring of the clinical signs and of the body weight and by Ocular observations for ocular tolerance in order to search for macroscopic signs of ocular irritation (even minimal) and extensive ophthalmological examinations of the back of the eye (using slit lamp and indirect ophtalmoscope for the integrity of the characteristics of the head of the optic nerve, (retinal and choroidal) vascular network and RPE and Bruch's pigmentation membranes/coloration.

After the death of the animals, both eyes are enucleated and immediately frozen at −80° C. Before analysis, the frozen eyes are separated into three parts—the vitreous body, the aqueous humour, and the retina/choroid. The volume of the aqueous humour samples and of the vitreous samples (after homogenization and centrifugation) is measured. The frozen retina/choroid were weighed.

Approximately 0.5 ml of total blood samples from the central artery of the ear of the rabbits were taken in a tube without anticoagulant before administration (pre-dose T0) and after administration at 2 h, 6 h, 12 h, 24 h, 48 h (D2), 96 h (D4), 168 h (D7) and 336 h (D14). The serum was stored frozen until analysis. The serum samples were analysed to determine the anti-CD160 concentration.

Method for Intravenous Injection (Groups Tested and PK Blood Samples)

The experimental design of the experiment is described in Table 12. This experiment contains 10 groups of 3 rabbits/group including 8 different formats of anti-CD160 (see Table 12 below) at a concentration of 5 mg/ml with an endotoxin level of 0.5 EU/ml and 2 controls, bevacizumab (Avastin) and ranibizumab (Lucentis).

The administrations of drugs were performed by a single bolus intravenous injection of 500 μg in maximum 50-200 μl under general anaesthetic (for whole IgG or molar equivalent for the mAb fragment).

Approximately 0.5 ml of total blood samples were collected in a tube without anticoagulant before administration (pre-T0) and after administration at 5 min, 15 min, 30 min, 60 min, 2 h, 6 h, 12 h, 24 h, 48 h (D2), 96 h (D4), 168 h (D7) and 336 h (D14). The serum is stored frozen until analysis. The serum samples were analysed to determine the anti-CD160 concentration.

TABLE 12

Groups of the pharmacokinetic study in rabbits after an IV and IVT administration of 0.5 mg (0.19 mg/Kg)

| | Treatment group | Injection route and frequency | Number of animals | Injection route and frequency | Number of animals |
|---|---|---|---|---|---|
| 1 | ELB01101 (H7 G4) | 250 μg/ | 3 | 500 μg/ | 3 |
| 2 | ELB01103 (D12 G4) | 50 μl IVT, bilateral once on D0, | 3 | 100 μl bolus on D0 | 3 |
| 3 | ELB01104 (D12 H310A - R435Q) | | 3 | | 3 |
| 4 | ELB01122 (D12 Fab) | | 3 | | 3 |
| 5 | ELB01132 (D12 Fab linker Fab) | | 3 | | 3 |
| 6 | CL1-R2 | | 3 | | 3 |
| 7 | ELB02104 (D12 IgG1) | | none | | 3 |

TABLE 12-continued

Groups of the pharmacokinetic study in rabbits after an IV and IVT administration of 0.5 mg (0.19 mg/Kg)

| Treatment group | Injection route and frequency | Number of animals | Injection route and frequency | Number of animals |
|---|---|---|---|---|
| 8 ELB02114 (D12 IgG1 E345K) | | | none | 3 |
| 9 Bevacizumab | | | 3 | 3 |
| 10 Ranibizumab | | | 3 | 3 |

Bioanalysis of the Concentration of Each of the ELB011 and ELB021 H7-Derived Anti CD160 mAbs and Fragments Over Time in Rabbit Sera Samples The quantification of the different ELB011 anti human CD160 candidates (as intact IgG and IgG fragments) in rabbit serum samples following two routes of injection (intravenous (IV) vs intravitreal (IVT)), was performed using a high-performance liquid chromatography-tandem mass spectrometry (LC-MS/MS) method. The method development strategy aimed at obtaining one generic LC-MS/MS method suitable for the determination of the concentration of all ELB011 (and ELB021) drugs in rabbit serum. The samples were prepared by enrichment in drug of interest by Protein L affinity purification on magnetic beads, followed by reduction and alkylation using DTT and iodo-acetamide, prior trypsin digestion. The final extract was analysed via HPLC with MS/MS detection using positive ion electrospray. One tryptic peptide (ASQSIS-NHLHWYQQKPGQAPR residues 25-45 of SEQ ID NO: 14 including one CDR of the VL light chain) common to all anti CD160 (from ELB011 and ELB021 programs) based on H7 humanized candidate was monitored in the multiple reaction monitoring (MRM) method. The chosen peptide maps in the CDR region of the light chain, allowing the direct transfer of the assay to other pre-clinical matrices and possibly to analysis in human matrices. Then, the method was first qualified and then applied to the quantification of each compound in the rabbit sera.

Two other anti CD160 mAbs (ELB02104 and ELB02114, H7-A09 anti CD160 as IgG1 and hexameric IgG1E345K format respectively) for which only IV route on injection was tested were also quantified according to the same method.

Bioanalysis of the Concentration of CL1-R2, Bevacizumab and of Ranibizumab Over Time in Rabbit Sera Samples To compare pharmacokinetic parameters of H7 and variants of H7 to those of parental murine anti human CD160 CL1-R2, mouse IgG1 concentrations in rabbit sera were measured using enzyme linked immunosorbent assay (ELISA) using the commercial Mouse IgG1 ELISA Quantitation Set (Cat. No. E90-105, Lot No. E90-105-39 from Bethyl Laboratories) according to manufacturer's recommendations.

Ranibizumab and bevacizumab were chosen as comparators due to their molecular format (IgG1 and Fab respective). These compounds were dosed in rabbit sera using respectively Biovision's E4312-100 for ranibizumab (Lucentis)'s dosing and Biovision's K4254-100 for bevacizumab (AVASTIN)'s dosing.

Methods Used for Pharmacokinetic Parameters Analysis

For both injection routes, using a non-compartmental analysis, the following pharmacokinetic parameters were observed and calculated using measured seric concentrations:

For all serum concentrations time curves

C Max (µg/ml) (serum peak concentration occurring in a profile),

TMax (H) (Time of serum peak concentration),

TLag (H) (delay between drug administration and first observed serum concentration (when sufficient data)), AUC0-t obs (H.µg/ml) (Area under the serum concentrations time curve from 0 to Clast, using the log-trapezoidal rule), AUC0-inf obs (H.µg/ml) (Area under the serum concentrations time curve extrapolated from 0 to infinity (AUC0-t+Clast/Ke)), Clast (last observed conc), Elimination Ke (H−1) (slope of the terminal part of the serum concentration times-curve, obtained by log-linear regression (if sufficient data)), Terminal $T_{1/2}$ (H) (observed elimination half-life or terminal half-life, calculated as "$T_{1/2}$=−ln 2/Ke"), Vd (Distribution volume (L) after IV Bolus Vd=dose/(Ke×AUC0-inf) (IV Bolus only)), CL (Clearance (L/H) CL=Ke×Vd (IV Bolus only)).

For items that were injected by IVT only, additional parameters were evaluated like F % (AUC0-t) (Absolute bioavailability to the reference IV Bolus=AUC0-t Test×Ref dose/AUC0-t Ref×Test dose) and F % (AUC0-inf) (Absolute bioavailability to the reference form=AUC0-inf Test×Ref dose/AUC0-inf Ref×Test dose (If AUC0-inf measurable)).

Then, an IV bolus pharmacokinetic two-steps modelization was performed to calculate the parameters and rate constants of the kinetics in order to provide a compartmental model and information on the intrinsic disposition of the drug (distribution and elimination) (as described in Wagner, J. G. 1975). The disposition model of each candidate and the model dependent pharmacokinetic parameters of IV BOLUS doses are useful for the calculation of the IVT output after an IVT dose by deconvolution methods. This modelization was performed to determine the pharmacokinetic model in serum in each rabbit for each tested item.

At this stage, the kinetic of ocular elimination of drugs in the serum and the fraction of the dose eliminated in serum after IVT administration are calculated by a compartmental deconvolution method using the calculated IV bolus disposition model of the drug. If 2 or more compartments are observed, the Loo-Riegelman method (Loo J C, Riegelman S., 1968) is applied, if 1 compartment is observed, the Wagner Nelson (Wagner J G, Nelson E. 1968) is applied. The results are the cumulative quantity of drug which enter the serum (drug input) and the rate (drug input rate) versus the time. After an IVT administration of drugs the cumulative serum input profile is the ocular output profile and the rate is the output rate. In the meantime, the other following parameters could be also determined.

Tlag (H) The Lag Time (when sufficient data)

Ocular Output (mg): the total unchanged quantity of drug released in the serum

Output (% Dose): The % Dose of drug released in the serum (this is the absolute bioavailability of the ocular dose after IVT)

Output Time of 50% (±): Time to observe 50% of the injected dose which have entered the serum (graphic estimation)

Time of % Max (H): Time to reach the plateau of the cumulated drug output kinetic=the duration time of ocular residence of the drug
Output Rate (mg/H): rate of drug input in the serum
Max Output Rate (mg/H): Peak of the Output rate curve
Time of Max Output Rate (H):Time of peak.

ELB01104 (from 0.139 to 0.444 H). The mean distribution volume and clearance vary respectively from 0.05 to 0.33L and 0.005 to 0.1051 L/H.

As expected, anti CD160 fragments have reduced seric PK parameters after IV injection compared to IgG like

TABLE 13

Main observed pharmacokinetic parameters after a 0.5 mg (0.19 mg/Kg) dose administered intravenously (IV)

| TESTED ITEM | Molecular structure | $T_{1/2}$ Serum. day | Cmax. µg/mL | Cmax ratio/ ELB01101 | Tmax. Hour | mean AUC0-t H · micrg/ml | AUC ratio/ ELB01101 |
|---|---|---|---|---|---|---|---|
| ELB01101 | Anti CD160 IgG4 | 7.84 | 4.05 | 1.00 | 0.14 | 248.12 | 1.00 |
| ELB01103 | Affinity matured IgG4 | 2.68 | 3.67 | 0.91 | 0.44 | 163.64 | 0.66 |
| ELB01104 | Affinity matured IgG4 FcRn null mutation | 2.17 | 3.66 | 0.90 | 0.19 | 113.94 | 0.46 |
| ELB01132 | Fab-linker Fab | 0.19 | 3.46 | 0.85 | 0.08 | 13.28 | 0.05 |
| ELB01122 | Fab | 0.08 | 2.26 | 0.56 | 0.08 | 3.18 | 0.01 |
| ELB02104 | Anti CD160 IgG1 | 2.82 | 4.30 | 1.06 | 0.08 | 146.11 | 0.59 |
| ELB02114 | Affinity matured IgG1 E345K | 1.67 | 3.36 | 0.83 | 0.08 | 95.74 | 0.39 |
| Bevacizumab | anti VEGF human IgG1 | 3.08 | 6.91 | 1.71 | 0.39 | 464.60 | 1.87 |
| CL1-R2 | anti CD160 IgG1 murin | 2.27 | 6.98 | 1.72 | 24.00 | 541.39 | 2.18 |

TABLE 14

Main observed pharmacokinetic parameters in sera after a 0.5 mg (0.19 mg/Kg) dose administered intravitreally (IVT)

| TESTED ITEM | Molecular structure | Cmax, µg/mL | Cmax ratio/ ELB01101 | Tmax, days | mean AUC0-t H · micrg/ml | AUC ratio/ ELB01101 |
|---|---|---|---|---|---|---|
| ELB01101 | Anti CD160 IgG4 | 0.79 | 1.00 | 7.00 | 96.05 | 1.00 |
| ELB01103 | Affinity matured IgG4 | 0.67 | 0.85 | 3.33 | 83.91 | 0.87 |
| ELB01104 | Affinity matured IgG4 FcRn null mutation | 0.64 | 0.81 | 4.33 | 54.84 | 0.57 |
| ELB01132 | Fab-linker Fab | 0.11 | 0.14 | 2.00 | 9.87 | 0.10 |
| ELB01122 | Fab | 0.04 | 0.05 | 1.33 | 3.45 | 0.04 |
| Bevacizumab | human IgG1 | 1.74 | 2.21 | 168.00 | 303.26 | 3.16 |
| CL1-R2 | murine IgG1 | 0.57 | 0.72 | 104.00 | 70.76 | 0.74 |

As shown in tables 13 (IV route) and 14 (IVT route), the expected seric PK profiles (i.e. the main observed seric pharmacokinetic parameters) of ELB011's and ELB021's candidates after a 0.5 mg (0.19 mg/Kg) dose administered intravenously (IV) or intravitreally (IVT) and the ranking of their seric half-life (also noted $T_{1/2}$) are in accordance with the expected differences due to their corresponding formats (as described previously by Gadkar et al., 2015).

IV Bolus Observations and Modelization

Figure 3:
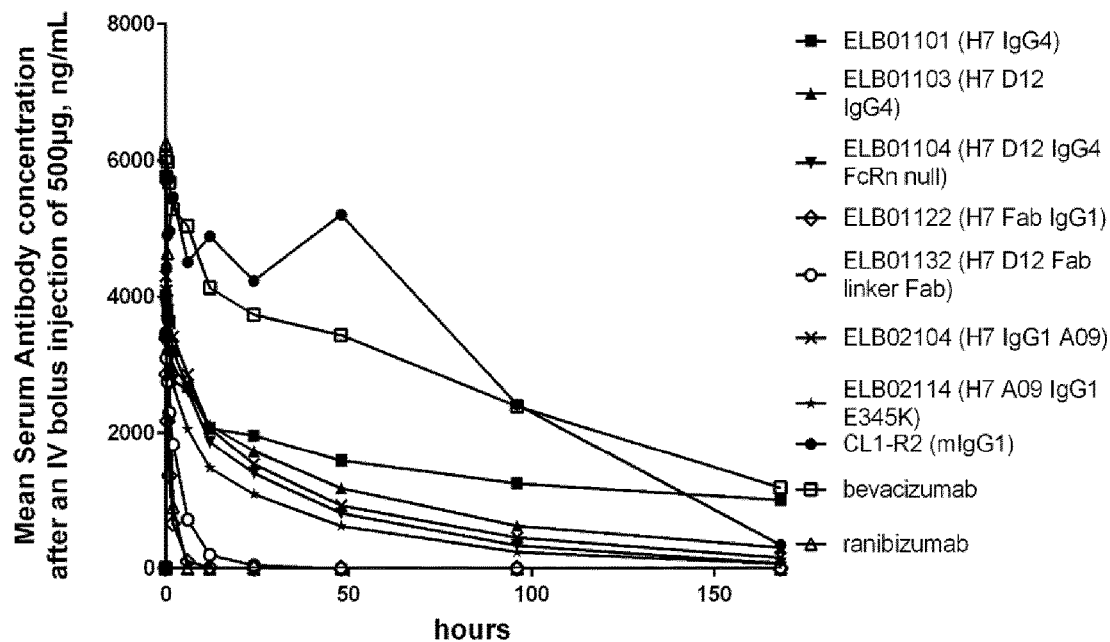
FIG. 3: Mean serum concentration of H7 and H7 variants in different IgG formats in function of time following two routes of administration, intravitreal (FIG. 3A) vs intravenous route (FIG. 3B), in rabbit compared to parental CL1-R2, bevacizumab and ranibizumab.
Figure 3:
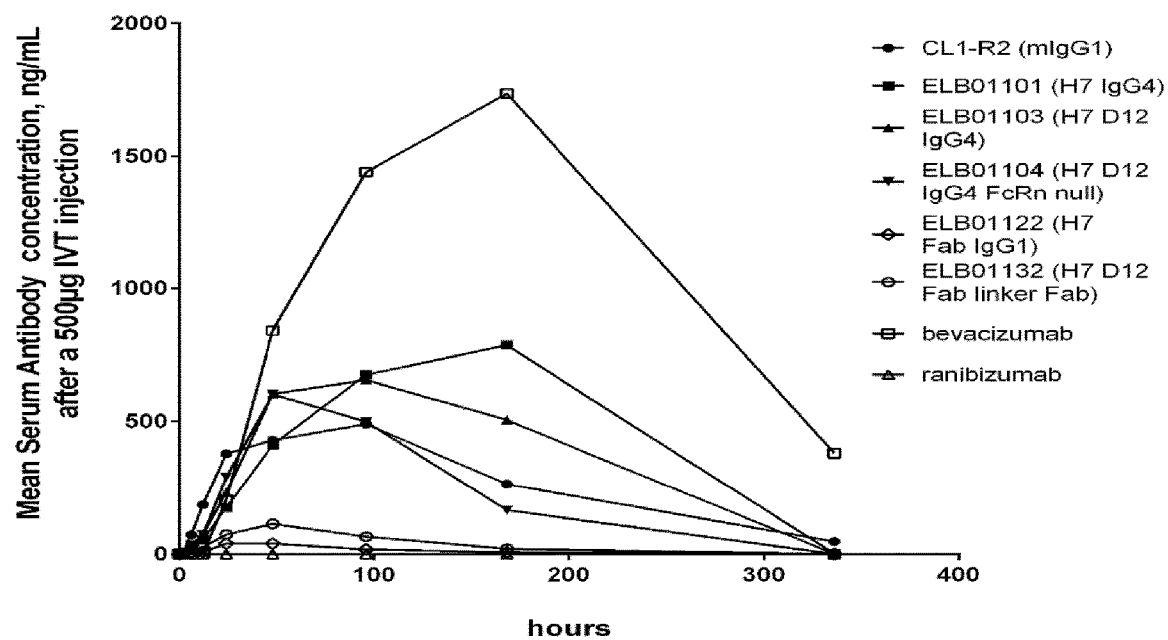

As seen in FIG. 3A, after an IV bolus, the serum concentrations of ELB01101, ELB01103, ELB01104, ELB01122, ELB01132, ELB02104 and ELB02114 decrease rapidly post injection (distribution phase), followed by a 2nd step of classical slow elimination phase ($T_{1/2}$ range: 52 to 188 H) excepted for ELB01122 and ELB01132 (1.9 and 4.6 H). As shown in table 13, the CMax (3,360 to 4,297 µg/ml) are observed at the first sampling time 0.083 H (2 minutes) for ELB01122, ELB01132, ELB02104 and ELB02114 but after a longest time for ELB01101, ELB01103 and formats. In particular, ELB01132's seric half-life seems to be slightly higher than the seric half-life of ELB01122.

Regarding pharmacokinetic parameters after IV administration of bevacizumab, when observed data are compared to literature data, the observed seric $T_{1/2}$ of bevacizumab in rabbit serum is quiet low compared to literature (3 vs 5.32 days, EMEA file for bevacizumab (AVASTIN)).

Regarding the ELB011 and ELB021 candidates in IgG formats, ELB01101 has the longest seric half-life, even longer than the one of CL1-R2 or bevacizumab, (Avastin). ELB01103 and ELB02104 have roughly the same seric half-life than bevacizumab, while ELB01104, ELB02114 and CL1-R2 have a reduced seric half-life compared to bevacizumab and ELB01103 and ELB02104. But, when AuC, Cmax and Tmax parameters are compared with those of bevacizumab and of CL1-R2, these parameters are significantly reduced with all the ELB011 candidates (and also with ELB021 candidates). Indeed, the serum concentrations of CL1-R2 and bevacizumab are not similar to the ones ELB011's & ELB021's candidates, CMax are highest: 6,980 and 6,091 µg/ml at 0.389 H for CL1-R2 and 24.7 H for bevacizumab (unexpected TMax corresponding to a slow infusion of bevacizumab). $T_{1/2}$, Vd and CL are respectively for CL1-R2 and bevacizumab: 54.5 and 74 H; 0.05 and 0.09 L; 0.0010 and 0.0009 L/H. This could due to the fact that bevacizumab and CL1-R2 have probably a lowest catabolism.

When pharmacokinetic parameters of ELB01101 (the non-affinity matured variant) are compared to those of the other affinity matured ELB011's and ELB021's candidates, the affinity maturation of anti CD160 mAb has decreased the serum half-life of these antibodies in rabbits. Indeed, the clearance in serum of all the affinity matured candidates is increased, this is shown in particular for ELB01103, ELB01104, ELB02104 and ELB02114 for which half-life in sera is significantly reduced compared to the one of ELB01101, and of bevacizumab. This faster clearance could be due to a CD160 driven specific biological process like for example an increase of anti CD160 mAb internalisation on CD160 positive cells in the blood. This should be checked in other species to be certain of the impact on clearance of anti CD160 due a high affinity for CD160.

ELB01103 and ELB02104 have a seric $T_{1/2}$ equivalent to the one of ELB01104 (the affinity matured variant with additional FcRn null mutations to prevent IgG recycling via neo natal FcRn receptor) rather than the one of the non-affinity matured native ELB01101. In the case of ELB01104, (as expected and previously described in (Olafsen, 2012) the FcRn mutations seem to have slightly reduced the seric half-life of ELB01104 compared to the one of ELB01103. But, as pharmacokinetic parameters of one ELB01101 with the same FcRn null mutations are not available, it is difficult to evaluate the impact of FcRn mutations alone. However, the PK profile differences between ELB01103 and ELB01104 versus ELB01101 are more important than the one between ELB01103 and ELB01104. The consequences of affinity maturation on ELB01104's PK parameters have more impact than the consequences of a reduced IgG recycling.

IVT Observations

As described in FIG. 3B, the serum concentrations increase slowly post injection in accordance to a slow output of the drugs from the eye, the highest profile level is observed after intravitreal administration of bevacizumab and the lowest after intravitreal administration of ELB01122 and ELB01132.

As reported in table 14, the mean CMax are in a range of 0.567 to 0.787 µg/ml for CL1-R2, ELB01103, ELB01104 and ELB01101 but lowest for ELB01122 and ELB01132 (0.041 and 0.114 µg/ml) and highest for bevacizumab (1.736 µg/ml). The TMax are observed between 48 and 168 H, the $T_{1/2}$ are indeterminable in all rabbits (no or insufficient data after the end of the ocular output to observe the serum elimination slope).

When administered intravitreally, all the ELB011 candidates, as well as the parental CL1-R2, have a lower systemic Cmax, a reduced Tmax and a reduced mean AuC compared to bevacizumab. As expected, the ELB011 anti CD160 fragments (ELB01132 and ELB01122) have reduced observed seric PK parameters compared to all the IgG formats injected intravitreally. These fragments are eliminated from the bloodstream more rapidly than all the IgGs based molecules (seric $T_{1/2}$ reduced at least by 30 fold compared to ELB01101). After an IVT injection, ELB01132's seric half-life seems again to be slightly higher than the seric half-life of ELB01122, as seen after IV injection.

After IVT injection, the ELB011 IgG candidates (ELB01101, ELB01103 ELB01104) have observed seric PK parameters close to the ones of CL1-R2 and are the ones expected for an intravitreally administered IgG format (as described in (Gadkar et al., 2015), for example). Tmax are the ones expected for each format, excepted for ELB01103. ELB01103 has an intermediate behavior (as shown by its PK parameters) between an IgG4 (ELB01101) and an IgG with no recycling via FcRn (ELB01104). When compared to literature, here again as observed after IV injection, data from Gadkar et al 2015, impact of FcRn mutations on Cmax, Cmax ratio$_{(Versus\ ELB01101)}$, Seric AuC o-t and Seric AUC ratio$_{(Versus\ ELB01101)}$ of ELB01104 is less pronounced than expected.

IVT Output Kinetics Determination

TABLE 15

Pharmacokinetic parameters in rabbits of ELB011 candidates after a deconvolution analysis of mean sera concentrations following both routes of administration of each item Pharmacokinetic parameters in rabbit after a 0.5 mg IVT (~0.19 mg/Kg) administration

| ELB0111 candidates | serum Cmax, µg/mL | Tmax serum, days | mean AUC0-t H · micrg/ml | max % of initial IVT dose in sera * | OCULAR OUTPUT (mg) | OUTPUT (% Dose) | Output Time of 50% Day | Time of % Max (Day) = time of residence in eye |
|---|---|---|---|---|---|---|---|---|
| ELB01101 | 0.787 | 7.00 | 96.05 | 19.67 | 0.341 | 68.150 | 5.000 | 7.000 |
| ELB01103 | 0.670 | 3.33 | 83.91 | 16.75 | 0.258 | 51.510 | 3.000 | 4.000 |
| ELB01104 | 0.637 | 4.33 | 54.84 | 15.92 | 0.346 | 69.260 | 2.667 | 3.667 |
| ELB01132 | 0.114 | 2.00 | 9.87 | 2.85 | 0.201 | 40.280 | ND | 2.000 |
| ELB01122 | 0.040 | 1.33 | 3.20 | 1.00 | 0.123 | 24.633 | ND | 1.667 |
| Bevacizumab | 1.736 | 7.000 | 303.260 | 43.400 | 0.420 | 83.970 | 5.000 | 7.000 |
| CL1-R2 | 0.565 | 4.333 | 70.760 | 14.125 | 0.176 | 35.150 | 7.000 | 4.333 |

TABLE 15-continued

Pharmacokinetic parameters in rabbits of ELB011 candidates after a deconvolution analysis
of mean sera concentrations following both routes of administration of each item
Pharmacokinetic parameters in rabbit

| | after a 0.5 mg IVT (~0.19 mg/Kg) administration | | after a 0.5 mg IV BOLUS (~0.19 mg/Kg administration | | |
|---|---|---|---|---|---|
| ELB0111 candidates | Max OUTPUT Rate (mg/H) | Time of Max Rate (Day) | mean AUC0-t H · micrg/ml | T½ Day, sera | Time residence In vitreous **/ T½ sera |
| ELB01101 | 0.004 | 2.000 | 246.123 | 7.837 | 0.893 |
| ELB01103 | 0.006 | 2.000 | 163.640 | 2.678 | 1.494 |
| ELB01104 | 0.009 | 1.667 | 113.943 | 2.173 | 1.687 |
| ELB01132 | 0.006 | 1.333 | 13.280 | 0.192 | 10.412 |
| ELB01122 | 0.004 | 1.333 | 3.177 | 0.081 | 20.513 |
| Bevacizumab | 0.004 | 2.000 | 464.600 | 3.082 | 2.271 |
| CL1-R2 | 0.003 | 0.667 | 541.387 | 2.272 | 1.908 |

* Assuming a mean rabbit blood volume of 125 mLs at Cmax and Tmax
** based on time of % max Based on the Cmax in serum after IVT injection and on an assumed mean rabbit blood volume of 125 mLs for rabbits, it is also possible to calculate the maximal concentration of product at Tmax and expressed it as the maximum percentage of initial IVT dose in sera at Cmax and at Tmax (Max % of initial IVT dose). This was calculated for each of the anti CD160 candidates that were injected by both routes and also for CL1-R2 and bevacizumab.

Regarding the calculated pharmacokinetic parameters summarized in table 15, after IVT injections of 0.5 mg, the ocular output corresponding to the calculated serum input of ELB01101, ELB01103, ELB01104, CL1-R2 and bevacizumab are respectively 0.341, 0.184, 0.346, 0.176 and 0.420 mg corresponding to 68, 55, 69, 35 and 84% of the vitreous dose respectively. The mean duration times of the ocular output (Times of % max) are respectively 168, 96, 88, 104 and 168 H.

First, when ELB011 IgG (and fragments as well) candidates are compared with bevacizumab, the systemic exposure is significantly lower for all the ELB011 candidates (max 19% with ELB01101 and 16.75% for ELB01103 for example) than for bevacizumab (43%). It means that, with ELB011 candidates, there is less amount of IVT injected product that went in the systemic than with bevacizumab. Indeed, the ocular output, the output dose and the maximum percentage of the initial IVT dose are very high for bevacizumab compared to all the ELB011 candidates.

Secondly, when ELB011's IgG candidates are compared to CL1-R2, ELB01101 and ELB01104 have a slightly higher total ocular output and output % of initial dose compared to ELB01103 and CL1-R2. Neither FcRn null mutations nor affinity maturation seems to have a major impact on ocular output and output dose. For ELB01103, there is less amount of product (less than 50% of the initial IVT total dose) that went into the serum compared to ELB01101 & ELB01104 (68 and 69%). ELB01103 is the IgG candidate that has a lower seric half-life than ELB01101 so even if some product goes into the sera, ELB01103 systemic product will be cleared 2 times faster than the ELB01101 systemic product.

In terms of output rate, the output rates ranged from 0.004 to 0.009 mg/h. ELB01104 has the highest output rate then ELB01103 and ELB01132 have the same output rate and finally ELB01101 and ELB01122 have the lowest output rate.

When ELB011 fragments candidates are compared to the other ELB011 IgG candidates, it is clear that, globally, elimination of ELB01132 and ELB01122, after an intravitreal administration, is clearly different from the one of anti CD160 in the IgG format. Both fragments have a similar PK profile of elimination from the eye (same total ocular output and almost the same output dose). Furthermore, as ELB01132 and ELB01122 are eliminated more rapidly than all the IgGs based molecules from the bloodstream, a very low content of any of these two products is found in the systemic compartment (less than a max % of the initial IVT dose of 2.85% at the Tmax). This is also the case for Lucentis for which no product was detected in our hand in any of the rabbit sera after an IVT injection of 500 µg in the same condition.

When ELB01132 and ELB01122 are compared together, ELB01132 is eliminated differently than ELB01122. In terms of elimination after IVT, ELB01122 is the fastest product to be eliminated from the bloodstream. Indeed, it has the lowest % of initial IVT dose that goes into the bloodstream and the lowest ocular output. There is a little bit more ELB01132 product that is eliminated from the eye, (the ocular output is two-fold the one of ELB01122). ELB01132 seems to go into the bloodstream a little bit more rapidly than ELB01122. ELB01132 has a longer $T_{1/2}$ of elimination (seric half-life) and this impacts the other PK parameters. 75% of the initial IVT injected dose seems to stay in the eye for ELB01122 vs 60% for ELB01132. However, it seems that the mean residence time in the eye of ELB01132 is a little bit better than the one of ELB01122. So, both fragments candidates offer a very favorable ratio of $T_{1/2}$ in the eye on $T_{1/2}$ in systemic, better than the one for IgG candidates, but they have a lower time of residence in the eye than the candidates in the IgG format.

Note: The drugs serum inputs from the deconvolution of ELB01132 and ELB01122 are less accurate than for the other ELB011 IgG candidates due to a lower number of timepoints with a detectable seric concentrations, due to a very short seric half-life, and due to an initial delay of product release from the eye.

Summary—Conclusion on All PK Parameters After IV & IVT Administrations for ELB011 and ELB021 Candidates The expected seric PK profiles (i.e. the main observed seric pharmacokinetic parameters) of ELB011's and ELB021's candidates after a 0.5 mg (0.19 mg/Kg) dose administered intravenously (IV) or intravitreally (IVT) and the ranking of their seric half-life (also noted $T_{1/2}$) are in accordance with the expected differences due to their corresponding formats (as described previously by (Gadkar et al., 2015).

There is no impact of the FcRn null mutations or of affinity maturation on the PK parameters in the eye.

ELB011 and ELB021 candidates have different seric PK parameters than CL1-R2 and bevacizumab with a faster clearance in the serum, but this should be checked in other species (mice and non human primates in dedicated studies).

Regarding seric $T_{1/2}$, the ranking is very similar to the one of time of residence in the eye (as described in Gadkar & al, 2015), ELB01101>>ELB01103~ELB01104>ELB01132~ELB01122. The surprise came from ELB01103. ELB01103 has a behavior closer to the an IgG4 with no FcRn binding than an IgG4. With the different anti CD160 formats, the % of intravitreally injected antibody that ends up in the systemic as well as the seric$T_{1/2}$, were massively reduced and systemic exposure after IVT of ELB011 candidates is equivalent to the one of CL1-R2 and lower than the one of bevacizumab.

The total ocular output and the output % of initial dose of IgG-like anti-CD160 ELB01101 and ELB01104 are high compared to the ones of ELB01103.

In terms of % of the dose that stayed in the eyes, ELB01122 is better than >ELB01132>ELB01103>ELB01104>ELB01101. In terms of output rate from the eye, the output rates ranged from 0.004 to 0.009 mg/h. ELB01104 has the highest output rate then ELB01103 and ELB01132 have the same output rate and finally ELB01101 and ELB01122 have the lowest output rate.

In terms of time of residence in the eye (See column Time of % Max in table 15) the ranking between ELB011's candidates is the following one: ELB01101>>ELB01103~ELB01104>>ELB01132~ELB01122.

Choice of the Leads to be Further Tested in In Vivo Preclinical Model.

Among the potential ELB011 candidates, two leads were finally chosen, one IgG fragment and one whole IgG to be compared in a dose efficacy study in the adequate NHP model.

Regarding the screen for an optimized anti CD160 candidate that will have a good time of residence and the lowest systemic half-life, on the left hand, the ratio Time of residence in the eye/$T_{1/2}$ sera, for the IgG-like mAbs, is better for ELB01104, then for ELB01103 and finally for ELB01101 (ELB01104>ELB01103>>ELB01101). But, on the other hand, for ELB01104, 70% of the initial dose goes into the systemic (and only 50% for ELB01103), i.e. there is less product that stayed in the eye for ELB01104 than for ELB01103. Thus, the final ranking between ELB011 candidates as IgG format is ELB01103>ELB01104>ELB01101.

For the Mab fragment choice, both fragments have a similar PK profile of elimination from the eye (same total ocular output and almost the same output dose). Both fragments candidates offer a very favorable ratio of $T_{1/2}$ in the eye on $T_{1/2}$ in systemic, better than the one for IgG candidates. It seems that the mean residence time in the eye of ELB01132 is a little bit better than the one of ELB01122. Finally, in terms of PK parameters and taking into account other developability parameters (requirement of avidity for an ideal CD160 binding and for questions of yield of production and quality of produced fragments) the recommendation was to select ELB01132 (Fab linker Fab) for further efficacy testing.

EXAMPLE 9

Pilot Study of Efficacy/Tolerability of Intravitreal Injection of the Anti-hCD160 H7 (IgG4 (ELB01101)) and H7 (IgG1 N297Q (ELB01111)) in a Model of Laser-Induced Choroidal Neovascularization in the Non-Human Primate (NHP) *Macaca fascicularis*

The objectives of this study were (1) to determine the ocular tolerance of two formats of anti-hCD160, H7 IgG4 (ELB01101) and aglycosylated H7 IgG1 (ELB01111), when they are administered via a single intravitreal injection in cynomolgus monkeys and (2) to evaluate the potential preventive effect of one of these isoforms on laser-induced choroidal neovascularization in a cynomolgus (*Macaca fascicularis*) monkey model.

Justification of the Model Choice, Route of Exposure for Test System and of the Number of Animals Safety and dose assessment for efficacy (preventive effect) was initiated in the most relevant NHP laser induced chNV model. Indeed, this animal model has an established track record as a predictor of pharmacologic efficacy of anti-neovascular drugs in humans having the neovascular, or wet, form of age-related macular degeneration.

The ocular route of exposure was selected because this is the intended route of human exposure.

The cynomolgus monkey was chosen as animal model for this study because it is a non-rodent species accepted for preclinical ocular toxicity tests by the regulatory bodies. The total number of animals to be used in this study is considered to be the minimum required to correctly characterize the effects of the test antibody. This study was designed such that it does not require a needless number of animals in order to achieve its objectives.

The ocular tolerability, the clinical parameters and the preventive effect of a single intravitreal injection of 1 mg per eye of the ELB01101 IgG4 mAb, of ELB01111 (tolerability only) or of control vehicle in laser-induced ChNV model were evaluated at Charles River (Senneville, Canada). All the procedures used for this NHP model study are the standard procedures from Charles River and are briefly described below. Some minor changes were made compared to the initial monkey model protocol initially developed by Ryan S J, 1982.

Study/Experiment Scheme

Animals and Animal Farming Conditions

A total of 17 male cynomolgus monkeys (from 2 to 3 years old) were received and weighed between 2.7 and 3.2 kg at the initiation of the dosage. A minimum acclimatization period of 4 weeks was allowed between the reception of the animals and the beginning of the treatment in order to accustom the animals to the laboratory environment. The animals were housed socially (up to 3/group/cage) in stainless steel cages equipped with an automatic watering valve. Temperatures of 20° C. to 26° C. with a relative humidity of 30% to 70% were normally maintained. A cycle of 12 hours of light/12 hours of darkness was maintained. The food was provided in amounts appropriate to the size and age of the animals (PMI Nutrition International Certified Primate Chow No. 5048 was provided twice a day). The water after treatment by reverse osmosis and ultraviolet radiation was freely available for each animal via an automatic watering system. The monkeys were used in accordance with the ARVO declaration for the use of animals in ophthalmic research.

Experimental Design

As described in table 16, in a first phase, tolerability (global and ocular tolerance) of intravitreal administration of 1 mg of the H7 variant in two IgG formats (IgG4 and IgG1 N297Q) was compared in 3 non laser induced eyes of monkey.

In the second phase, the efficacy of the less toxic isoform or, if equivalent tolerability, the H7 in its IgG4 format (ELB01101) in the laser induced ChNV model was assessed.

TABLE 16

Summary of the experimental scheme phase 1 Tolerability and phase 2 Efficacy/extended tolerability

| Group No. | Material tested RE | Material tested LE | Dose (mg/eye) | Dose volume (µL/eye) | Dose concentration (mg/mL) | Number of animals Males |
|---|---|---|---|---|---|---|
| Phase 1 1 | H7 IgG4 | H7 IgG1 aglyc. | 1.0 | 50 | 20 | 3 |
| Phase 2 2 | PBS for injection | | 0 | 50 | 0 | 6 |
| 3 | H7 IgG4 | | 1.0 | 50 | 20 | 6 |

RE: right eye, LE: left eye.

Preparation of the Items to be Tested

On the day of use, the items to be tested (without aggregates and with a very low endotoxin content (<0.025 EU/mg) (see Table 17)) were prepared at 20 mg/mL by dilution with the reference product (PBS) at concentrations appropriate for meeting the dosage requirements.

TABLE 17

Identification of the items and carrier control tested

| | Test item 1 (anti-CD160 format 1) | Test item 2 (anti-CD160 format 2) | Reference item/carrier |
|---|---|---|---|
| Identification | H7 IgG4 | Aglycosylated H7 IgG1 | PBS for injection |
| Batch No. | Prod 2 28 Dec. 2015 | Prod 4 Mar. 2016 | * |
| Description | Liquid | Liquid | Liquid |
| Purity | 99.5% | 99.5% | n/a |
| Concentration | 22.7 mg/mL | 22.7 mg/mL | n/a |
| Endotoxin level (Endosafe ®-PTS ™; Charles River) | <0.5 EU/mL <0.025 EU/mg | <0.5 EU/mL <0.025 EU/mg | <0.5 EU/mL |
| Storage conditions | 2° C. to 8° C. | 2° C. to 8° C. | 2° C. to 8° C. |

Parameters Monitored

The following parameters were evaluated during this study: mortality and clinical signs, body weight, change in body weight, appetite, ophthalmology, fluorescein angiography, macroscopic pathology and immunohistochemistry.

Procedures in Force, Observations and Measurements

The mortality/moribondity controls were normally carried out twice a day, once in the morning and once in the afternoon, throughout the study. Detailed examinations were carried out each week for the dosage and observation periods. The individual body weights were measured each week. The individual evaluation of the feeds was evaluated daily by visual inspection of the general appetite.

Ophthalmological examinations were carried out during phase 1, once in pre-study and on days 2, 5 and 7, and during phase 2, once in pre-study after the induction of laser-induced CNV, on day 1, day 9 and again on day 28.

Ophthalmoscopic and biomicroscopic examinations (slit lamp). The examinations were carried out by a certified veterinarian-ophthalmologist. The mydriatic drops used were tropicamide at 1%. A sedative, Ketamine® HCl for injection, USP, was administered by intramuscular injection after an appropriate fasting period.

Imaging Procedure

The development of active ChNV lesions was assessed by fluorescein angiography (FA), once prestudy before injury and on days 14 and 29 after laser injury. The ChNV lesions defined by the individual laser spots on the still images from days 14 and 29 were evaluated for leakage semi-quantitatively.

Fluoro-Angiograms

During efficacy evaluation phase 2, imaging data (fluorescein angiographies or fluoro-angiograms) were determined on day 1 (after laser, in pre-dose) and were collected again on days 14 and 29 post-photocoagulation as follows:

Procedure: mydriatic drops (1% tropicamide) were applied to each eye at least 25 minutes before the test. The hydration of the eyes was maintained by frequent irrigation with a saline solution. The animals receive an intramuscular injection of a sedative cocktail of ketamine (5 mg/kg), glycopyrrolate (0.01 mg/kg) and dexmedetomidine (0.01 mg/kg), and were then intubated with an endotracheal tube in order to administer an isoflurane/oxygen mixture. Once the angiography is finished, the animals receive, if necessary, an intramuscular injection of 0.1 mg/kg of atipamezole, a reversal agent for dexmedetomidine. The simple and/or real-time retinal images in the free infrared and/or red modes were obtained so as to act as reference images for the angiographies. 1.0 ml of 10% injectable fluorescein sodium U.S.P. was administered by rapid intravenous injection (cephalic or saphenous vein), followed by a water flush of 0.5 ml of saline solution. The fixed images were recorded for the two eyes at least 2 minutes and at the latest 5 minutes after the fluorescein injection. In addition, the fixed images of the two eyes were recorded at least 8 minutes and at the latest 11 minutes after the fluorescein injection. In order to ensure that the data are masked, the fluoro-angiography images were identified by an animal arrival number, and not by the number of randomized animals. The levels of severity of the lesions (grades corresponding to each individual laser lesion) were evaluated on the fixed images by the extent of the fluorescein leakage on a scale of 0-4 by 2 masked and experienced independent readers, who subsequently determine a consensus score using the following scale: grade 0 no leakage, grade 1 minimal leakage, grade 2 slight leakage, grade 3 moderate leakage (semisolid to solid hyper-fluorescence generally remaining within the boundary of the laser-induced defect region), grade 4 substantial leakage (solid hyper-fluorescent region extending beyond the boundary of the laser-induced defect region).

The total number and the % of relevant clinical lesions (grades 3 and 4) were counted totalled. Day 1 images were used for confirmation of procedure and laser spot formation).

The number of clinically relevant lesions were defined by the combination of the lesions of grade 3 and 4.

It is also possible to express the incidence on clinical relevant lesions by the incidence rate and the incidence rate ratio as defined in (Krzystolik et al., 2002). The incidence rate was defined as the number of clinically relevant lesions (that occurred during a given interval) divided by the total number of laser induced lesions/spots. Incidence rate could be also expressed in percentage. Then they calculated the incidence rate ratio (IRR) that referred to the ratio of incidence rate of clinically relevant lesions in the prevention eyes to the incidence rate in control eyes. An IRR of 1 would signify no difference between incidence rates. A IRR number much smaller than 1 would indicate a reduction in the incidence of clinically relevant lesions in the prevention group vs control group.

Immunohistochemistry by von Willebrand (vwf) Labelling

Following euthanasia, the eyes were enucleated and the vitreous humor was collected and placed on dry ice followed by storage in a freezer set to maintain −80° C. Remaining tissue from the left eyes from all phase 2 animals was used for immunohistochemistry analysis. The choroid membranes of the specified left eyes were prepared, mounted as "flat mount" and were stained with von Willebrand factor (vWF) by a IHC study. Briefly, flat mounts were washed in PBS+1% Triton buffer at least 5 minutes 3 times between each step, blocked in 1% BSA in PBS+1% Triton+0.1% sodium azide for 30 minutes, submitted to a rabbit polyclonal to von Willebrand Factor (1/200 of ab6994, Abcam) or to a negative Reagent Control (1/350×0936 Dako/NR-bIgG target for 48 h at 4° C., and finally to a AlexaFluor 488 coupled goat anti-rabbit IgG (A11008/Life Technologies) overnight at 4° C. The laser spot lesions treated or not by the anti-CD160 was individually evaluated semi-quantitatively for positive vWF staining, and was given a score of 1, 2 or 3 based on the size and nature of the lesion as compared to the visual field at 20× objective magnification. A further analysis using a confocal microscope was performed to confirm the nature of the lesion if needed.

The laser lesions were evaluated individually in a semi-quantitative manner for positive staining of vWF and a score was given to the size and to the nature of the laser lesion. The lesion was characterized on whether the spot lesion was open and had a central choroidal scar or was completely covered by RPE scar. A grading of minimal (1) for presence of spot fluorescence, mild (2) for presence of vWF-positive blood vessels/capillaries and moderate (3) when the amount of blood vessels was more than average in the areas of interest, center and periphery of the spot. The presence of vWF-positive vessels was evaluated separately in the center of the laser spot and around its periphery.

Blood Samples for Future Examination

The monkey blood was taken by femoral vein puncture:
for tolerance phase 1: before the beginning of the treatment and on days 1, 2, 3, 6 and 7;
for efficacy phase 2: before the beginning of the treatment and on days 1, 2, 3, 6, 12 and 28.

The samples were gently mixed and maintained under ambient conditions until centrifugation, which was carried out as soon as possible. The samples were centrifuged according to standard procedures. The resulting serum was separated, transferred to uniquely marked transparent polypropylene tubes and immediately frozen on dry ice and transferred to a −80° C. freezer. The possible subsequent examinations include measurement of the anti-CD160 antibody concentration in the systemic compartment after IVT injection.

Terminal Procedure

Animals surviving until scheduled euthanasia were fasted overnight before their scheduled necropsy. Prior to transportation from the animal room to the necropsy area, a sedative (Ketamine HCl for Injection, U.S.P.) were administered by intramuscular injection. Animals underwent exsanguination by incision of the axillary or femoral arteries following anaesthesia by intravenous injection of sodium pentobarbital.

Tolerance to the IVT Injection of the Anti-hCD160 in Two Formats (H7 IgG4 (ELB01101) and H7 IgG1 N297Q (ELB01111)) in the Cynomolgus Eye.

Topical antibiotics (tobramycin at 0.3%) were applied to the two eyes twice on the day before the treatment, after the injection and twice on the day following the injection.

Before the dosage regimen, the phase-1 animals for evaluating tolerance received an intramuscular injection of a sedative cocktail of ketamine (5 mg/kg) and of dexmedetomidine (0.01 mg/kg) followed by an isoflurane/oxygen mixture through a mask, judged necessary to maintain the anaesthesia. After completion of the dosage procedure (if judged to be necessary), the animals received an intramuscular injection of 0.1 mg/kg of atipamezole, which is a reversal agent for dexmedetomidine, if necessary.

During a first phase, the tolerance to the intravitreal (IVT) injection of 1 mg of each of the anti-hCD160 H7 IgG4 and H7 IgG1 N297Q was verified by injection into 3 monkey eyes (H7 IgG4 in the right eyes and H7 IgG1 N297Q in the left eyes).

The anti-CD160 H7 IgG4 antibody and the reference carrier control were administered by a veterinarian-ophthalmologist to the appropriate animals by bilateral intravitreal injection on day 1. The target dose volume for each animal was 50 µl/eye.

The phase-1 doses were administered using a 1 ml syringe and a 30-inch needle of ½ inch. During phase 1, H7 IgG4 was administered into the right eyes and aglycosylated H7 IgG1 N297Q was administered into the left eyes.

Demonstration of the Efficacy by the Preventive Effect on Laser-Induced Choroidal Neovascularization of the IVT Injection of H7 IgG4 Compared with the Carrier (PBS).

In two groups of 6 male cynomolgus monkeys (*Macaca fascicularis*) (1.5 to 3.5 years old, weighing from 1.5 to 6 kg), the induction of the choroidal neovascularization (CNV) was carried out as follows. Before ophthalmic washing, mydriatic drops (benzalkonium chloride (Zephiran™)) were applied to each eye before any procedure.

The (efficacy) phase-2 animals were anaesthetized just like those of the tolerance phase (see previous section).

The anti-CD160 H7 IgG4 antibody and the reference control carrier were administered to the appropriate animals on day 1. On day 1, they are injected by a veterinarian-ophthalmologist by bilateral intravitreal IVT injection of 50 µl at 20 mg/ml/eye of H7 IgG4 (the isoform selected after phase 1) or 50 µl/eye of the carrier. The target dose volume for each animal was 50 µl/eye with 1 mg of compound. The phase-2 doses were administered using an Exelint U-100 0.5 cc insulin syringe with a needle of calibre 29×½ inch. A topical antibiotic was instilled in each stated eye after the administration of the dose.

Procedure for Laser Induction of Choroidal Neovascularization (ChNV)—Phase 2

On day 1 of phase 2, before the ChNV procedure, mydriatic drops were applied to both the eyes. For the lesion laser-induction phase or before the intravitreal (IVT) injections, the animals receive an intramuscular injection of a cocktail of sedative ketamine (5 mg/kg), of glycopyrrolate (0.01 mg/kg) and of dexmedetomidine (0.01 mg/kg), and are then intubated with an endotracheal tube in order to administer the isoflurane/oxygen mixture for maintaining the anaesthesia, as was appropriate, and the animals were anaesthetized with a cocktail of ketamine (5 mg/kg). After the dosage procedure (as deemed necessary) is finished, the animals receive an intramuscular injection of 0.1 mg/kg of atipamezole, which is a reversal agent for dexmedetomidine, if deemed necessary. The animals have also been divided up into treatment groups and randomized by weight.

During the anaesthesia, on day 1, the laser treatment is carried out by generating 9 lesions per eye concentrically with respect to the fovea, with 1 lesion in the macular zone and 8 lesions in the perimacular zone between the major vessels of the retina. The laser lesions with an initial lesion size of 80 μm were created using an 810 nm diode laser at an initial power of 300 mW and a duration of 0.1 sec. So, a total number of 108 laser sites/group was evaluated for each treatment (6 animals/group, 2 eyes/animal, 9 sites/eye by items to be tested). The laser treatment was carried out reproducibly and verified by the appearance of small bubbles of vapour in the retina, characteristic of the rupture of the Bruch's membrane. No lesion was directly generated on the fovea. The laser parameters were adjusted as required in order to ensure rupture of the Bruch's membrane (correlated with the bubble formation) and are documented in the study data. All the notable events, such as retinal haemorrhage, were documented for each laser lesion. The eyes were kept hydrated with a saline and/or 1.0% sodium carboxymethylcellulose solution during the procedure, if necessary. Both the eyes were examined by slit-lamp biomicroscopy and/or indirect ophthalmoscopy after each treatment had finished, in order to confirm the position and the appearance of the dose and to document any abnormality caused by the administration procedure.

Analysis of Results

Tolerance Results, Summary:

Mortality and Clinical Signs

Clinical and ophthalmic examinations showed that there were no treatment-related effects on hemorrhages or alteration of body weights or macroscopic findings others than some that they were considered as incidental or procedure-related and typical of laboratory-housed primates. There was no effect linked to the treatment on body weights or gains in body weight. There was no effect linked to the treatment on body weight and there were no macroscopic results. Very slight vitreal opacities were observed in animals receiving H7 IgG1 N297Q, on day 28. They were not considered to be clinically important and such changes are commonly observed using the intravitreal administration route.

Ocular Tolerance—Ophthalmological Observations

Some minor secondary observations were recorded at pretreatment; however, all the animals were judged to be capable of taking part in the study. During phase I, only minor changes were observed after the administration of the dose. A small number of cells was noted in the vitreous and anterior chamber in 3/6 eyes (No. 1002 and 1003).

In phase II, laser exposure resulted in similar procedure-related ocular changes in all treated eyes, which included retinal scarring, hemorrhages, and foveal hemorrhages. The chorioretinal hemorrhages improved over time and had resolved in most eyes by day 28. Very slight cell-like opacities in the anterior portion of the vitreous were noted on day 28 in 9 on 12 eyes given 1 mg H7 IgG4 (ELB01101). Control animal No. 2004 given D-PBS was also noted with these cells bilaterally on days 9 and 28.

Efficacy of the IVT Injection of H7 IgG4 Assessed by the Preventive Effect on Laser-Induced Choroidal Neovascularization Analysis of the Fluoro-Angiography Results On day 1, the eyes of all the animals were successfully subjected to a scheme/design of 9 laser lesions for evaluating the choroidal neovascularization (CNV). Although some animals were noted with more than 9 lesions, only 9 lesions were evaluated.

As can be seen on the results summarized in FIG. 4 and below in Table 18, when considering the number of clinically relevant lesions (grade 3: moderate leakage and grade 4: substantial leakage; combined), there was a greater number of these lesions in the vehicle group on Days 14 and 29. At Day 14, there was a slight effect of the of IgG4 H7 (ELB01101) in the reduction of ChNV compared to the vehicle control. Following the evaluation of the Day 29 lesions, the difference was more marked in favour of the animals treated with the anti-CD160 H7 IgG4.

Indeed, on day 29, the animals receiving (ELB01101) exhibited a smaller number (13) of clinically relevant lesions (grade 3: moderate leakage and grade 4: significant leakage, combined) compared with the vehicle (PBS) group (25). The incidence of clinically relevant lesions relative to the total number of laser lesions was 12% in the eyes administered with H7 IgG4 compared with 23.1% for the vehicle group. When considering the number of clinically relevant lesions, there was a higher number of these lesions in the PBS group on days 14 and 29.

As reported in Table 18, it should be noticed also that there were a higher number of grade 0 lesions at day 14 and a higher number of grade 1 and 2 at day 29 for ELB01101 than for the vehicle indicating that in addition to a preventive effect on some large lesions, for other minor lesions, ELB01101 seems to have delayed the lesion progression.

TABLE 18

Impact of the vehicle control or H7 IgG4 treatments on the grades of the ChNV laser-induced lesions observed in monkey eyes

| Day | Laser lesion grades | PBS number of lesions (%/108 total lesions evaluated) | H7 IgG4 number of lesions (%/108 total lesions evaluated) |
|---|---|---|---|
| 14 | 0 | 2 (1.9%) | 11 (10.2%) |
|  | 1 & 2 | 89 (82.4%) | 86 (79.6%) |
|  | 3 & 4 | 17 (15.7%) | 11 (10.2%) |
| 29 | 0 | 4 (3.7%) | 4 (3.7%) |
|  | 1 & 2 | 79 (73.1%) | 91 (84.3%) |
|  | 3 & 4 | 25 (23.1%) | 13 (12.0%) |

When incidence rate and incidence rate ratio are calculated for this study (as defined in (Krzystolik et al., 2002)), at Day 29, the incidence rate (IR) of clinically relevant lesions relative to the total number of laser spots was 0.12 (13 out of 108) or 12% (in percentage) in eyes administered with ELB01101 compared to 0.231 (25 out of 108) or 23.1% (in percentage) for the vehicle group, corresponding to an incidence rate ratio (IRR) of 0.519

Evaluation of the Laser Lesions by von Willebrand Factor (vWF) by Immunohistochemistry on NHP Tissues The laser lesions were evaluated individually in a semi-quantitative manner for positive staining of vWF and a score was given to the size and to the nature of the laser lesion A minimal classification was used
(1) for the presence of fluorescent labelling, slight
(2) for the presence of vWF-positive blood vessels/capillaries, moderate
(3) when the amount of blood vessels was greater than the average in the zones of interest, centre and periphery of the lesion.

The average score for vWF-positive staining was slightly higher (approximately 10%) in the groups receiving H7 IgG4 at the centre of the laser lesion, whereas the control group had a slightly higher score (approximately 6%) at the periphery of the lesions compared with the treatment alone.

Point Lesion Score

At a magnification of 20×, the point of laser lesion received a score of 1, 2 or 3 depending on the size of the lesion relative to the visual field and the lesion was characterized in that the point lesion was open, or had a central choroidal scar or was completely covered with RPE scar.

An open lesion signifies that there is an absence of coverage of the lesion by the Bruch's and RPE membranes. A choroidal scar is characterized by the presence of dense tissue aggregates, frequently at the centre of the site which appears fibrous and has a high background fluorescence. Likewise, the RPE scar refers to an altered conjunction of RPE cells or of aggregates with a central fine fibrous structure with a high background fluorescence. Just as with the vWF fluorescence results, the lesion size score in the groups treated with H7 IgG4 was not very different from the controls.

However, if the appearance of the lesion is considered by evaluating the state of coverage of the lesion point by the RPE, its opening and the presence or absence of choroidal scar, the groups treated with H7 IgG4 had a higher total number of laser lesions (32 to 16 lesions) completely covered by healing with RPE membrane, whereas the control groups had a higher number of open lesions with or without central scar (26 to 19 lesions) (Table 19). This suggests a higher number of healing points in the groups treated with H7 IgG4, on the condition that there was no difference during the initial induction of the laser lesion. No recording was made for animal No. 2101 because the integrity of the coverage of the lesion was affected during the removal of the retina and of the attached RPE membrane.

Figure 4:
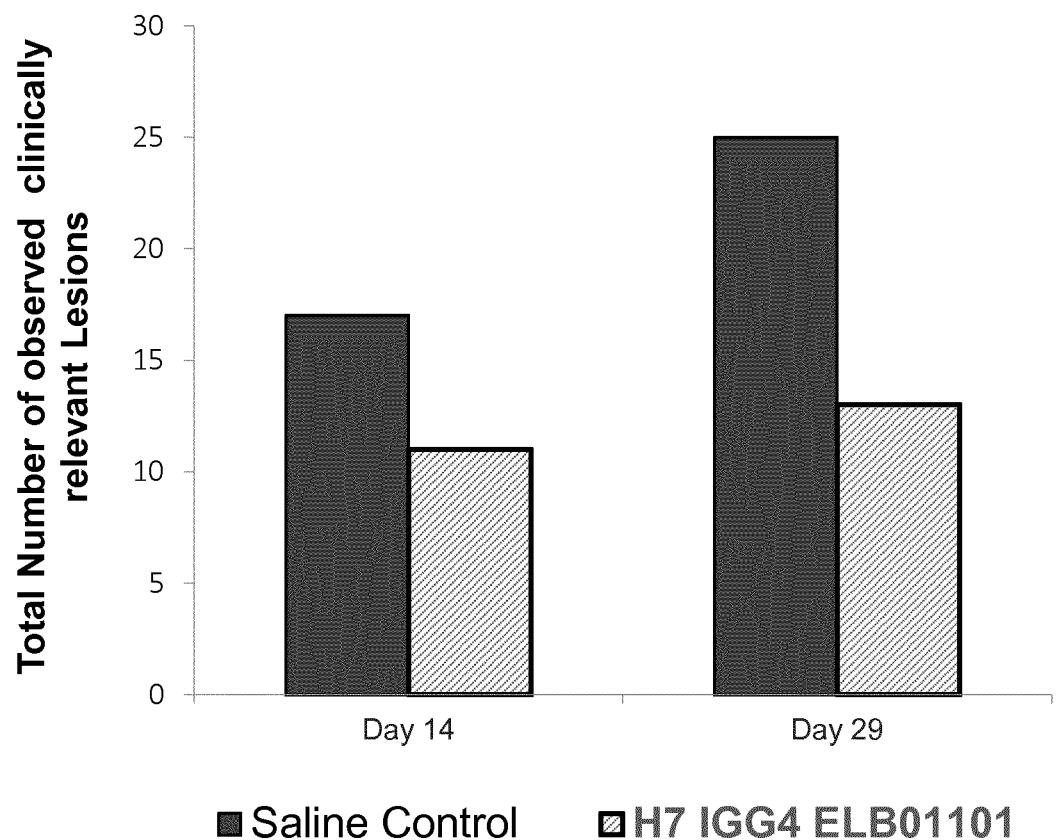
FIG. 4: Incidence of the anti-CD160 H7 IgG4 (ELB01101) on the total number of clinically relevant lesions by occasion (grades 3 and 4) in a monkey model of laser-induced choroidal neovascularization (combined score of grades 3 and 4/108 laser impacts). The total number of laser-induced lesions was 108 (corresponding to 12 eyes with 9 impacts per eye) for the animals treated with the anti-CD160 (H7 IgG4 ELB 01101) or with the carrier control.
Figure 5:
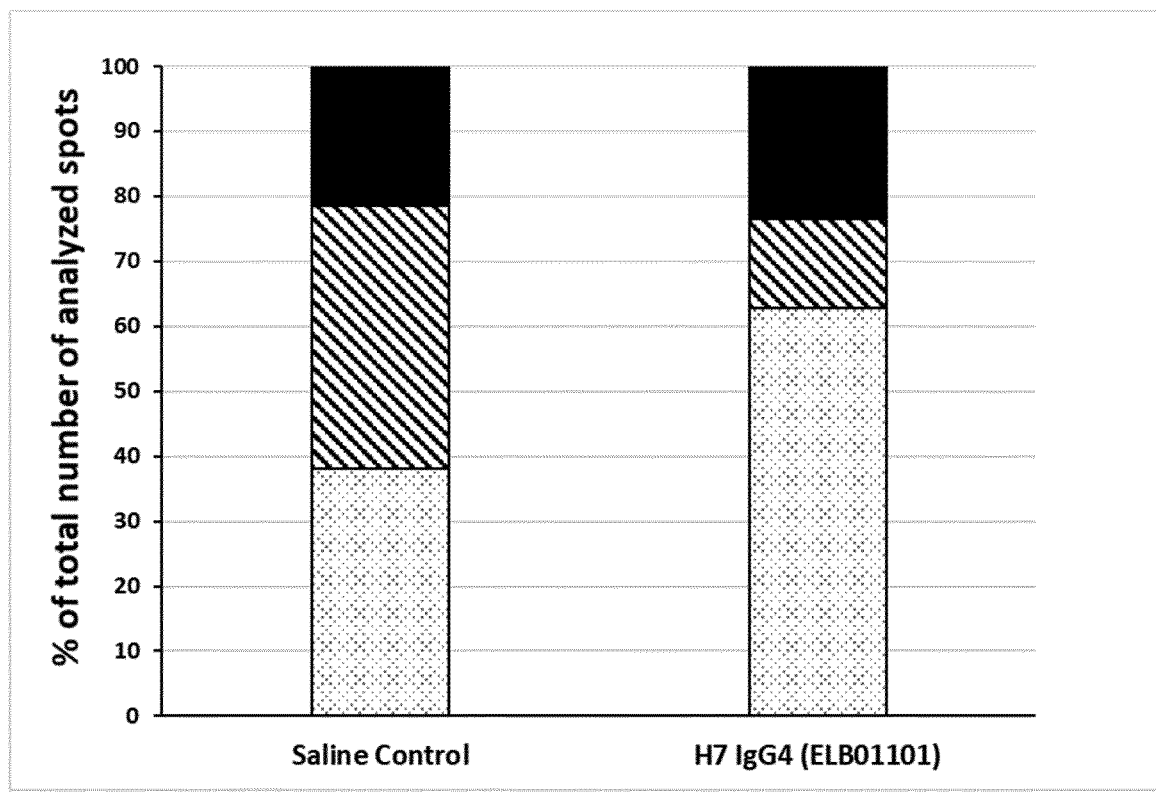
FIG. 5: Impact of the anti-CD160 H7 (ELB01101) on scar wound healing of laser-induced lesions in a monkey model of choroidal neovascularization. The state of healing and the opening of the lesions were individually estimated by immunohistochemical analysis after labelling with an antibody directed against von Willebrand factor. The percentage (%) of spots during healing (that is to say covered with the RPE membrane) in comparison with the percentage (%) of open spots with or without healing is represented as bargraphs. The % of Open spots with central choroid scar is represented as plain black bars, % of open spots without central choroid scar is represented as black diagonal bars, and % of in healing spots (Spots covered with RPE scar) is represented as white pigmented bars on the graph.

Summary:

As is seen in FIGS. 4 and 5 and in Tables 18 and 19, the efficacy and the preventive effect on laser-induced choroidal neovascularization of the IVT injection of H7 IgG4 compared with the carrier (PBS) were demonstrated as follows.

On day 14, an effect of IgG4 H7 in the reduction of the choroidal neovascularization compared with the PBS control was apparent. On day 29, the difference was even more marked in the case of the animals treated with H7 IgG4. On day 29, the incidence of clinically significant lesions relative to the total number of laser lesions was 12% in the eyes administered with H7 IgG4 compared with 23.1% for the PBS group. Taking into consideration the combined number of clinically relevant lesions (grade 3: moderate leakage and grade 4: significant leakage), there was a greater number of these lesions in the PBS group on days 14 and 29 as can be seen in FIG. 4.

As is seen in FIG. 5, when evaluating the retinal pigment epithelium (RPE) coverage status of each spot lesion using vWF IHC (as shown in FIG. 5), spot sizes cores were not different between ELB01101-treated and controls animals. The administration of H7 IgG4 was associated with a vascularization score that was slightly higher at the centre of the laser lesion points, but slightly lower at the periphery than in the control treatment, as shown by the vWF-positive staining, and this correlates with the impact of H7 IgG4 on the clinically relevant lesions. In addition, there was a higher incidence of laser lesions completely covered with RPE scar compared with the control animals which, themselves, had an increased incidence of "open" laser lesions with or without a central choroid scar. These results suggest a process of accelerated healing of the lesions in the animals receiving H7 IgG4, on the condition that the initial lesion created by the laser is similar between the control animals and the treated animals. The point size scores are not different between the animals treated with IgG4 and the control animals.

In conclusion, the administration of H7 IgG4 (ELB01101) by single bilateral intravitreal injection of 1 mg/eye was clinically well-tolerated in cynomolgus monkeys. This was also the case with the anti-CD160 H7 in the IgG1 N297Q format (ELB01111). H7 IgG4 was associated with a reduction in choroidal neovascularization compared with the carrier control (PBS), together with a slightly higher vascularization at the centre of the induced lesion than at the periphery and a higher incidence of lesions with healing of the RPE membrane, which suggests a process of accelerated recovery in the eyes treated with the anti-CD160 H7 IgG4 (ELB01101).

TABLE 19

Characterization of the laser lesions present

| | Saline control | | | | | | | H7 IgG4 | | | | | | |
|---|---|---|---|---|---|---|---|---|---|---|---|---|---|---|
| | 2101 | 2002 | 2003 | 2004 | 2005 | 2006 | Total No./group | 3001 | 3102 | 3003 | 3004 | 3005 | 3006 | Total No./group |
| Lesions covered with healing by the RPE membrane | | 1 | 5 | 1 | 0 | 9 | 16 | 4 | 2 | 5 | 8 | 6 | 7 | 32 |
| Open lesions | | 2 | 2 | 5 | 8 | 0 | 17 | 1 | 4 | 1 | 0 | 0 | 2 | 7 |
| Open lesions with central choroidal healing | | 4 | 2 | 2 | 1 | 0 | 9 | 4 | 3 | 1 | 1 | 3 | 0 | 12 |

EXAMPLE 10

Tolerability and Dose Efficacy Assessment of Intravitreal Injections of the Two Optimized Anti-CD160 mAb Formats (H7 Variant D12 as an IgG4 (ELB01103) and as a Fab-Linker Fab Format (ELB01132)) in the Laser-Induced (ChNV) Model in NHP As described in example 9, one single intravitreal injection of 1 mg per eye of the non-optimized anti-CD160 IgG4 (ELB01101) prevented by 50% the incidence of clinically relevant lesions relative to the total number of laser spots without signs of major ocular toxicity.

This first generation of anti-CD160 antibody was then optimized by affinity maturation as described in example 2 and different mAbs formats were designed as described in example 3. In example 8, the different formats of anti CD160 designed for ophthalmological purpose were compared in pharmacokinetic studies in rabbit and two of them, ELB01103 (the affinity optimized anti CD160 as an IgG4) and ELB01132 (the affinity matured as a Fab-linker-Fab) were selected.

Compared to ELB01101, ELB01103 has a reduced systemic half-life and still a good intravitreal half-life (4 days in rabbit). It should have an increased or equivalent efficacy to ELB01101 due to its affinity maturation. This affinity optimized anti CD160 was also generated as a Fab-linker Fab format to increase eye permeability, with a slightly reduced intravitreal half-life compared to ELB01103 and with a very shortened systemic half-life. The ELB01132 doses to be tested were calculated based on an equimolar basis with ELB01103. Indeed, the molecular mass of anti CD160 is roughly 150 KDa for the IgG ELB01103 and is reduced to 90 KDa for ELB01132.

The objectives of this study were: (1) to determine the tolerability of two anti-CD160 formats at three doses (0.35, 1 and 3 mg per eye for ELB01103 and 0.25, 0.6 and 2 for ELB01132) when given by a single bilateral intravitreal injection to the cynomolgus monkey, and (2) to evaluate their potential preventive effect on choroidal neovascularization in the laser-induced ChNV monkey model.

The protocols used in this study for the follow up of animals and for the assessment of tolerability and efficacy of test items (ELB011's candidates) were those described in previous example 9, with the following changes. The experimental design for the safety and dose assessment for efficacy of each anti CD160 isoform is described in Table 20 with 7 groups of 5 animals/group, male only.

TABLE 20

Experimental design of dose efficacy NHP experiment
Experimental Design

| Group No. | Test Material | Dose Level (mg/eye) | Dose Concentration (mg/mL) | Number of Males |
|---|---|---|---|---|
| 1 | Phosphate Buffered Saline | 0 | 0 | 5 |
| 2 | ELB01103 | 0.35 | 7 | 5 |
| 3 | (Anti-CD160 | 1 | 20 | 5 |
| 4 | isoform 1) | 3 | 60 | 5 |
| 5 | ELB01132 | 0.21 | 4.14 | 5 |
| 6 | Anti-CD160 | 0.59 | 11.83 | 5 |
| 7 | isoform 2 | 1.8 | 35.5 | 5 |

The test and reference items described in Table 21 were administered by bilateral intravitreal injection on day 0. The target dose volume for each animal was 50 µL/eye with the dose of item to be tested. The doses were given using a 1 mL syringe and an Exelint U-100 insulin 0.5 cc syringe with a 29 gauge×½-inch needle.

The batches of item that were tested are detailed in Table 21 below

TABLE 21

Items that were injected in dose efficacy study
Test and Reference Item Identification

| | Test Item | Test Item | Reference Item |
|---|---|---|---|
| Identification | ELB01103 (Anti-CD160 isoform 1) | ELB01132 (Anti-CD160 isoform 2) | Phosphate buffered saline (PBS) 1X Cat#TMS-012-A, Sigma Aldrich-MERCK, |
| Initial Concentration of the sent batch | 60 mg/mL | 40 mg/mL and 13.3 mg/mL and 4.6 mg/mL | |
| Volume, ml | 1.2 mL | 1.2 mL | 250 mL |
| Final concentrations that will be tested | 60 mg/mL and 20** mg/mL and 7** mg/mL | 35.5 mg/mL, 11.83** mg/mL and 4.14** mg/mL | |
| Endotoxin level (Endosafe ®-PTS ™; Charles River) | <0.5 EU/mL <0.025 EU/mg | <0.5 EU/mL <0.025 EU/mg | <0.5 EU/mL |
| Storage conditions | 2° C. to 8° C. | 2° C. to 8° C. | 2° C. to 8° C. |

**These solutions will be prepared by dilution of the items in PBS 1X

Laser-Induced Choroidal Neovascularization (ChNV) Procedure and Evaluation of Active ChNV Laser-induced ChNV procedure was the same as the one described in Example 9. On day 1, for the evaluation of ChNV, the eyes of 5 animals per group were successfully subjected to a 9-spot laser wound pattern between the major retinal vessels around the area of the macula of each eye using a 810 nm diode laser at an initial power setting of 300 mW, an initial spot size of 80 µm and a duration of 0.1 seconds. A total number of 90 laser sites/group was evaluated for each treatment (5 animals/group, 2 eyes/animal, 9 sites/eye by items to be tested).

The development of active ChNV lesions was assessed by fluorescein angiography (FA), once pre-study before injury and on days 14 and 28 after laser injury and the individual laser spots on the still images were also evaluated for leakage semi quantitatively on a scale of 0-4 by 2 independent readers with the same procedure as previously described in example 9.

Spectral Domain-Optical Coherence Tomography (SD-OCT)

To assess impact of anti CD160 lead candidates on retinal thickness at the lesion level site, there was an additional step of a spectral domain optical coherence tomography (SD OCT) analysis of the retina and of the different lesions sites. The SD-OCT analyses were only performed on intermediate dose groups (1 mg for ELB01103 and 0.6 mg for ELB01132) and for the vehicle group on Days 14 and 28. For that, the pupils will be dilated using a mydriatic agent (1% tropicamide and/or 2.5% phenylephrine). Animals will be anesthetized for fluorescein angiography, as indicated in example 9. Serial image through laser lesion of 5 sections through each lesion in both eyes were captured. The fibrovascular membrane area were measured for each section and total volume calculated for each spot. Measurement of retinal thickness in each lesion site compared to three measures outside of the lesion (normal retinal thickness evaluation). Additional scans or images were obtained, as deemed necessary.

The evolution over time of individual retinal thickness of each clinically relevant lesion could be followed as the mean change of individual retinal thickness over time (between D14 and D28). Efficacy of ELB011's candidates was then confirmed by looking at the incidence of candidates on retinal thickness of each clinically relevant lesion (grades 3+4) or of each grade 4 lesion and on evolution of retinal thickness at the lesion site over time (between D14 and D28).

Terminal Procedure and Bioanalysis (TK)

The terminal procedure for the animals was the same as the one described in example 9. Animals will be subjected to a limited necropsy examination, which will consist of an evaluation of the tissues collected.

Sclera-choroid-RPE complex, vitreous and aqueous humors were individually collected and kept frozen at −80° c. until analysis.

Some sera samples (0.75 mL) were collected for all animals using a collect via the femoral vein over time (once pre study; 2, 6, 12, 24 and 48 hours post dose; Days 4, 7, 14 and 28). These sera samples were kept at −80° c. until the bioanalysis to assess anti CD160 lead candidate concentration and or search and quantification of any eventual anti-drug antibodies directed against the anti CD160 leads.

Evaluation of Preventive and Therapeutic Efficacy of Lead Candidates

In this study compared to the one described in example 9, there are more analysed read outs to assess efficacy of these two anti CD160 lead candidates. Indeed, to assess efficacy of each anti CD160 isoform, first, their respective preventive effect was evaluated at Day 14 and Day 28
- on number and grade score of individual clinically relevant laser induced lesions
- on ChNV area of individual clinically relevant lesion and retinal thickness
- and, second, their respective therapeutic effect was evaluated by looking at the impact over time (between Day 14 and Day 28) on established active lesions at D14
- of mean grade score of clinically relevant lesions,
- of individual and mean ChNV area (in pixel) of clinically relevant lesions
- of individual and mean retinal thickness (for the two intermediate doses (1 mg for ELB01103 and 0.6 mg for ELB01132) in function of the types of lesions, (all grade, clinically relevant lesions (grade 3+4) and grade 4 only).

Results

The results of the ELB01103's and of ELB01132's profilings in terms of efficacy and tolerability was performed in the NHP ChNV model and are presented below.

ELB01103 and ELB01132 Safety Evaluation

As for ELB01101, and this whatever is the used ELB01103's or of ELB01132's intravitreal dose, clinical and ophthalmic examinations showed that there were no ELB01103 and ELB01132 treatment-related effects on hemorrhages or alteration of body weights or macroscopic findings others than some that they were considered as incidental or procedure-related and typical of laboratory-housed primates. Laser exposure resulted in similar procedure-related ocular changes in all treated eyes, which included retinal scarring, hemorrhages, and foveal hemorrhages. The chorioretinal hemorrhages improved over time and had resolved in most eyes by Day 28.

Figure 6:
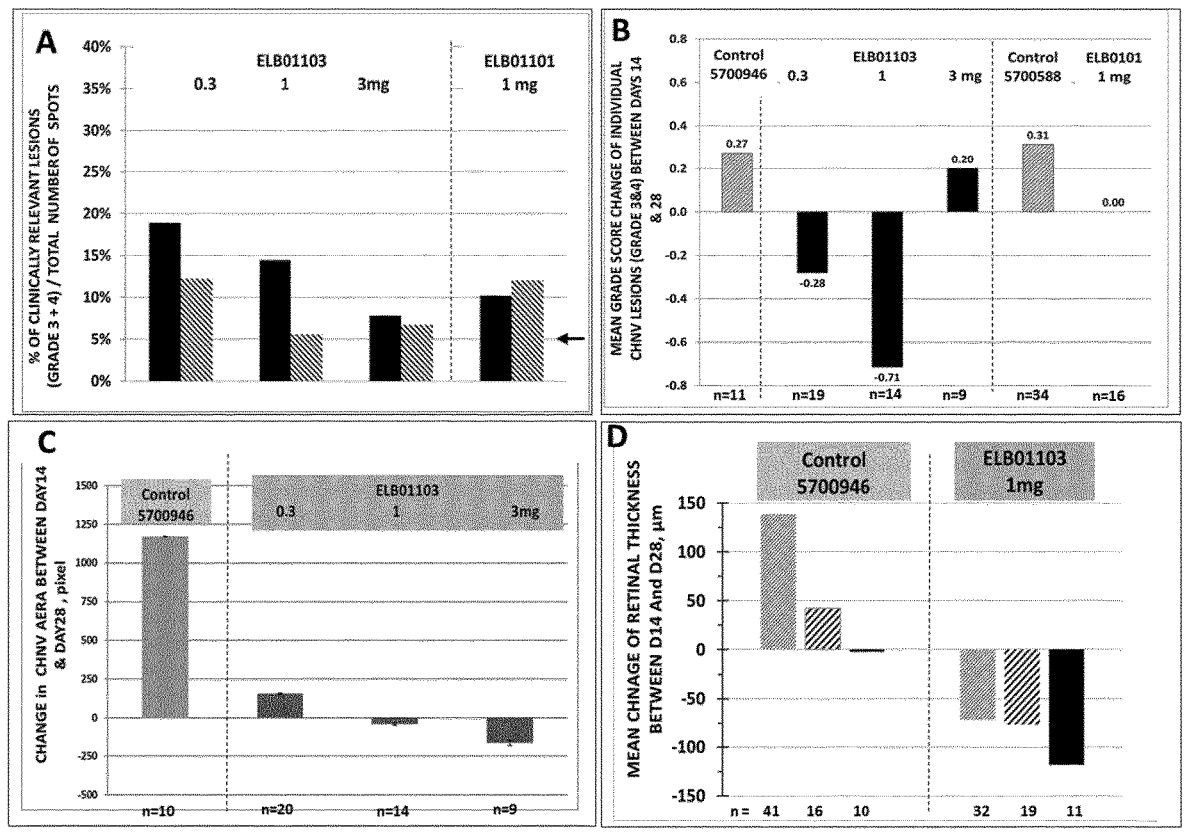
FIG. 6: Summary of dose efficacy data of H7 D12 in IgG4 format (ELB01103) in the monkey laser induced ChNV model.

Dose Efficacy of ELB01103 vs Vehicle Control and ELB01101 (H7 IgG4) in NHP ChNV Model As described in FIG. 6 panel A, the efficacy in a preventive setting of H7 variant D12 as an IgG4 (ELB01103) was first evaluated by looking at its incidence on clinically relevant lesions of high grade associated with significant fluorescein leakage (grades 3+4) over time (between Day 0 & Day 14 and Day 0 & Day 28). There are several possibilities to present the efficacy data obtained by semi quantitative evaluation of fluorescein angiograms.

First, the efficacy data could be presented by the impact of the tested item on percentage (%) of clinically relevant lesions/total number of laser induced lesions as described in panel A FIG. 6. This percentage corresponds to the number of clinically relevant lesions divided by the total number of potential lesions (here 90) for the 10 laser-induced monkey's eyes)*100. There is a clear dose-dependent efficacy emerged at the two highest doses (1 mg and 3 mg) of ELB01103. The impact over the lesions seems stronger at Day 28 than at Day 14 for groups 0.3 mg and 1 mg. At Day 14 maximal effect was reached for the 3 mg dose. At Day 28, 1 mg ELB01103 (affinity matured mAb) has a greater efficacy than an equivalent dose of ELB01101 (non-affinity matured H7 IgG4 candidate).

It is also possible to present the efficacy data looking at impact on % of eyes with at least 1 grade 4 lesion or by the impact on % of eyes with at least one clinically relevant lesions (grade 3+4). A dose efficacy of ELB01103 was also observed when these read outs are followed when one compared clinically relevant leakage (Grades 3/4) across groups and longitudinally (number of eyes or % of eyes with at least one grade 4 lesion, data not shown).

Then, the impact of ELB01103 on evolution of the leakage severity over time was assessed and this is represented in panel B of FIG. 6. The evolution of the leakage severity is seen by change over time (Day 14 to Day 28) of grade score of individual clinically relevant ChNV lesion. In panel B, when ELB01103 is injected intravitreally, there is a mean reduction in leakage severity for clinically individual lesions between Days 14 and 28, in particular at the mid-dose (1 mg/eye), and at the low-dose (0.3 mg/eye). Indeed, the mean change of grade score between Day 14 and Day 28 is clearly reduced with these doses. For the 3 mg dose, it appears that there is less control of leakage severity over time, but the analysis is done on only 9 lesions that evolved between Day 14 and Day 28 for the 3 mg dose due to a better antibody's efficacy at Day 14. However, the control of leakage severity for the 3 mg dose is still better than for the control group.

Furthermore, the impact of dose escalating (0.3 to 3 mg) of ELB01103 on mean change of ChNV area of clinically relevant lesions from Day 14 to Day 28 is described in panel C of FIG. 6. The measurement of lesion area showed that ELB01103-treated eyes were comparable to controls on Day 14 and had lower leakage at all dose levels when compared to the controls by Day 28. Indeed, while CHNV area progressed over time in vehicle control group, the progression of clinically relevant lesions that were not prevented at Day 14 was stopped between Day 14 and Day 28 when ELB01103 is added and this with a dose-response effect. Whatever is the ELB01103 dose, there is an important reduction of evolution of (individual data not shown) and of mean ChNV area between Day 14 and Day 28 and this with a dose response effect.

The impact of a dose of ELB01103 (1 mg) on mean change of retinal thickness depending of lesion grade between Day 14 and Day 28 is described in panel D of FIG. 6. While retinal thickness increased over time in vehicle control group, the growth of clinically relevant lesions followed by their retinal thickness was stopped between Day 14 and Day 28 when ELB01103 is added. This reduction of mean retinal thickness induced by ELB01103 between Day 14 and Day 28 is seen independently of the grade of the analysed lesion.

Dose Efficacy of ELB01132 vs Vehicle Control and ELB01101 (H7 IgG4) in NHP ChNV Model As described in FIG. 7 panel A, the efficacy in a preventive setting of H7 variant D12 as a Fab linker Fab (ELB01132) was first evaluated by looking at its incidence on clinically relevant lesions of high grade associated with significant fluorescein leakage (grades 3+4) over time. There is an efficacy of the two lowest doses (0.23 mg and 0.6 mg). However, there is no ChNV lesion prevention at all for the highest dose (2 mg). Consistently, the intermediate dose (0.6 mg) of ELB01132 is very efficient to prevent ChNV lesions appearance by Day 14 whatever is the observed read outs of efficacy (data not shown). This is true when one compared clinically relevant leakage (grades 3/4) across groups and longitudinally (number of eyes or % of eyes with at least one grade 4 lesion data not shown). The ELB01132's 0.6 mg dose efficacy is better than ELB01101's efficacy.

Then, the impact of ELB01132 on evolution of the leakage severity over time was assessed and this is represented in panel B of FIG. 7. The evolution of the leakage severity is seen by change over time (Day 14 to Day 28) of grade score of individual clinically relevant ChNV lesion. In panel B of FIG. 7, when ELB01132 is injected intravitreally, the ChNV lesions evolution was controlled only at low dose. In contrast, when mid- and high doses are used, there is an increased leakage. At intermediate dose, the control of leakage severity over time for the 2 mg dose is represented but the analysis is done on only 5 lesions due to antibody efficacy at Day 14. Regarding data obtained from the highest dose (2 mg), there is no control at all of ELB01132 on leakage at this dose.

Furthermore, the impact of dose escalating (0.25 to 2 mg) of ELB01132 on mean change of ChNV area of clinically relevant lesions from Day 14 to Day 28 is described in panel C of FIG. 7.

In eyes given ELB01132, smaller lesion areas were observed at the mid dose (0.6 mg/eye) on Days 14 and 28, when compared to the control eyes. Between Days 14 and 28, leakage development was only slightly lower than in the control eyes. Only the two highest doses tend to slightly reduce the increase evolution of mean ChNV area between Day 14 and Day 28.

The impact of a 0.6 mg dose of ELB01132 on mean change of retinal thickness of several types of lesions over time is described in panel D of FIG. 7. While retinal thickness increased between Day 14 and Day 28 in vehicle control group, the control of the 0.6 mg dose of ELB01132 on change over time of mean retinal thickness of lesions is much variable depending of lesions grade than for ELB01103. Indeed, when clinically relevant lesions of grades 3 and 4 are considered, the mean change of retinal thickness is drastically reduced with 0.6 mg ELB01132, but, this is not the case anymore when all grades of lesions or when only the grade 4 lesions are considered independently (see FIG. 14). However, in the case of the analysis of the grade 4 lesions the analysis is done on only 5 grade 4 lesions due to antibody efficacy at Day 14.

Conclusion

Administration of two isoforms of H7 variant D12 anti-CD160 by single bilateral intravitreal injection was clinically well-tolerated in cynomolgus monkeys at up to 3 mg ELB01103/eye and 2 mg ELB01132/eye. Both test items were associated with a reduction of ChNV progression, as measured by change in clinically relevant lesion area and/or thickness, when compared to the control. In general, the efficacy of ELB01103 was higher than observed for ELB01132. Indeed, there is a clear dose effect of the ELB01103 whatever is the analyzed efficacy read out while ELB011032 efficacy is much variable in function of dose and in function of efficacy read out. However, consistently, the intermediate dose (0.6 mg) of ELB01132 is very efficient to prevent ChNV lesions appearance.

EXAMPLE 11

Binding of the H7 IgG1 Antibody on Tumour Cells of CLL Patients

The PBMCs isolated from 7 CLL patients were labelled with the antibodies CL1-R2 (murine anti-CD160 IgG1), anti-CD160 H7 in IgG1 format, or BY55 (murine anti-CD160 IgM), in a CD19/CD5/CD3/CD56 panel (see FIG. 8). The CD5+CD19+ tumour cells were analysed in order to measure the fluorescence intensity of the CD160 labelling. CD160 expression is detectable on all the CLL samples with variable intensities. As can be seen in FIG. 8, the H7 IgG1 antibody binds efficiently to the tumour cells in 6/7 of the CLL samples examined and this better than CL1-R2 or commercial BY55 anti CD160 mAbs.

The H7 antibody in the IgG1 format is thus capable of binding to the tumour cells in the CLL, and can thus be used to target and kill these malignant cells by a cytotoxicity mechanism such as in particular ADCC or CDC.

EXAMPLE 12

In Vitro Evaluation of ADCC Induced by the H7 Antibody in the IgG1 Format on CD160-Positive Cells The anti-CD160 antibody H7 in the IgG1 format kills cells expressing CD160 by a mechanism of ADCC (see FIG. 9).

NK cells purified from the blood of a healthy donor were used as effectors in a test measuring the ADCC activity of the anti-CD160 H7 IgG1 antibody. The E300-CD160 target cells (transfected pre-B human cell line expressing CD160) were labelled with CFSE and incubated with the effector NK cells in the presence of the H7 IgG1 antibody or of a human IgG1 isotype control, at the effector/target ratios indicated (1/1, 1/5 and 1/10). The percentages of target cells killed were measured by labelling with 7AAD and flow cytometry analysis. The percentages of doubly labelled 7AAD+CFSE+ dead cells are indicated in the top right quadrant on the dot-plots presented.

These results and also those presented in FIG. 8 (Example 11) show that the H7 antibody in the IgG1 format can be used to target and kill cells expressing CD160 at their surface, by a mechanism of ADCC.

EXAMPLE 13

Activation of NK Cells and of Their Production of Interferon-Gamma by the H7 Antibody in the $IgG_1$ Format As shown by the results of FIGS. 10, 11 and 12, the anti-CD160 H7 antibody in the IgG1 format activates NK cells.

As shown in FIG. 10, panel A, the H7 IgG1 antibody is capable of binding to the surface of human NK cells purified from peripheral blood.

FIG. 10, panel B, shows that H7 IgG1 induces the production of interferon-gamma (IFN-γ) by NK cells. NK cells purified from the blood of a healthy donor were cultured for 24 h in wells of 96-well plates ($1\times10^{+6}$ cells per well) alone or in the presence of the H7 IgG1 antibody, or of a human IgG1 isotype control, concentrated to 1 or 10 μg/ml. The IFN-γ was assayed by ELISA in the culture supernatants. The results presented are means of triplicates+/−sem.

FIG. 10, panel C shows that H7 IgG1 induces the expression of the CD69 activation marker on NK cells. In the same experiment as in panel B, the NK cells were collected after 24 h of culture and labelled with an anti-CD69 antibody conjugated to the fluorochrome APC. The percentages of CD69-positive cells were analysed by flow cytometry. The means(+/−sem) were calculated from triplicates.

The anti-CD160 H7 antibody in the IgG1 format, but not in the IgG4 format, activates NK cells, as shown in FIG. 11. NK cells purified from the blood of a healthy donor were cultured alone or in the presence of the following antibodies concentrated to 5 μg/ml: H7 IgG1, H7 IgG4, their respective human IgG1 or IgG4 isotype controls, or the antibodies ELB01103, ELB01104 and ELB01106, which are variants derived from the H7 antibody in the IgG4 format. All the antibodies were controlled to verify the absence of contamination by endotoxins. The anti-CD16 antibody (ebioscience cat #16-0166) is used as positive control. The NK cells ($5\times10^{+5}$ per well) were collected after 24 h of culture and labelled with an anti-CD69 antibody conjugated to the fluorochrome APC. The percentages of CD69-positive cells were analysed by flow cytometry (means of triplicates+/−SD). The anti-CD160 H7 in the IgG1 format induces the expression of the CD69 activation marker on NK cells, whereas the same antibody in the IgG4 format has no effect. The variants of H7 in the human IgG4 format (ELB01103, ELB01104 and ELB01106) also do not exhibit any activating effect on NK cells.

EXAMPLE 14

Increased NK Cell-Stimulating Activity with the Different Variants of H7 in the IgG1 and E345K/IgG1 Formats As shown by the results of FIG. 12: The variants derived from the anti-CD160 H7 antibody in the IgG1 and E345K/IgG1 formats have an increased capacity to activate NK cells. NK cells purified from the blood of a healthy donor were cultured for 24 h in wells of 96-well plates ($1\times10^{+6}$ cells per well), alone or in the presence of the anti-CD160 H7 IgG1 antibody, or of the variants ELB02102, ELB02103, ELB02104 (all three in the IgG1 format), ELB02112, ELB02113 or ELB02114 (all three in the E345K/IgG1 format) produced by ElsaLys, at doses of 0.001 to 10 μg/ml. A human IgG1 at 10 μg/ml was used as negative isotype control, and an anti-CD16 (ebioscience cat #16-0166) was used as positive control.

The IFN-gamma was assayed by ELISA in the culture supernatants. The results presented are means of triplicates+/−sem.

The NK cells were collected and labelled with an anti-CD69 antibody conjugated to the fluorochrome APC. The percentages of CD69-positive cells were analysed by flow cytometry. The means(+/−sem) were calculated from triplicates.

These results were analysed using the GraphPad Prism software for generating non-linear regression curves (Log (agonist) vs response, 3-parameter equations) and calculating the median effective concentrations (EC50s). The EC50s for induction of CD69 were not calculated for the 3 variants ELB02112, ELB02113 or ELB02114, because of the mortality observed with the concentrations greater than or equal to 0.1 μg/ml. The mortality of the NKs stimulated by these E345K/IgG1 formats is probably induced following the strong activation of the cells.

All of these results show that the three variants of H7 in the IgG1 format (ELB02102, ELB02103, ELB02104) are much more potent than the original H7 IgG1 antibody (ELB02101) for activating NK cells, with an improvement of 2 to 3 logs in the EC50s.

The three variants of H7 in the E345K/IgG1 format (that is to say ELB02112, ELB02113, ELB02114) exhibit a further increased capacity for inducing IFN-gamma production, with an additional improvement of 2 logs in the EC50s (4 logs relative to the original H7 IgG1 antibody (ELB02101)).

The results presented in Examples 13 and 14 show that the H7 antibodies and the variants thereof in the IgG1 and E345K/IgG1 formats are capable of activating NK cells and of inducing their IFN-γ production. These properties make them capable of stimulating the immune response in patients suffering from cancer, via NK cells, and indirectly via T lymphocytes and antigen-presenting cells activated by IFN-γ, a cytokine known to activate Th1-type responses.

Furthermore, these properties make the antibodies derived from H7 in the IgG1 and E345K/IgG1 formats potentially capable of increasing the ADCC cytotoxic activity induced by other antibodies possessing this mode of action that would be co-administered, and thus would make it possible to improve their therapeutic effects.

EXAMPLE 15

Labelling of NK and CD8+ T Cells by the Variants of the H7 Antibody in the IgG1 and E345K/IgG1 Formats The variants derived from the anti-CD160 H7 antibody in the IgG1 and E345K/IgG1 formats label NK and CD8+ T cells more efficiently (FIG. 13).

The PBMCs (peripheral blood mononuclear cells) of two healthy donors were analysed by flow cytometry after immunolabelling with anti-CD45, CD3, CD4, CD8 and CD19 antibodies and with the anti-CD160 antibodies indicated conjugated to PE (Lynx Rapid RPE Antibody Conjugation Kit ref LNK022RPE) (0.25 µg for 5×10$^{+5}$ PBMCs). An irrelevant human IgG1 (hIgG1) was used as negative control, the Fc receptors were saturated with a human Fc (Rockland), 15 min AT.

In FIG. 13, panel A: The variants of H7 in the IgG1 format (ELB02102, ELB02103, ELB02104) or E345K/IgG1 format (ELB02112, ELB02113, ELB02114) bind more efficiently to NK cells than the original H7 IgG1 antibody, with 60% to 80% of NK cells positively labelled. In FIG. 13, panel B: A population of CD8+ T cells, clearly detected in donor 2, is also labelled more efficiently with the H7 variants.

These results show that the variants derived from the anti-CD160 H7 antibody in the IgG1 and E345K/IgG1 formats bind to NK and CD8+ T cells more efficiently than the original H7 IgG1 antibody.

These results and those presented in the previous examples show that the H7 IgG1 antibody and the variants thereof in the IgG1 and E345K/IgG1 formats can bind not only to NK cells and stimulate their activity, but also to a population of CD8$^+$CD160$^+$ T lymphocytes, the activity of which they could also modulate.

EXAMPLE 16

Design and Generation of Bispecific Antibodies (bsabs) for the Anti-CD160 Candidates, Optimized for Ophthalmology and Oncology Possible Bispecifics (bsabs) with an Anti-CD160 for Ophthalmology Indications: Potential Second Valency to be Combined with an Anti-CD160 H7 or Affinity Matured.

The strategy described by (Labrijn et al., 2014) was applied for developing a bispecific IgG from the parental antibodies anti-hCD160 IgG1 F405L (clone H7) or a derivative thereof) and IgG1 K409R consisting of an anti hAngiopoietin 2 as proof of concept.

One of the antibodies is chosen from Table 22 (for the ophthalmology application) or from Table 23 (for the oncology application). This first antibody is in the IgG1 N297Q H310A-H435Q K409R format for ophthalmology or IgG1 K409R format for oncology. The second antibody is the anti-CD160 H7 (or a variant thereof). This second antibody is in the IgG1 N297Q H310A-H435Q F405L format for the ophthalmic indications and in the IgG1 F405L format for the oncology.

TABLE 22

Antibody targeting antigens that can be used in ophthalmology as second potential valency for producing an anti-CD160 bsab or to be used in combination therapy with an anti-CD160 H7 or a variant thereof.

| Antibody against human antigen targeted | bsab or combination therapy | Rationale |
| --- | --- | --- |
| Anti-angiopoietin 2 Pathway blocker | Combination therapy or bsab | Inhibits neo-angiogenesis |
| Anti-CD200R (agonist) | Combination therapy or bsab | Inhibits TEMs and inflammation Inhibits VEGF secretion by macrophages (inhibition of the neo-angiogenesis?) |
| Anti-angiopoietin like 4 | Combination therapy or bsab | Inhibits neo-angiogenesis by targeting anti-apoptotic signals No impact on inflammation |

TABLE 22-continued

Antibody targeting antigens that can be used in ophthalmology as second potential valency for producing an anti-CD160 bsab or to be used in combination therapy with an anti-CD160 H7 or a variant thereof.

| Antibody against human antigen targeted | bsab or combination therapy | Rationale |
| --- | --- | --- |
| Anti-PDGF BB | Combination therapy or bsab | Inhibits pericyte stabilization |
| Anti-VEGF (avastin or lucentis) | Combination | Inhibits neo-angiogenesis by targeting pro-angiogenic factors |
| Anti-beta amyloid | Combination therapy or bsab | Inhibits inflammation |
| Anti-PS | Combination therapy or bsab | Inhibits neo-angiogenesis by targeting abnormal vascularization |
| Anti-sphingosine-1-phosphate | Combination therapy or bsab | Inhibits neo-angiogenesis by targeting abnormal vascularization |
| Anti-C'5 | Combination therapy or bsab | Inhibits inflammation |
| Anti-CD115 | Combination therapy | M1/M2 Polarization |

TABLE 23

Antibody targeting antigens that can be used in oncology as potential second valency for producing an anti-CD160 bsab or to be used in combination therapy with an anti-CD160 H7 or a variant thereof.

| Antibody against human antigen targeted | bsab or combination therapy | Rationale |
| --- | --- | --- |
| Anti-Ang2 | Combination therapy or bsab | Inhibits neo-angiogenesis Inhibits TEMs and inflammation |
| Anti-CD200R | Combination therapy or bsab | Inhibits TEMs and inflammation Inhibits VEGF secretion by macrophages (inhibition of neo-angiogenesis?) |
| Anti-CD19 or -CD20 | Combination therapy or bsab | Simultaneous targeting of two antigens on CLLs for increasing tumour specificity and efficacy of B CLL cell lysis. |
| Anti-CD200 as CLL TAA taa | Combination therapy or bsab | Simultaneous targeting of two antigens on CLLs for increasing tumour specificity and efficacy of B CLL cell lysis. |
| Anti-CD180 | Combination therapy or bsab | Simultaneous targeting of two antigens on CLLs and on marginal zone lymphomas (MZL) for increasing tumour specificity and the efficacy of B lymphoma lysis. |
| Anti-CD148 | Combination therapy or bsab | Simultaneous targeting of two antigens on CLLs and on mantel cell tumours (MCL) for increasing tumour specificity and the efficacy of B lymphoma lysis. |
| Anti-CD47 | Combination therapy or bsab | Increase of ADCP in addition to ADCC |

This technology can be used to generate the anti-CD160 bsab candidates according to the targeted ophthalmology, oncology or immunotherapy indications.

EXAMPLE 17

Evaluation of the Anti-hCD160/Anti-Human Angiopoietin 2 or Anti-hCD160/Anti-Human CD200R Combination Therapies and Bispecifics The combination therapies of anti-CD160 and its anti-X partner antibody (in particular where X is angiopoietin 2 or CD200R) and anti-CD160/anti-X bispecifics are evaluated for their efficacy and for the additivity and/or the synergy of their efficacy in the rabbit model of corneal neovascularization induced in sodium hydroxide (NaOH) buffer as described in (Campos-Mollo et al., 2011), at two doses of each antibody (100 and 500 µg) or 100 and 500 µg of the bsab.

EXAMPLE 18

Antibodies According to the Invention are Able to Bind on CD160 GPI and CD160 TM, Although CL1-R2 Antibody Recognizes Only CD160 GPI>>

The binding capacity of the anti-CD160 CL1-R2, ELB02101 (H7 IgG1) antibodies and of the H7 variants in the ELB02104, ELB02114 and ELB01103 formats was evaluated during the labelling of surface human CD160-GPI (glycosylphosphatidylinositol), expressed in a recombinant cell line CHO-S-hCD160-GPI (clone 2G10) and during the labelling of surface human CD160-TM (transmembrane), expressed in a recombinant cell line CHO-S-hCD160-TM in comparison with non-transfected CHO-S cells, by measuring the percentage of cell labelled=percentage of binding (see FIG. 14). For this, $2 \times 10^{+5}$ CHO-S-hCD160-GPI, CHO-S-hCD160-TM and non-transfected CHO-S cells were labelled with 1 µg of each of these antibodies and also with the appropriate control isotypes.

In FIG. 14, all the anti-CD160 tested (regardless of the isotype or the IgG format or the variant) specifically recognize human CD160-GPI expressed recombinantly by the CHO-S cells. Humanized ELB02101 (H7 IgG1) and the H7 variants in their different formats ELB02104, ELB02114 and ELB01103 bind more efficiently to the CHO-hCD160-GPI transfectants than the parental CL1-R2. Unexpectedly humanized ELB02101 (H7 IgG1) and the variants ELB02104, ELB02114 and ELB01103 bind also to human CD160-TM expressed recombinantly by the CHO-S cells while parental CL1-R2 mAb is not able to do that whatever is the tested dose.

EXAMPLE 19

T CD4 Re-Activation Through the Blocking of HVEM-CD160 Interaction by the H7 Variant: ELB02104

As shown by the results of FIG. 15, the A09 variant derived from the anti-CD160 H7 antibody in the IgG1 format (ELB02104) is able to re-activate T CD4 $CD45^{High}$ CD160+ lymphocytes compare to control isotype. Through the blocking of HVEM-CD160 interaction, ELB02104 removes the inhibition of TCD4 cells induced by HVEM protein.

T CD4 lymphocytes cells purified from the blood of a healthy donor were cultured for 16 h in 96-well plates ($1 \times 10^{+6}$ cells per well), in the presence of the anti-CD160 mAb: ELB02104 or with the appropriate control isotype at 10 µg/ml and with anti-CD3 (clone UTCH1) mAb+/−anti-CD28 (clone CD28.2) mAb+/−HVEM protein (10334-H08H, Sino biological) coated on the plate.

T CD4 lymphocytes were collected and labelled with a viability marker: Zombie NIR, an anti-CD45RA antibody conjugated to the fluorochrome BB515 targeting Naïve/Memory cells, with an anti-CD160 (clone BY55) antibody conjugated to the fluorochrome Alexa fluor 647 targeting CD160 expressing cells and with an anti-CD69 antibody conjugated to the fluorochrome PE targeting activated cells. The percentage of Zombie NIR−/$CD45RA^{high}$+/CD160+/CD69+ positive cells were analysed by flow cytometry. The means(+/−sem) were calculated from duplicates. Results show that the H7 A09 variant in the IgG1 format (ELB02104) blocks HVEM-CD160 interaction and removes the inhibition of TCD4 cells induced by HVEM protein as shown by the upregulation of CD69, an activation marker express by T CD4 $CD45RA^{High}$ CD160+ cells.

HVEM is expressed by several cancers and play a role in tumor progression and immune evasion. Blocking HVEM-CD160 axis on T CD4 cells may restore anti-tumoral responses by T CD8 cytotoxic generation.

EXAMPLE 20

DC (Dendritic Cells) Maturation Through NK Cell-Stimulating Activity of H7 IgG1 (ELB02101) and of H7 A09 in the IgG1 (ELB02104) and E345K/IgG1 (ELB02114) Formats The H7 A09 variant antibody in the IgG1 (ELB02104) and E345K/IgG1 (ELB02114) formats have an increased capacity to induce DC maturation cells through NK cell-stimulating activity compare to H7 IgG1 (ELB02101) and contrary to parental CL1-R2 mAb.

Monocytes cells purified from the blood of a healthy donor were differentiated in immature dendritic cells with GM-CSF (100 ng/mL) and IL-4 (20 ng/mL) for 6 days. NK cells purified from the blood of a healthy donor were cultured for 16 h in 96-well plates ($1 \times 10^{+6}$ cells per well), alone or in the presence of the anti-CD160 mAbs: CL1-R2, H7 IgG1 (ELB02101), or of the variants ELB02104 (in the IgG1 format), ELB02114 (in the E345K/IgG1 format) or ELB01103 (in the IgG4 format), at 10 µg/ml and also with the appropriate control isotypes. Immature DC ($1 \times 10^{+5}$ cells per well) were coculture with NK previously incubated with anti-CD160 mAbs 24 h.

The DC/NK co-culture cells were collected and labelled with a viability marker: Zombie NIR, an anti-CD11c antibody conjugated to the fluorochrome PE-Cy7 targeting DC cells, with an anti-CD56 antibody conjugated to the fluorochrome Viobright 515 targeting NK cells and with an anti-CD86 antibody conjugated to the fluorochrome BV421 targeting mature DC cells. The percentage of Zombie NIR−/CD11c+/CD86+ positive cells were analyzed by flow cytometry. The means(+/−sem) were calculated from duplicates.

Results show that H7 A09 variant in the IgG1 (ELB02104) and in the E345K/IgG1 (ELB02114) formats have an increased capacity to induce DC maturation cells (as shown by CD86 upregulation) through NK cell-stimulating activity compare to H7 IgG1 (ELB02101). Surprisingly parental CL1R2 mAb has not this property to induce DC maturation.

The results presented in examples 13 and 14 show that the H7 antibodies and the variants thereof in the IgG1 and E345K/IgG1 formats are capable of activating NK cells and inducing their IFN-γ production. These properties make them capable of stimulating DC maturation and indirectly via the cross talk between mature DC and T lymphocytes to drive the generation of cytotoxic T lymphocytes with antitumoral properties in cancer patients.

BIBLIOGRAPHY

Giustiniani et al., J Immunol. 2009 Jan. 1; 182(1):63-71—Identification and characterization of a transmembrane isoform of CD160 (CD160-TM), a unique activating receptor selectively expressed upon human NK cell activation El-Far et al., J Transl Med. 2014 Sep. 2; 12:217. doi: 10.1186/s12967-014-0217-y. CD160 isoforms and regulation of CD4 and CD8 T-cell responses.

E A Kabat, T T Wu, C Foeller, H M Perry, K S Gottesman (1991) Sequences of Proteins of Immunological Interest Diebolder et al., Science. 2014 Mar. 14; 343(6176):1260-3. doi: 10.1126/science.1248943—Complement is activated by IgG hexamers assembled at the cell surface. Diebolder C A de Jong et al., Published online 2016 Jan. 6. doi: 10.1371/journal.pbio.1002344—A Novel Platform for the Potentiation of Therapeutic Antibodies Based on Antigen-Dependent Formation of IgG Hexamers at the Cell Surface Wang et al., Mol. Cell. 2016 Jul. 7; 63(1):135-45. doi: 10.1016/j.molcel.2016.05.016—Molecular Basis of Assembly and Activation of Complement Component C1 in Complex with Immunoglobulin G1 and Antigen.

Krzystolik et al., Arch Ophthalmol. 2002 March; 120(3): 338-46—Prevention of experimental choroidal neovascularization with intravitreal anti-vascular endothelial growth factor antibody fragment.

Gadkar et al., Invest Ophthalmol Vis Sci. 2015 August; 56(9):5390-400. doi: 10.1167/iovs.15-17108—Design and Pharmacokinetic Characterization of Novel Antibody Formats for Ocular Therapeutics Labrijn et al., Nat Protoc. 2014 October; 9(10):2450-63. doi: 10.1038/nprot.2014.169. Epub 2014 Sep. 25. —Controlled Fab-arm exchange for the generation of stable bispecific IgG1

---

The invention claimed is:

1. A compound which binds specifically to human CD160 and chosen from the group consisting of antibodies, fragments thereof and derivatives thereof, the compound comprising:
 a light chain variable domain (VL) of SEQ ID No: 14,
 and a heavy chain variable domain (VH) chosen from SEQ ID No: 11, SEQ ID No: 25, SEQ ID No: 26, SEQ ID No: 27, SEQ ID No: 28, SEQ ID No: 29 and SEQ ID No: 30.

2. The compound according to claim 1, wherein this compound is a monoclonal antibody.

3. The compound according to claim 1, wherein it is a monoclonal antibody which has, as heavy chain constant domain, a sequence chosen from SEQ ID No: 15, SEQ ID No: 16, SEQ ID Nos 31 to 35, SEQ ID Nos 43 and 44 and the aglycosylated mutants thereof, and as light chain constant domain, a sequence chosen from SEQ ID No: 22, SEQ ID No: 23 and SEQ ID No: 24.

4. The compound according to claim 1, having a light chain defined by SEQ ID No: 57 and as heavy chain a sequence chosen from SEQ ID Nos: 45 to 51, SEQ ID No: 9, SEQ ID No: 10, SEQ ID No: 12 and SEQ ID Nos: 58 to 64.

5. The compound according to claim 1, wherein it is a fragment chosen from a Fab, a Fab' and a F(ab')2, and comprising a light chain defined by SEQ ID No: 57 and a heavy chain comprising a sequence chosen from SEQ ID No: ID 36, SEQ ID No: 37 and SEQ ID No: 38.

6. The compound according to claim 1, wherein it is a derivative of the compound chosen from scFvs, multimeric scFvs fused to an Fc fragment, diabodies, triabodies, tetrameric scFvs, dimers of which each monomer comprises an scFv bonded to a heavy chain fragment, dimers of which each monomer comprises an scFv bonded to heavy chain fragments, F(ab')2s fused in the C-terminal position to a leucine zipper domain, single-domain antibodies, forms comprising at least 2 Fabs bonded head-to-tail and a tetravalent antibody.

7. The compound according to claim 1, wherein it is a multispecific, or at least bispecific, derivative and that it comprises at least one CD160-binding site and one site for binding of another antigen.

8. The compound according to claim 7, wherein the other antigen is chosen from the following antigens: VEGF-A, VEGF-B, VEGF-C, VEGF-D, PIGF, VEGF-R2, angiopoietin 2; angiopoietin like 4, CD200R, PDGF-AA, PDGF-AB, PDGF-BB, PDGF-CC, PDGF-DD, PDGF-R, FGF such as FGF, beta-amyloid, sphingosine-1-phosphate (S1 P), C'S, IL6, MER TK, CD1 15, TNF alpha, IL8, HGF, TGF beta, IGF1, IL1, IL2, EGF, KGF, G-CSF, GM-CSF, alpha-v,beta-3 or alpha-v,beta-5 integrins, transmembrane or soluble CD146; MMP 1, MMP 2, MMP 9, MT1 -MMP, TIMP-2; angiogenic PD-ECGF, platelet activation factor; prostaglandin E, pleiotropin, class II MHC, t HP59, CM101, CD3, CD25, CD28, PD1, CTLA4, 4-1 BB, LAG-3, ICOS, CD16, CD3, CD47, CD20, CD19, CD5, CD180, CD200, CD40, CD20, CD37, CD38, CD148, CD180 and any other antigen specific for B-type lymphomas.

9. A composition comprising at least one compound according to claim 1.

10. The composition according to claim 9, also comprising at least one other antibody directed against one of the antigens chosen from the following antigens: VEGF-A, VEGF-B, VEGF-C, VEGF-D, PIGF, VEGF-R2, angiopoietin 2; angiopoietin like 4, CD200, CD200R, PDGF-AA, PDGF-AB, PDGF-BB, PDGF-CC, PDGF-DD, PDGF-R, FGF, beta-amyloid, sphingosine-1-phosphate (S1 P), C'5, IL6, MER TK, CD1 15, TNF alpha, IL8, HGF, TGF beta, IGF1, IL1, IL2, EGF, KGF, G-CSF, GM-CSF, alpha-v,beta-3 or alpha-v,beta-5 integrins, transmembrane or soluble CD146; MMP 1, MMP 2, MMP 9, MT1 -MMP, TIMP-2; angiogenin; PD-ECGF, platelet activation factor; prostaglandin E, pleiotropin, class II MHC, HP59, CM101, CD37, CD38, CD25, CD28, CD40, PD1, CTLA4, 4-1 BB, LAG-3, ICOS, CD16, CD3, CD47, CD20, CD19, CD5, CD180, CD200, CD40, CD20, CD37, CD38, CD148, CD180 and any other antigen specific for B-type lymphomas .

11. A medicament comprising the compound according to claim 1.

12. A product comprising:
 the compound according to claim 1;
 and at least one antibody directed against one of the antigens chosen from the following antigens: VEGF-A, VEGF-B, VEGF-C, VEGF-D, PIGF, VEGF-R2, angiopoietin 2; angiopoietin like 4, CD200, CD200R, PDGF-AA, PDGF-AB, PDGF-BB, PDGF-CC, PDGF-DD, PDGF-R, FGF, beta-amyloid, sphingosine-1-phosphate (51 P), C'S, IL6, MER TK, CD1 15, TNF alpha, IL8, HGF, TGF beta, IGF1, IL1, IL2, EGF, KGF, G-CSF, GM-CSF, alpha-v,beta-3 or alpha-v,beta-5 integrins, transmembrane or soluble CD146; MMP 1, MMP 2, MMP 9, MT1 -MMP, TIMP-2; angiogenin; PD-ECGF, platelet activation factor; prostaglandin E, pleiotropin, class II MHC, HP59, CM101, CD37, CD38, CD25, CD28, CD40, PD1, CTLA4, 4-1 BB, LAG-3, ICOS, CD16, CD3, CD47, CD20, CD19, CD5, CD180, CD200, CD40, CD20, CD37, CD38, CD148, CD180 and any other antigen specific for B-type lymphomas;
 wherein the product is for simultaneous, separate or sequential use in the treatment of a pathological condition which causes a neovascularization chosen from neovascular ocular pathological conditions, diabetes, diabetic blindness, primary diabetic retinopathy or age-related macular degeneration, rheumatoid arthritis, pre-eclampsia, eclampsia or cancers.

13. The medicament according to claim 11, for use as an anti-angiogenic, immunomodulator and/or cytotoxic agent.

14. A method for treating a pathological condition, comprising administering the medicament according to claim 11 to a subject having the pathological condition, wherein the pathological condition is chosen from neovascular ocular pathological conditions, diabetes, diabetic blindness, primary diabetic retinopathy or age-related macular degeneration, rheumatoid arthritis, pre-eclampsia, eclampsia or cancers.

15. The method of claim 14, wherein the pathological condition is a cancer.

16. The method of claim 14, wherein the pathological condition is a haematological cancer and at least one other anti-CD20 antibody, anti-CD37 antibody; anti-CD38 antibody or anti-CD40 antibody is administered to the subject.

17. An isolated nucleic acid encoding the compound according to claim 1.

18. A vector comprising the nucleic acid according to claim 17.

19. A host cell comprising the vector according to claim 18.

20. A method for producing a compound, comprising culturing the host cell according to claim 19 so as to produce the compound which binds specifically to human CD160.

* * * * *